United States Patent
Stearns et al.

(10) Patent No.: US 9,597,112 B2
(45) Date of Patent: Mar. 21, 2017

(54) LOW-PROFILE SURGICAL ACCESS DEVICES WITH ANCHORING

(75) Inventors: Ralph Stearns, Bozrah, CT (US);
James R. Parys, Cheshire, CT (US);
Kurt Azarbarzin, Fairfield, CT (US)

(73) Assignee: Surgiquest, Inc., Milford, CT (US)

( * ) Notice: Subject to any disclaimer, the term of this patent is extended or adjusted under 35 U.S.C. 154(b) by 1144 days.

(21) Appl. No.: 13/388,644

(22) PCT Filed: Oct. 8, 2010

(86) PCT No.: PCT/US2010/051955
§ 371 (c)(1),
(2), (4) Date: Sep. 24, 2012

(87) PCT Pub. No.: WO2011/044448
PCT Pub. Date: Apr. 14, 2011

(65) Prior Publication Data
US 2013/0012782 A1    Jan. 10, 2013

Related U.S. Application Data

(63) Continuation of application No. 12/577,189, filed on Oct. 11, 2009, now Pat. No. 9,289,233, which is a (Continued)

(51) Int. Cl.
*A61B 1/32* (2006.01)
*A61B 17/34* (2006.01)
(Continued)

(52) U.S. Cl.
CPC .......... *A61B 17/3417* (2013.01); *A61B 17/02* (2013.01); *A61M 39/0247* (2013.01);
(Continued)

(58) Field of Classification Search
CPC ............ A61B 17/3421; A61B 17/3423; A61B 17/3425; A61B 17/3427; A61B 17/3429
See application file for complete search history.

(56) References Cited

U.S. PATENT DOCUMENTS

| 4,184,510 A | 1/1980 | Murry et al. |
| 4,535,773 A | 8/1985 | Yoon |

(Continued)

FOREIGN PATENT DOCUMENTS

| DE | 19523685 A1 | 1/1997 |
| EP | 0323018 B1 | 6/1993 |

(Continued)

OTHER PUBLICATIONS

Office Action issued Sep. 17, 2013 for corresponding JP Application No. 2011-531240 including English translation.
(Continued)

*Primary Examiner* — Matthew Lawson
(74) *Attorney, Agent, or Firm* — Locke Lord LLP; Scott D. Wofsy

(57) ABSTRACT

A surgical access device includes a proximal housing having proximal and distal end portions, the distal end portion of the housing being configured and adapted to engage a proximal portion of a flexible wound retractor. The proximal housing can be provided with a plenum chamber being defined therein, the plenum chamber being in fluid communication with at least one nozzle. The nozzle is preferably configured to direct pressurized fluid in an axial direction from the plenum chamber into a central bore of the surgical access device to provide a constant gaseous seal around a surgical instrument inserted therethrough, while inhibiting a loss of pressurized fluid from the body cavity therethrough. The
(Continued)

plenum chamber can be adapted and configured to receive pressurized fluid and conduct the pressurized fluid to the at least one nozzle.

10 Claims, 68 Drawing Sheets

Related U.S. Application Data continuation of application No. PCT/US2009/060299, filed on Oct. 10, 2009.

(60) Provisional application No. 61/250,521, filed on Oct. 11, 2009, provisional application No. 61/370,938, filed on Aug. 5, 2010, provisional application No. 61/104,475, filed on Oct. 10, 2008.

(51) Int. Cl.
  *A61B 17/02* (2006.01)
  *A61M 39/02* (2006.01)
  *A61M 39/04* (2006.01)

(52) U.S. Cl.
  CPC ....... *A61B 17/3423* (2013.01); *A61B 17/3431* (2013.01); *A61B 17/3474* (2013.01); *A61B 17/3498* (2013.01); *A61B 2017/3445* (2013.01); *A61B 2017/3484* (2013.01); *A61M 39/045* (2013.01); *A61M 2039/0261* (2013.01); *A61M 2039/0264* (2013.01); *A61M 2039/0276* (2013.01); *A61M 2039/0279* (2013.01)

(56) References Cited

U.S. PATENT DOCUMENTS

| | | | |
|---|---|---|---|
| 4,735,603 A | 4/1988 | Goodson et al. | |
| 4,792,335 A | 12/1988 | Goosen et al. | |
| 4,869,717 A | 9/1989 | Adair | |
| 5,002,557 A | 3/1991 | Hasson | |
| 5,013,294 A | 5/1991 | Baier | |
| 5,190,068 A | 3/1993 | Philbin | |
| 5,199,944 A | 4/1993 | Cosmescu | |
| 5,203,767 A | 4/1993 | Cloyd | |
| 5,284,473 A | 2/1994 | Calabria | |
| 5,290,249 A | 3/1994 | Foster et al. | |
| 5,300,047 A | 4/1994 | Beurrier | |
| 5,312,351 A | 5/1994 | Gerrone | |
| 5,328,458 A | 7/1994 | Sekino et al. | |
| 5,366,446 A | 11/1994 | Tal et al. | |
| 5,429,483 A | 7/1995 | Tamari | |
| 5,545,150 A | 8/1996 | Danks et al. | |
| 5,545,179 A * | 8/1996 | Williamson, IV | A61B 17/3423 600/32 |
| 5,556,386 A | 9/1996 | Todd | |
| 5,720,759 A | 2/1998 | Green et al. | |
| 5,800,381 A | 9/1998 | Ognier | |
| 5,849,005 A | 12/1998 | Garrison et al. | |
| 5,906,577 A * | 5/1999 | Beane | A61B 17/0293 600/206 |
| 5,916,198 A | 6/1999 | Dillow | |
| 6,042,573 A | 3/2000 | Lucey | |
| 6,162,196 A * | 12/2000 | Hart | A61B 17/3462 604/167.02 |
| 6,217,555 B1 | 4/2001 | Hart et al. | |
| 6,228,058 B1 | 5/2001 | Dennis et al. | |
| 6,253,766 B1 | 7/2001 | Niles et al. | |
| 6,299,592 B1 | 10/2001 | Zander | |
| 6,302,873 B1 | 10/2001 | Moenning | |
| 6,309,382 B1 | 10/2001 | Garrison et al. | |
| 6,482,181 B1 | 11/2002 | Racenet et al. | |
| 6,497,687 B1 | 12/2002 | Blanco | |
| 6,508,859 B1 | 1/2003 | Zia et al. | |
| 6,544,210 B1 | 4/2003 | Trudel et al. | |
| 6,551,270 B1 * | 4/2003 | Bimbo | A61B 17/3421 604/167.03 |
| 6,645,197 B2 | 11/2003 | Garrison et al. | |
| 6,685,665 B2 | 2/2004 | Booth et al. | |
| 6,811,546 B1 * | 11/2004 | Callas | A61B 17/3423 604/167.06 |
| 6,905,489 B2 | 6/2005 | Mantell et al. | |
| 6,942,671 B1 | 9/2005 | Smith | |
| 7,297,141 B2 | 11/2007 | Kathrani et al. | |
| 7,563,250 B2 | 7/2009 | Wenchell | |
| 2002/0120226 A1 | 8/2002 | Beck | |
| 2002/0128603 A1 | 9/2002 | Booth et al. | |
| 2002/0161387 A1 | 10/2002 | Blanco | |
| 2003/0014076 A1 | 1/2003 | Mollenauer et al. | |
| 2003/0040711 A1 | 2/2003 | Racenet et al. | |
| 2003/0045834 A1 | 3/2003 | Wing et al. | |
| 2004/0034339 A1 | 2/2004 | Stoller et al. | |
| 2004/0199121 A1 | 10/2004 | Wenchell et al. | |
| 2004/0204671 A1 | 10/2004 | Stubbs et al. | |
| 2005/0004512 A1 | 1/2005 | Campbell et al. | |
| 2005/0015043 A1 | 1/2005 | Stubbs et al. | |
| 2005/0059865 A1 | 3/2005 | Kahle et al. | |
| 2005/0241647 A1 | 11/2005 | Nguyen et al. | |
| 2006/0079925 A1 | 4/2006 | Kerr | |
| 2006/0182637 A1 | 8/2006 | Jacobsen et al. | |
| 2006/0217665 A1 * | 9/2006 | Prosek | A61B 17/3421 604/167.02 |
| 2006/0247498 A1 | 11/2006 | Bonadio et al. | |
| 2006/0247500 A1 | 11/2006 | Voegele et al. | |
| 2006/0258899 A1 | 11/2006 | Gill et al. | |
| 2007/0088274 A1 | 4/2007 | Stubbs et al. | |
| 2007/0088275 A1 | 4/2007 | Stearns et al. | |
| 2008/0281161 A1 * | 11/2008 | Albrecht | A61B 1/32 600/206 |
| 2009/0137943 A1 | 5/2009 | Stearns et al. | |

FOREIGN PATENT DOCUMENTS

| | | | |
|---|---|---|---|
| EP | 1188415 | A3 | 5/2002 |
| JP | 2002-508195 | A | 3/2002 |
| JP | 2005506144 | A | 3/2005 |
| JP | 2005110978 | A | 4/2005 |
| JP | 2007-044395 | A | 2/2007 |
| JP | 2008-515523 | A | 5/2008 |
| WO | WO-9601132 | A1 | 1/1996 |
| WO | WO-98019736 | A1 | 5/1998 |
| WO | WO-9929250 | A1 | 6/1999 |
| WO | WO-0037134 | A1 | 6/2000 |
| WO | WO-0191653 | A3 | 5/2002 |
| WO | WO-02085444 | A1 | 10/2002 |
| WO | WO-03034908 | A2 | 5/2003 |
| WO | WO-02033108 | A3 | 10/2003 |
| WO | WO-2006040748 | A1 | 4/2006 |
| WO | WO-2008077080 | A2 | 6/2008 |
| WO | WO-2008093313 | A1 | 8/2008 |
| WO | WO-2010042915 | A2 | 4/2010 |
| WO | WO-2010051955 | A1 | 5/2010 |

OTHER PUBLICATIONS

International Search Report issued Apr. 14, 2011 for corresponding PCT Application No. PCT/US2010/051955.
Written Opinion issued Apr. 10, 2012 for corresponding PCT Application No. PCT/US2010/0051955.
International Search Report issued Jun. 14, 2010 for corresponding PCT Application No. PCT/US2009/060299.
Written Opinion issued Apr. 10, 2011 for corresponding PCT Application No. PCT/US2009/060299.
Exair: Air Jets and Nozzles "How Air Jet Nozzles Work" brochure from www.exair.com, 2003.
EME: "Infant Flow System," Electro Medical Equipment Ltd., brochure, from www.ememed.co.uk., 2003.
Invitation to Pay Additional Fees issued Jun. 15, 2007 in connection with PCT Application No. PCT/US2006/045961.
International Search Report and Written Opinion issued Mar. 9, 2009 in connection with PCT Application No. PCT/US2007/088017.

(56) References Cited

OTHER PUBLICATIONS

International Search Report and Written Opinion issued Aug. 23, 2007 in connection with PCT Application No. PCT/US2006/045961.
Office Action for Korean Patent Application No. 1020117009618, dated Oct. 8, 2015.
Extended Search Report issued Jun. 3, 2016 in connection with corresponding EP Publication No. EP2349033.

* cited by examiner

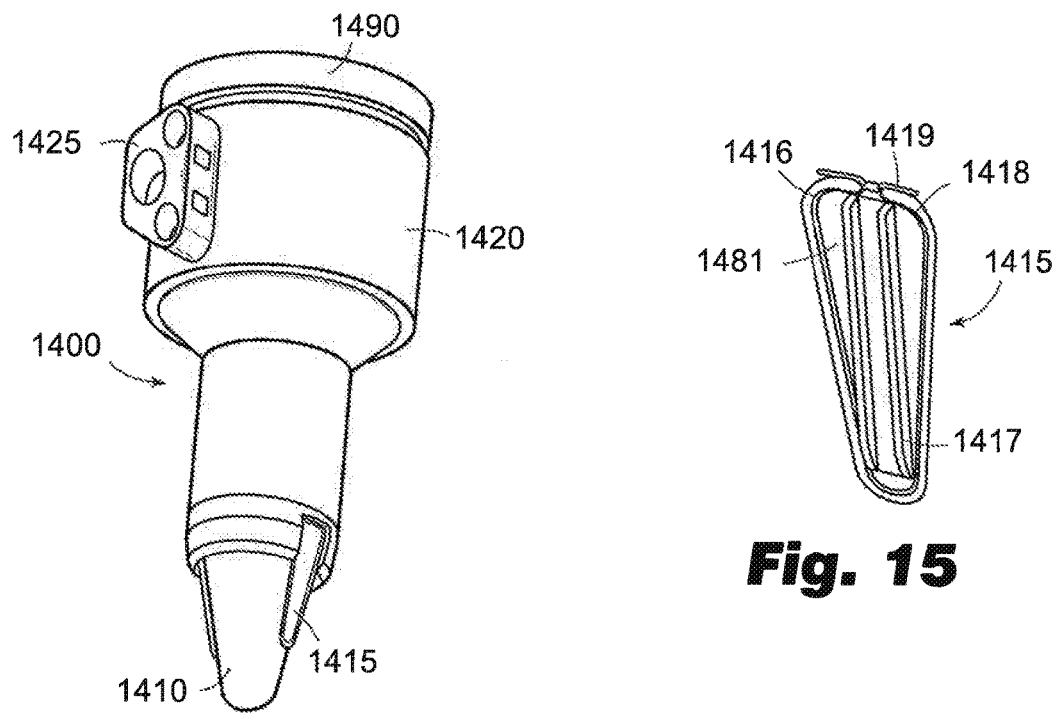
Fig. 14
Fig. 15
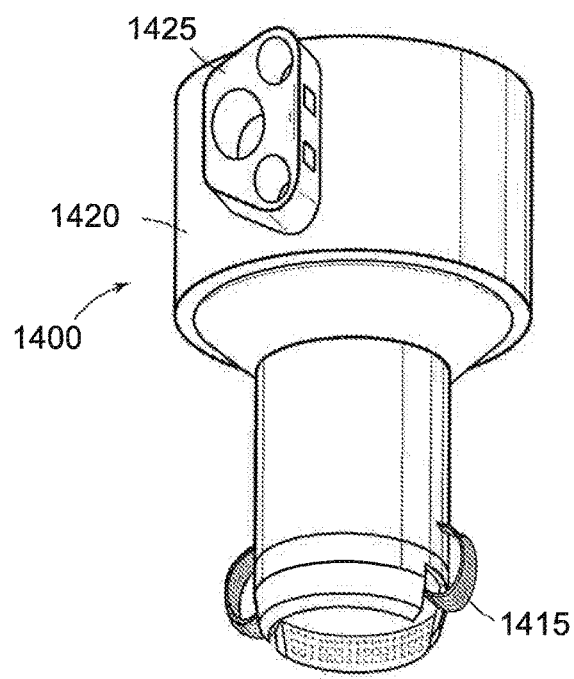
Fig. 16

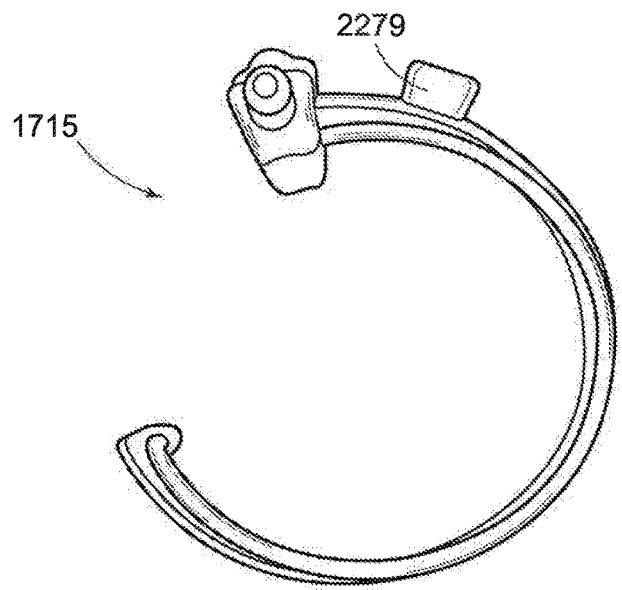
Fig. 24
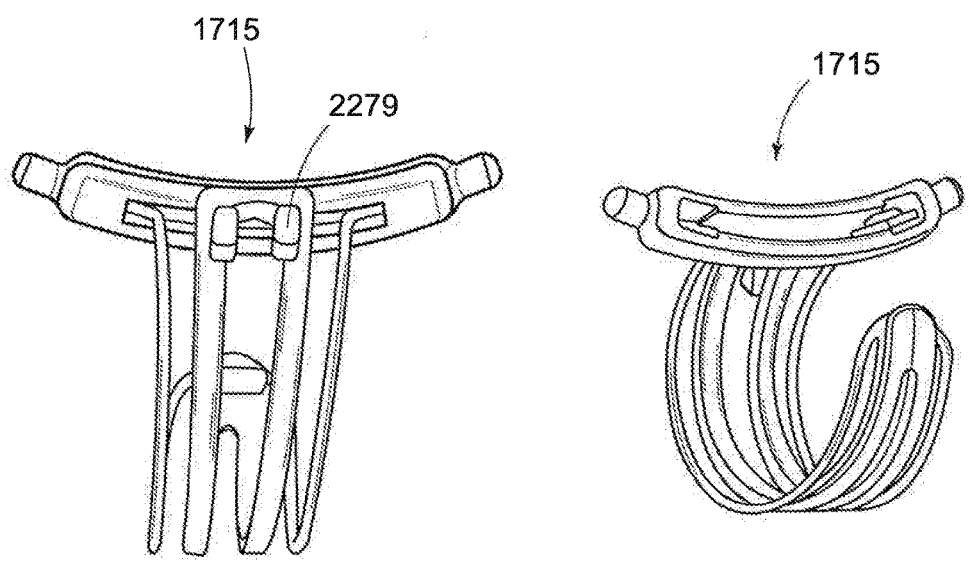
Fig. 25 Fig. 26

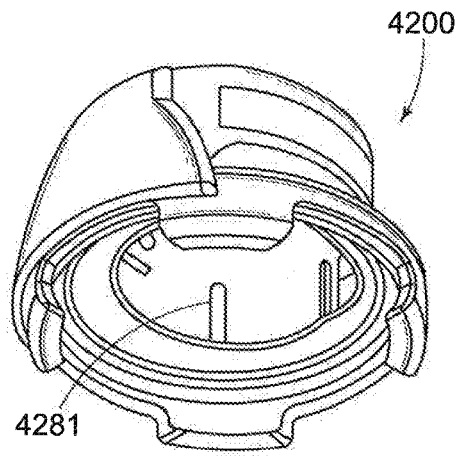
Fig. 48
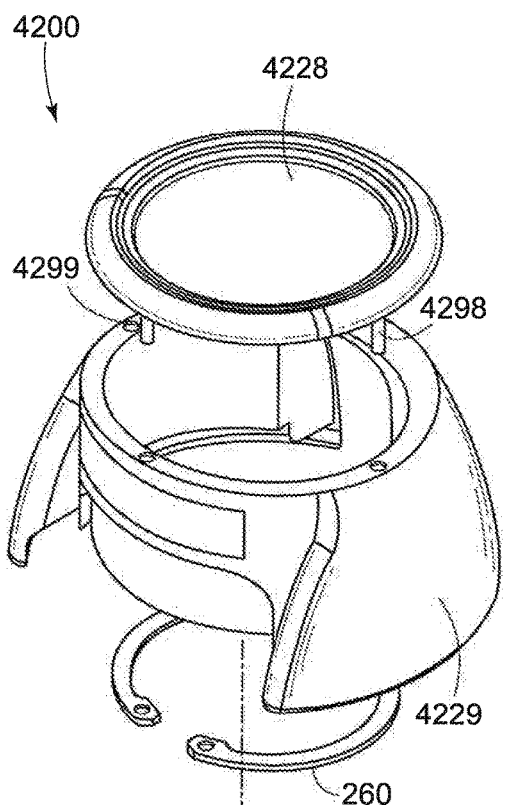
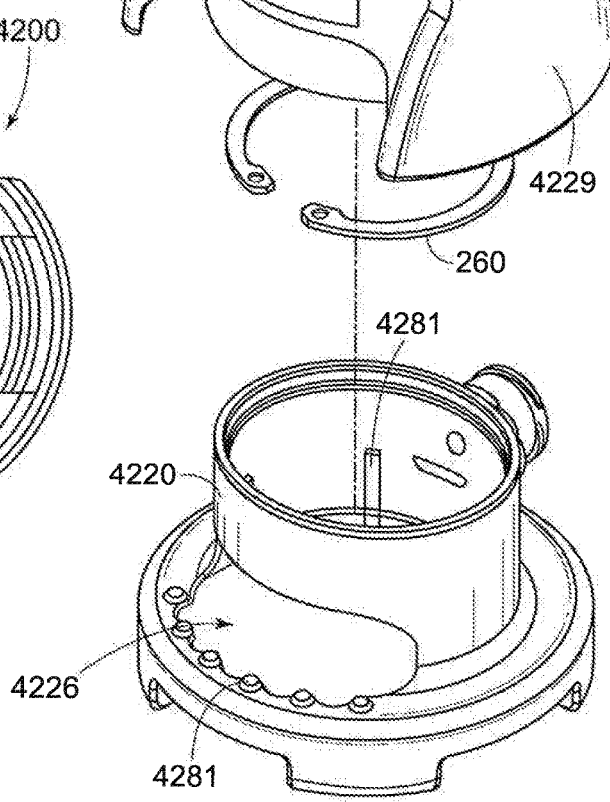
Fig. 49
Fig. 50

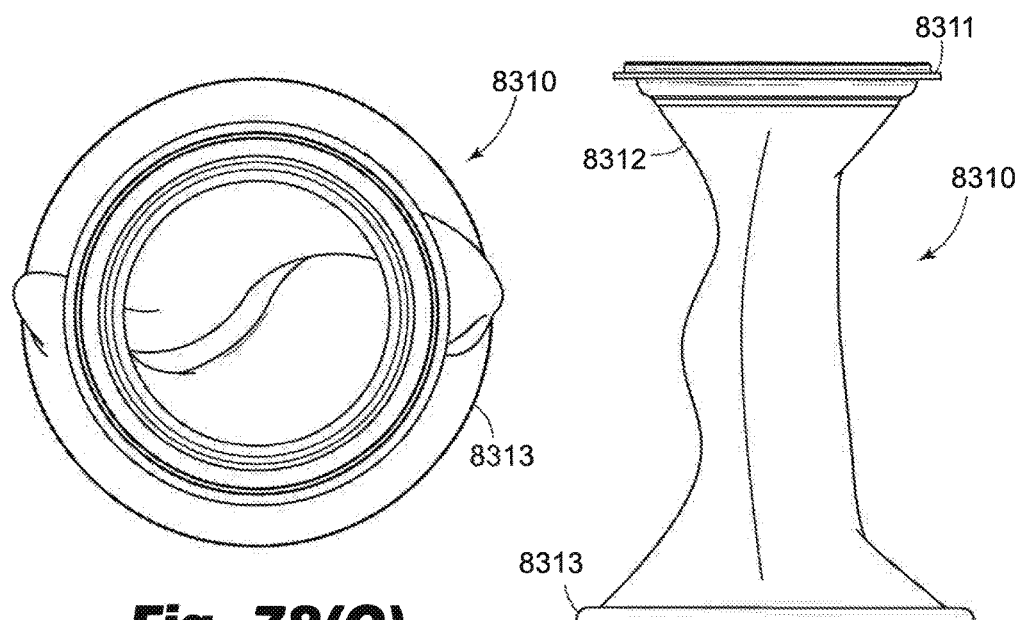
Fig. 78(C)
Fig. 78(D)
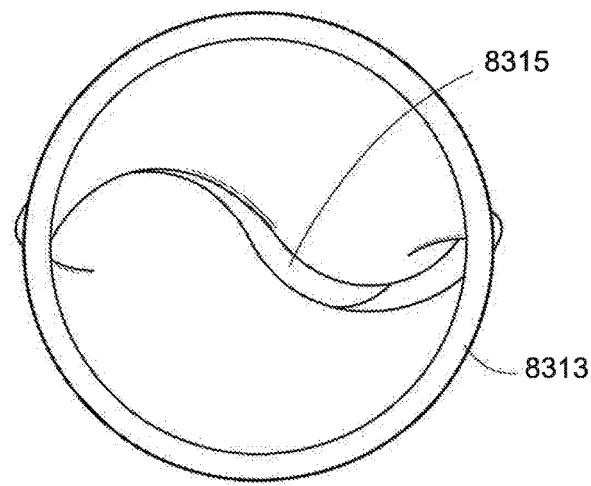
Fig. 78(E)

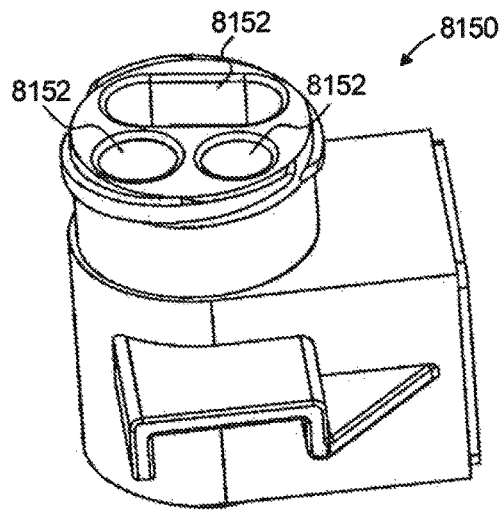
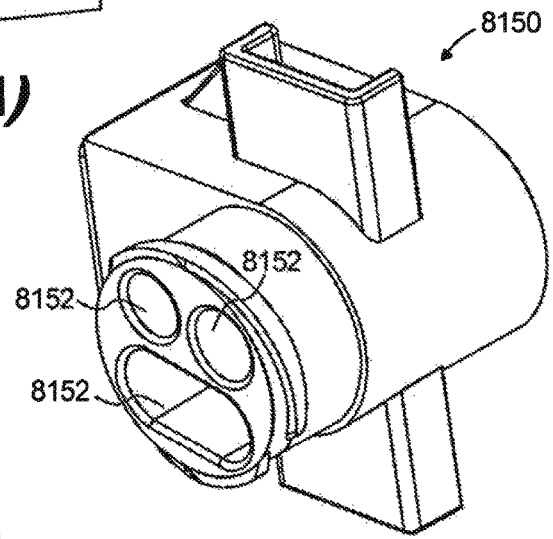
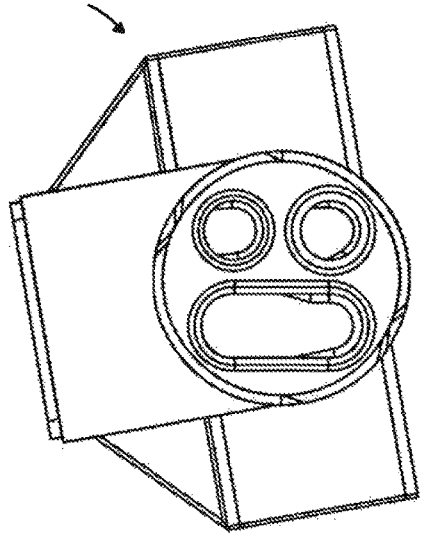
Fig. 83(A)
Fig. 83(B)
Fig. 83(C)

LOW-PROFILE SURGICAL ACCESS DEVICES WITH ANCHORING

CROSS-REFERENCE TO RELATED APPLICATIONS

This application is a U.S. National Stage Application under 35 U.S.C. §371 of International Application No. PCT/US2010/51955 filed Oct. 8, 2010 which claims the benefit of U.S. Provisional Patent Application No. 61/370,938 filed Aug. 5, 2010 and U.S. Provisional Application No. 61/250,521, filed Oct. 11, 2008 and is a continuation of U.S. patent application Ser. No. 12/577,189 filed Oct. 11, 2009 which is a continuation of PCT Application No. PCT/US2009/60299, filed Oct. 10, 2009, which claims the benefit of priority to U.S. Provisional Patent Application No. 61/104,475, filed Oct. 10, 2008.

This application is also related to U.S. Pat. Nos. 7,182,752, 7,338,473, and 7,285,112, U.S. Patent Application Publication Number US 2007/0088275 and PCT Application No. PCT/US2007/88017, published as Publication No. WO2008/077080. Each of the foregoing patents and applications is incorporated herein by reference in its entirety.

FIELD OF THE INVENTION

The present invention relates to surgical access devices for performing minimally-invasive surgical procedures. Particularly, the present invention is directed to surgical access devices that are particularly adapted to securely anchoring in an incision, such as one made through the abdominal wall of a patient. The present invention is also directed to such surgical access devices that include a non-mechanical pressure barrier for inhibiting loss of peritoneal pressure under abdominal insufflation.

DESCRIPTION OF RELATED ART

A variety of access devices are known in the art for accessing a surgical site, such as the abdominal cavity. Typically, ensuring that such access devices stay securely mounted in the abdominal wall without causing excessive trauma is a primary goal. The present invention provides various solutions to these problems.

SUMMARY OF THE DISCLOSURE

The purpose and advantages of embodiments of the present invention will be set forth in and apparent from the description that follows.

To achieve these and other advantages and in accordance with the purpose of the invention, as embodied, the invention includes, in one aspect, a surgical access device including a housing having proximal and distal end portions, an access tube extending distally from the distal end of the housing, adapted and configured to extend at least partially though an incision formed in the abdominal wall of a patient, the access tube having a hyperbolic shape in cross section, with an expanded-diameter distal portion to inhibit removal from an incision, and a cover disposed over a proximal end portion of the housing adapted and configured to reduce sound from fluid flowing through the access device.

In accordance with further aspects, the cover can include a removable lid. The cover can include a sound-absorbing material. If desired, the cover can include an engagement portion adapted to engage with the housing, and a lid portion attached to the engagement portion by way of a hinge. The housing can include a distal housing portion having a discontinuous bottom end with extensions interrupted by openings.

In accordance with another embodiment, the disclosure provides a surgical access device having a housing having proximal end and a distal end, wherein the housing defines a side access port through a wall thereof between the proximal and distal ends. The device further includes an access tube extending distally from the distal end of the housing, adapted and configured to extend at least partially though an incision formed in the abdominal wall of a patient, the access tube having a an expanded-diameter distal portion to inhibit removal from an incision.

In accordance with further aspects, the device an further include a door to reduce sound from fluid flowing through the access device. The door is pivotable and/or flexible. A plenum chamber is preferably defined within the housing, the plenum chamber being in fluid communication with at least one nozzle, and being configured to direct pressurized fluid in an axial direction from the plenum chamber into a central bore of the access tube to provide a constant gaseous seal around a surgical instrument inserted therethrough, while inhibiting a loss of pressurized fluid from the body cavity therethrough, and wherein the plenum chamber is adapted and configured to receive pressurized fluid and conduct the pressurized fluid to the at least one nozzle. The plenum chamber preferably includes an inlet port for communicating with a source of pressurized fluid.

In accordance with a further aspect, the nozzle can be defined by a gap defined by an outer periphery of a nozzle insert disposed within the proximal housing and an inner periphery of a substantially annular insert disposed within the proximal housing. A pressure sensing chamber can be defined within the housing that is adapted and configured to be in fluid communication with the abdominal cavity of the patient to facilitate sensing of abdominal pressure. The pressure sensing chamber can have an outlet port for communicating with a pressure sensor of a connected system. The sensing chamber can be in fluid communication with a sensing channel defined in the access tube of the surgical access device. In some embodiments, the access tube can be a flexible wound retractor. If desired, the housing can define a plurality of side access ports through the wall. If desired, the housing can define a plurality of protrusions adjacent to the side access port, the protrusions being adapted and configured to hold and inhibit sliding of surgical instruments inserted through the port.

The disclosure further provides a wound protector having a proximal end portion, a central tubular structure, and a distal anchor portion, wherein the distal anchor portion is connected to the central tubular structure a web, wherein the central tubular structure supports the distal anchor portion by way of the web.

In accordance with further aspects, the web can define a plurality of apertures therethrough to facilitate manipulation of the wound protector. The wound protector can include at least one of elastomeric material and a shape-memory alloy.

The disclosure still further provides a wound protector having a proximal end portion, a central tubular portion, a distal anchor portion and defines a longitudinal axis along its center between the proximal end portion and distal end portion, wherein the central tubular portion has an undulating configuration and defines a substantially sinusoidal aperture therethrough in a plane that is generally perpendicular to the longitudinal axis.

In accordance with further aspects, the aperture can be defined between opposing walls of the wound protector. In one embodiment, the aperture can be completely sealed by the opposing walls collapsing on each other. In another embodiment, the aperture can be adapted and configured to remain partially open. The wound protector is preferably adapted and configured to permit the passage one or more instruments through the aperture, and further wherein the walls move away from one another without stretching when instruments are passed through the aperture to permit the aperture to expand.

The disclosure further provides surgical access device including a nozzle assembly mounted for polyaxial spatial adjustability about a point of rotation, and a base portion adapted and configured to receive the nozzle assembly, the base portion including an access tube extending distally from the base portion, the tube being adapted and configured to extend at least partially though an incision formed in the abdominal wall of a patient, the access tube having a an expanded-diameter distal portion to inhibit removal from an incision.

The nozzle assembly can include a tube connection for mating with a high-pressure fluid source. The nozzle assembly can be held in place by a plurality of stanchions extending proximally from the base portion. The stanchions can define substantially spherical inner surface portions for mating with substantially spherical outer surface portions of the nozzle assembly. The nozzle assembly can include an annular upper portion and an annular lower portion separated by a plurality of standoffs to maintain a predetermined spacing between the upper and lower portions, wherein the upper and lower portions cooperate to define a pressure plenum therebetween. The upper portion and lower portion of the nozzle can be sealed within a ring shaped housing by a plurality of seal elements disposed in circumferential grooves on an outer peripheral edge of each of the upper and lower portion.

The disclosure further provides a surgical access device, including an outer cannula, an inner cannula disposed within the outer cannula including a wound protector, a tube center component disposed within a central bore of a ring jet assembly, wherein the tube center component and ring jet assembly cooperate to define a plurality of fluid nozzles disposed about a central axis of the device, and a fluid manifold attached to an exterior portion of the outer cannula.

In accordance with a further aspect, the wound protector can include a proximal end portion, a central tubular portion, a distal anchor portion and can define a longitudinal axis along its center between the proximal end portion and distal end portion, wherein the central tubular portion has an undulating configuration and defines a substantially sinusoidal aperture therethrough in a plane that is generally perpendicular to the longitudinal axis.

It is to be understood that both the foregoing general description and the following detailed description are exemplary and are intended to provide a non-limiting explanation of the invention.

BRIEF DESCRIPTION OF THE DRAWINGS

The accompanying drawings, which are incorporated in and constitute part of this specification, are included to illustrate and provide a further understanding of the method and system of the invention. Together with the description, the drawings serve to explain the principles of the invention, wherein:

FIGS. 2-6 illustrate a second exemplary embodiment of a surgical access device in accordance with the invention, which is adapted for use with flexible wound retractors and the like;

FIGS. 14-16 illustrate a fifth exemplary embodiment of a surgical access device in accordance with the invention, having opposed deployable anchor elements;

FIGS. 17-26 illustrate a sixth exemplary embodiment of surgical access devices in accordance with the invention, having circumferentially arranged deployable anchor elements;

FIGS. 42-50 illustrate a further embodiment of a surgical access device in accordance with the invention having a housing with a cover, in-turn with an optional removable lid, as well as a side-access port;

FIGS. 77-83 illustrate yet a further embodiment of a surgical access device in accordance with the disclosure, which is adapted for use with flexible wound retractors and the like; and FIGS. 84-85 illustrate still another embodiment of a surgical access device in accordance with the invention, which is adapted for use with flexible wound retractors and the like.

DETAILED DESCRIPTION

Reference will now be made in detail to the presently preferred embodiments of the invention, examples of which are illustrated in the accompanying drawings. The related methods of the invention will be described in conjunction with the detailed description of the devices.

Figure 1:
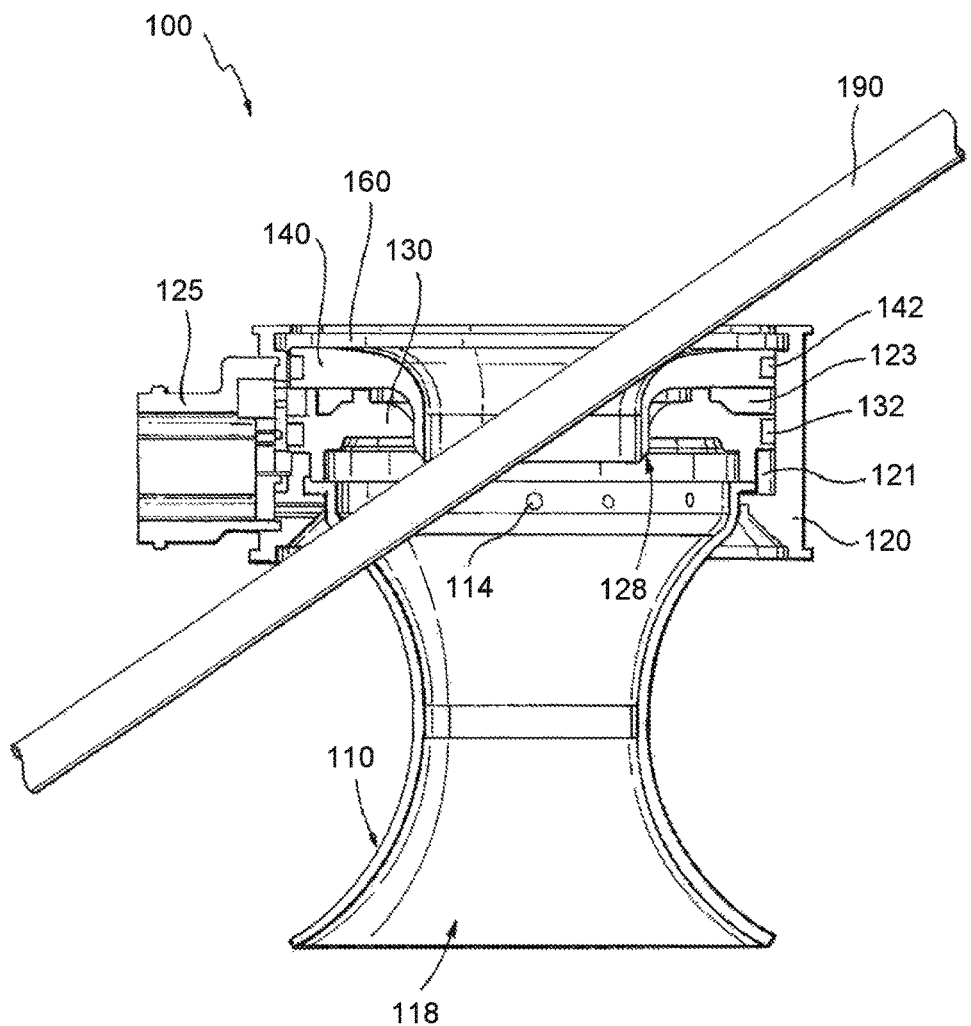
FIG. 1 is a cross sectional view of one embodiment of an example surgical access device in accordance with the invention, having a substantially hyperbolic flexible body tube.
Figure 2:
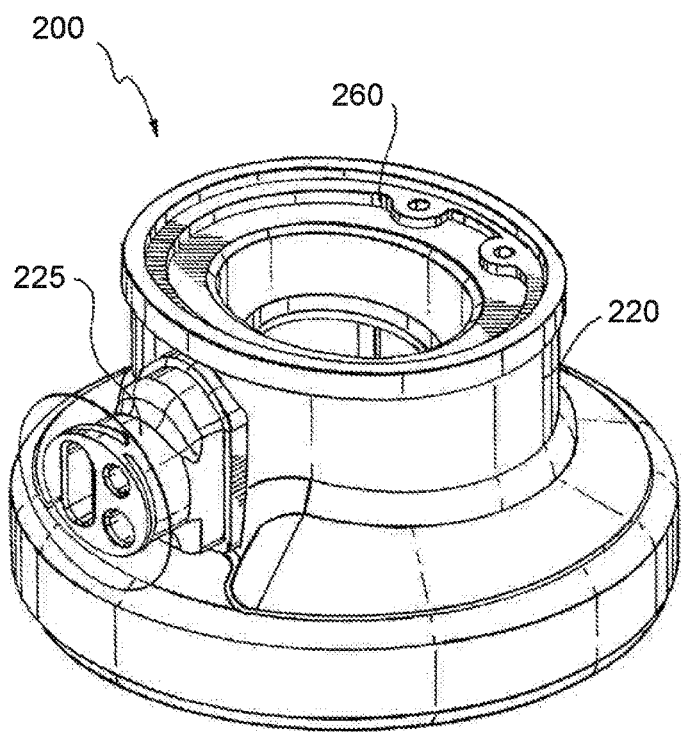
Figure 3:
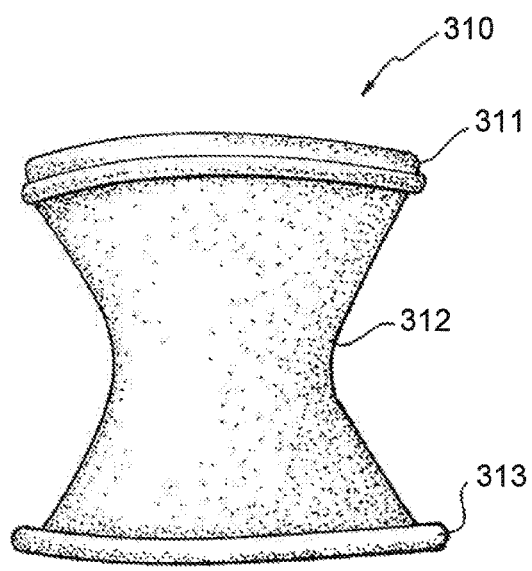

In accordance with the invention, and as illustrated in FIG. 1, a surgical access device 100 is provided, which is advantageously has a relatively low profile, allowing surgical instruments 190 inserted therethrough to be less restricted in movement than with more conventional surgical access devices. The access device 100 includes a housing 120, and a compliant access tube 110 extending distally from the distal end of the housing 120. The access tube 110 is adapted and configured to extend at least partially though an incision formed in the abdominal wall of a patient. In the illustrated embodiment, the access tube 110 has hyperbolic shape in cross section. An expanded-diameter distal portion of the access tube 110 inhibits removal of the access device 100 from the incision formed in the patient. In accordance with the invention, the length of the access tube 110 can be sufficiently long so as to extend fully though the abdominal wall of the patient and into the peritoneal space.

In accordance with the invention, the access device 100 can further include insufflation capability, can be adapted and configured to form a fluidic seal or barometric barrier around an instrument inserted therethrough and/or can be adapted to facilitate recirculation of insufflation gasses. Details of such capabilities are set forth in U.S. Pat. No. 7,182,752, U.S. Pat. No. 7,285,112, U.S. Pat. No. 7,338,473, U.S. Pat. Publication No. US 2007/0088275 and PCT Publication No. WO 2008/077080, which documents are incorporated herein by reference in their entirety.

As illustrated in FIG. 1, for example, the surgical access device 100 can include an a pressurized fluid plenum 123 defined within the housing 120. In the illustrated embodiment, the plenum 123 is defined between the housing 120, a lower insert 130 and an upper insert 140. The plenum 123 is in fluid communication with at least one nozzle 128, and is configured to direct pressurized fluid in a substantially axial direction from the plenum 123 into a central lumen 118 of the access tube 110 to provide a constant gaseous seal around a surgical instrument inserted therethrough, and/or across the lumen 118 when an instrument is not inserted therethrough, for example.

Similarly, as illustrated, a recirculation chamber 121 can be defined in the access device 100, between the housing 120 and the lower insert 130. One or more sealing elements, such as resilient O-rings or the like, can be provided in seats 132, 142, which are formed respectively in each of the first and second inserts 130, 140. One or more openings 114 can be provided between the lumen 118 and the recirculation chamber 121 to allow gasses to pass into the recirculation chamber 121.

One or more additional chambers or other fluid conduits can further be provided, to facilitate fluid communication between a pressure-sensing device and/or a surgical insufflator, and the operative site. A fluid conduit can be formed within the wall of or on the inner or outer surfaces of the access tube 110. Alternatively, a separate tube can be passed though the lumen 118 for such purpose, if so desired. In still alternate embodiments, and as illustrated in the embodiment of FIGS. 2-6 for example, a pressure sensing and/or insufflation aperture 424 can simply be in fluid communication with the upper portion of the lumen 418.

As illustrated, a connection 125 is provided on the housing 120, and has at least one channel formed therein, in fluid communication with one of the aforementioned chambers and/or conduits. It is in fluid communication with such chambers and/or conduits by passages formed therein and in the housing 120. The connection 125 facilitates connection of multiple conduits, which may be embodied in a single set, to the access device 100 quickly and simply. The conduits, in-turn are connected to the appropriate equipment, including insufflation devices, recirculation devices and the like.

If desired, the housing 120 and the access tube 110 can be detachable from one another. The access tube 110 can be provided in assorted lengths and shapes, and with assorted features, as desired or required. Accordingly, a surgeon can decide before or during a procedure what length or diameter access tube 110 to use, and can attach it to the body 120 of the access device. Alternatively, a range of access devices of varying diameters, lengths and having varying features can be provided fully assembled to be available to the surgeon.

As set forth above, the illustrated cross-section of the access tube 110, which is taken in a plane parallel to the longitudinal axis 180 of the access device 100 is hyperbolic, and in three-dimensions is shaped as a hyperboloid of revolution. In cross-section, in a plane perpendicular to the central axis 180, for example, the cross-section can be circular, oval, elliptical or otherwise oblong in shape.

As illustrated in FIGS. 2-6, a surgical access device 200 in accordance with the invention can be adapted and configured for use with any desired tubular surgical access device, such as a flexible wound retractor 310 (FIG. 3), for example. Example wound retractors are set forth in U.S. Pat. Nos. 5,524,644, 3,347,226, 3,347,227, 5,159,921, 5,524, 644, 6,450,983, 6,254,534, 6,846,287, 5,672,168, 5,906,577, 6,142,936, 5,514,133, 7,238,154, 6,945,932, 6,908,430, 6,972,026, 5,741,298, or 6,945,932, which disclosures are incorporated herein by reference in their entirety.

In such embodiments, the wound retractor can be inserted through an incision formed in the patient, and secured by any suitable means. The body 120 can then be secured, such as by interference fit, friction fit, clamps, straps or otherwise secured to the proximal end of the wound retractor, for the purpose of providing insufflation, recirculation and/or filtration and/or fluidic sealing capability to prevent loss of abdominal pressure when insufflated, without introducing a mechanical seal.

Figure 4:
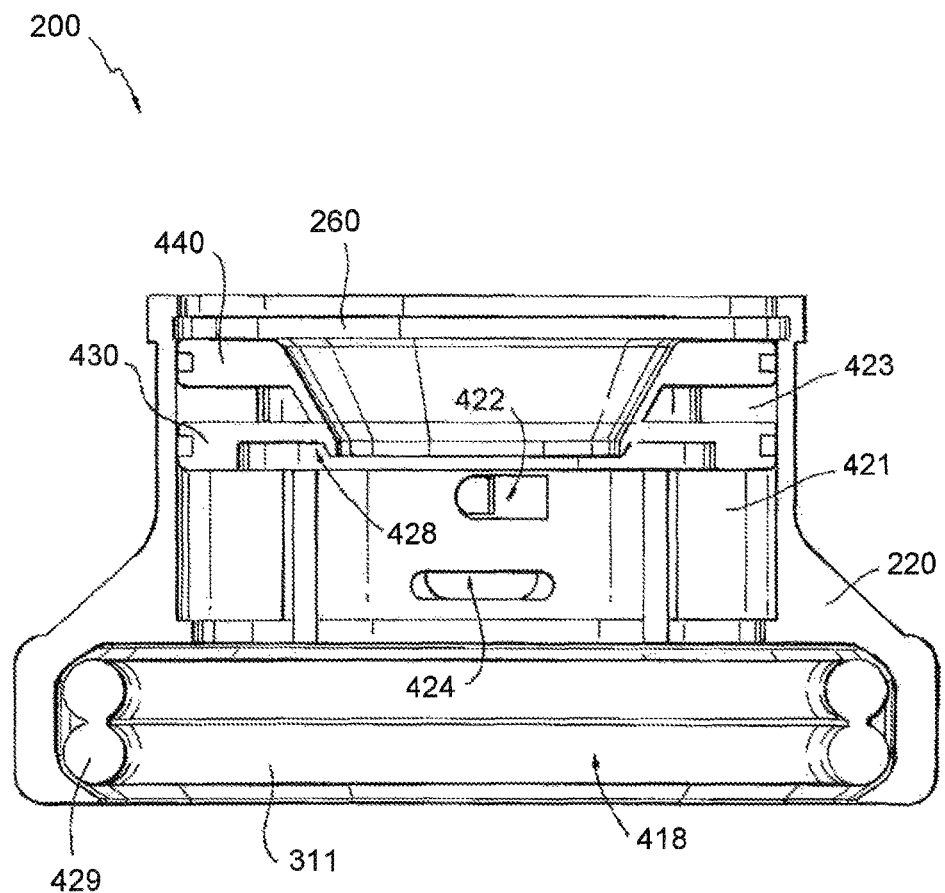
Figure 5A:
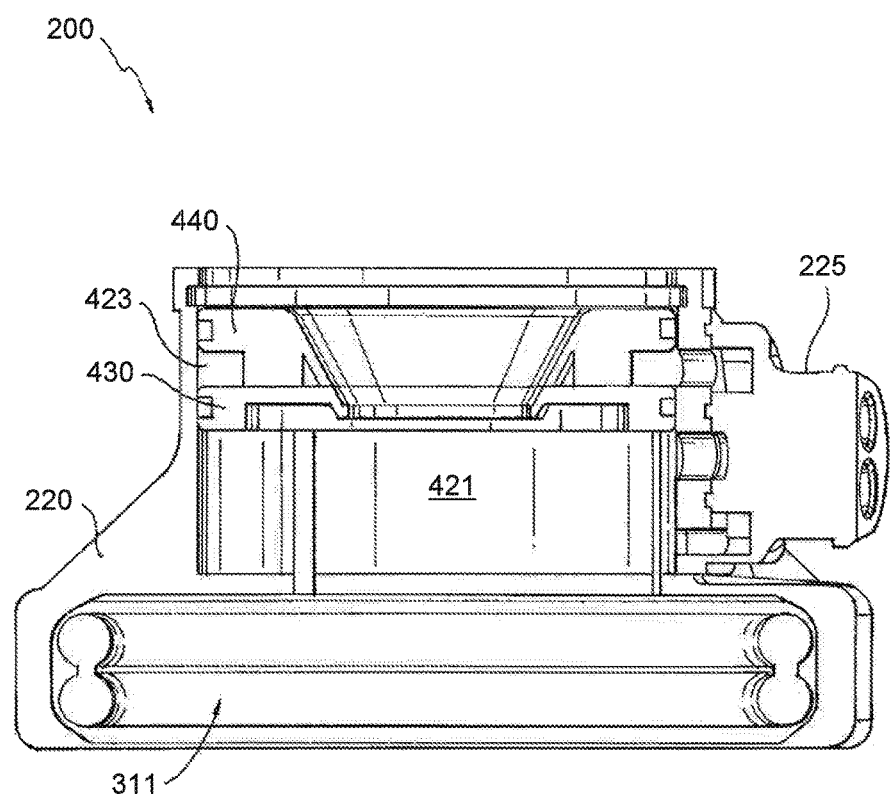
Figure 5B:
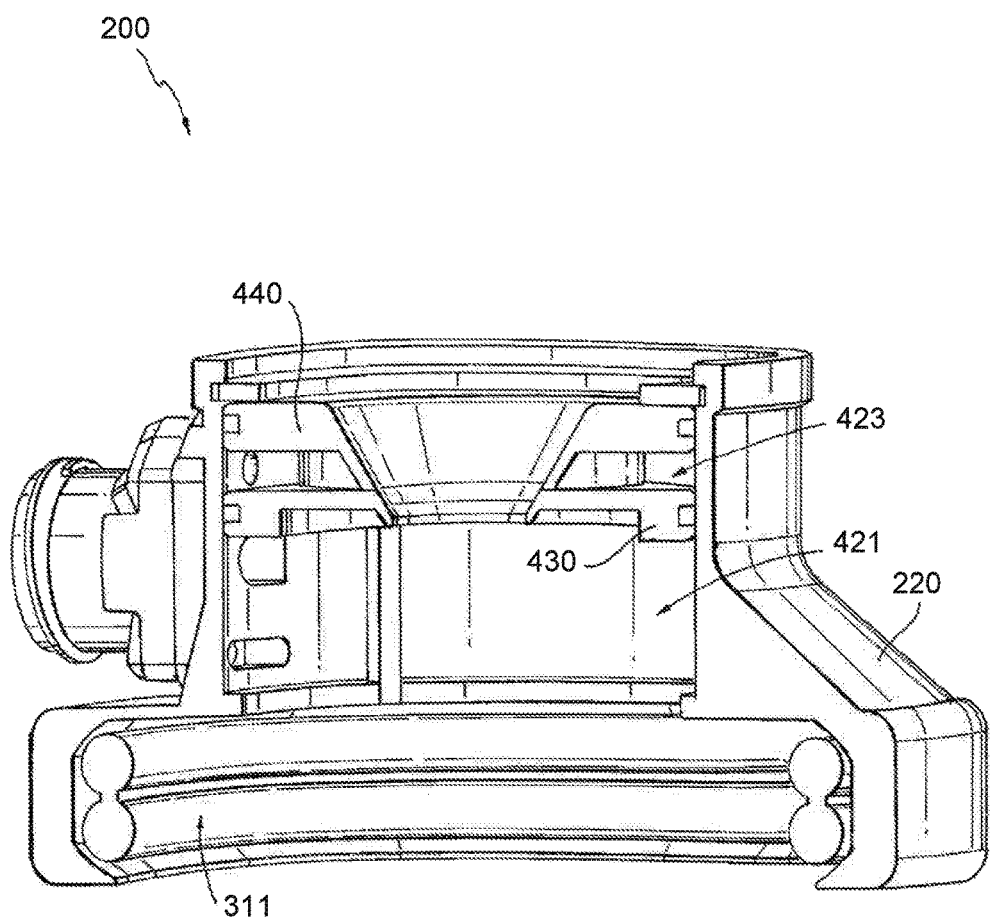
Figure 6:
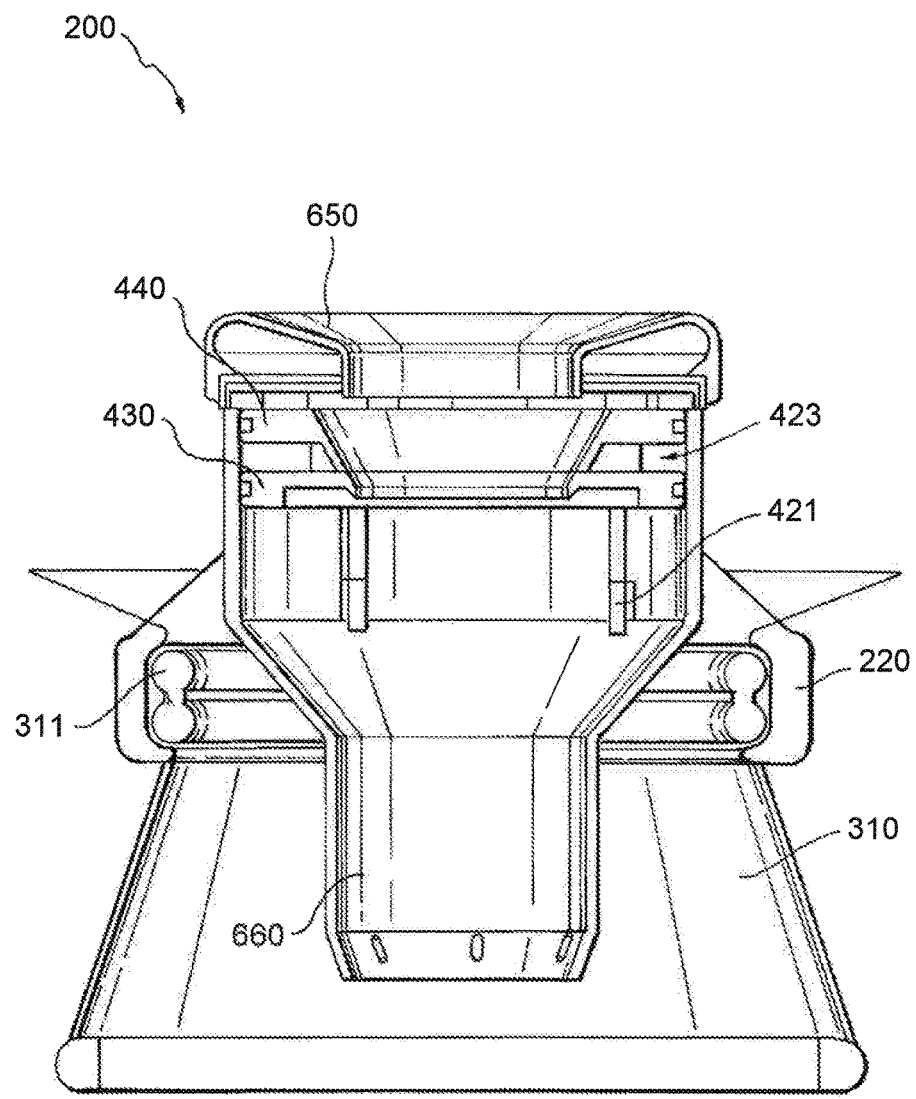
Figure 7:
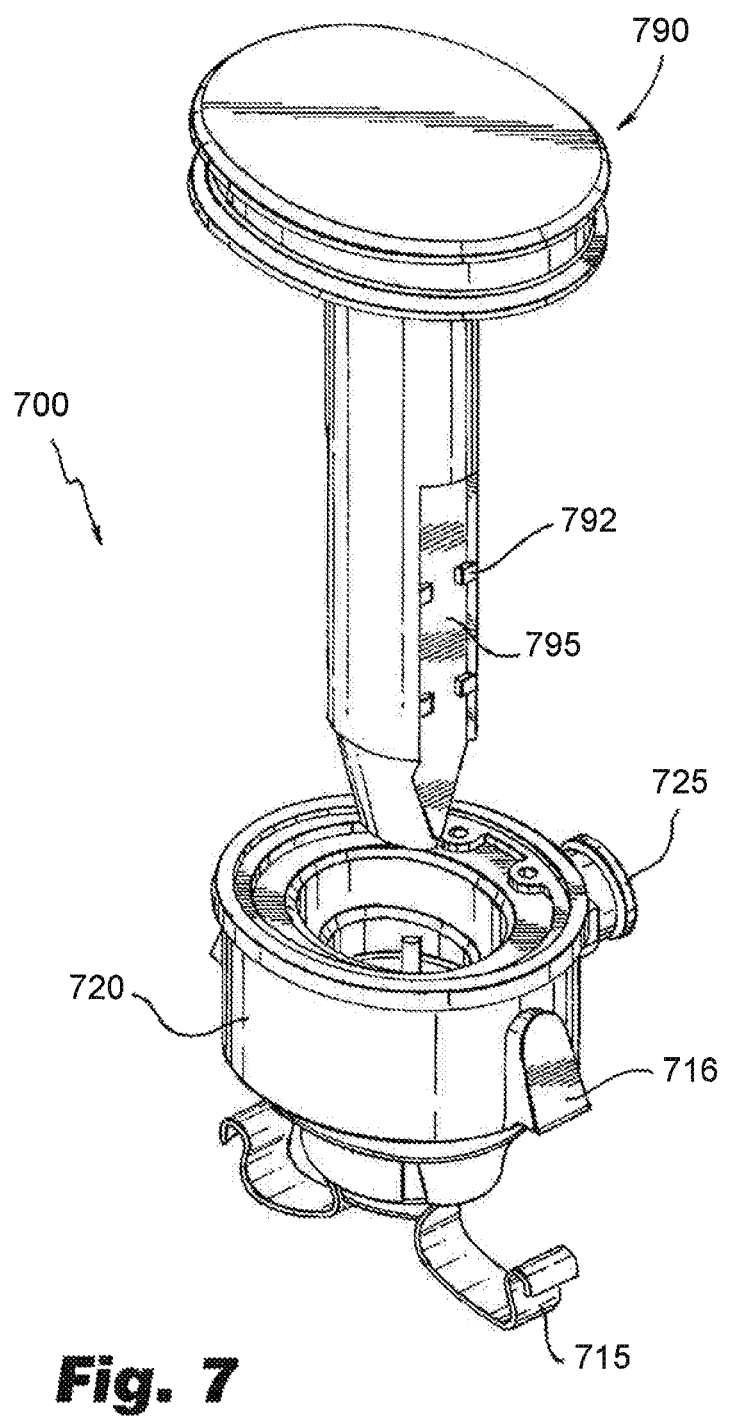
FIGS. 7-11 illustrate a third exemplary embodiment of a surgical access device in accordance with the invention, having opposed distal spring clips for engaging an abdominal wall of a patient.
Figure 8:
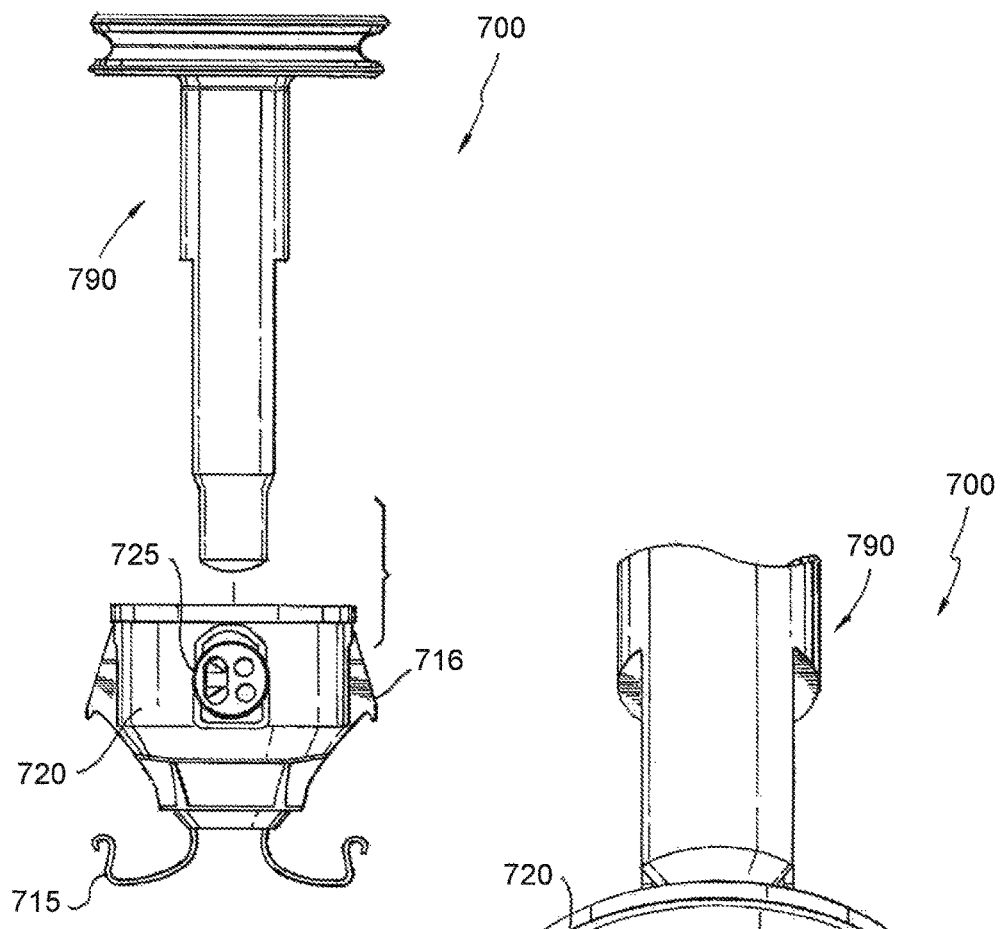
Figure 9:
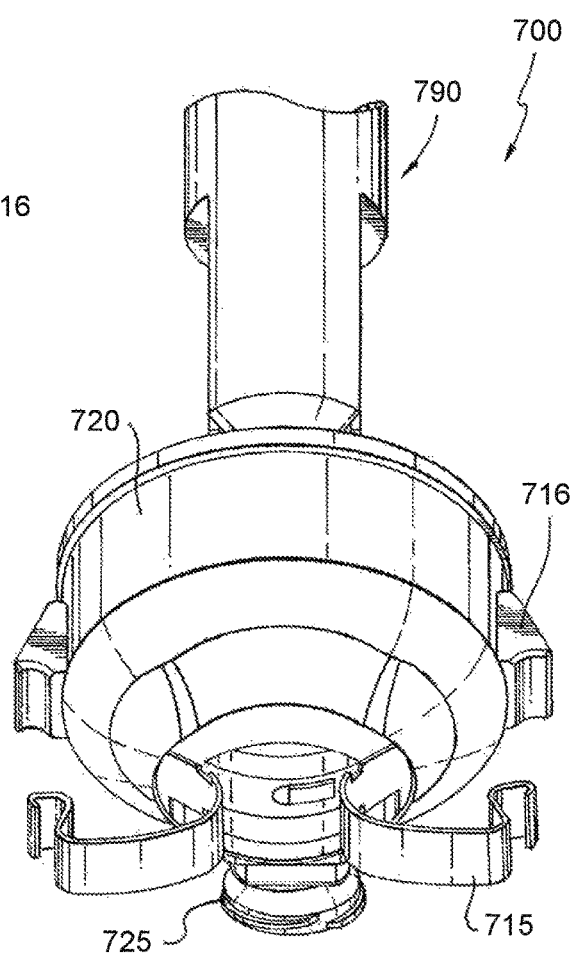
Figure 10:
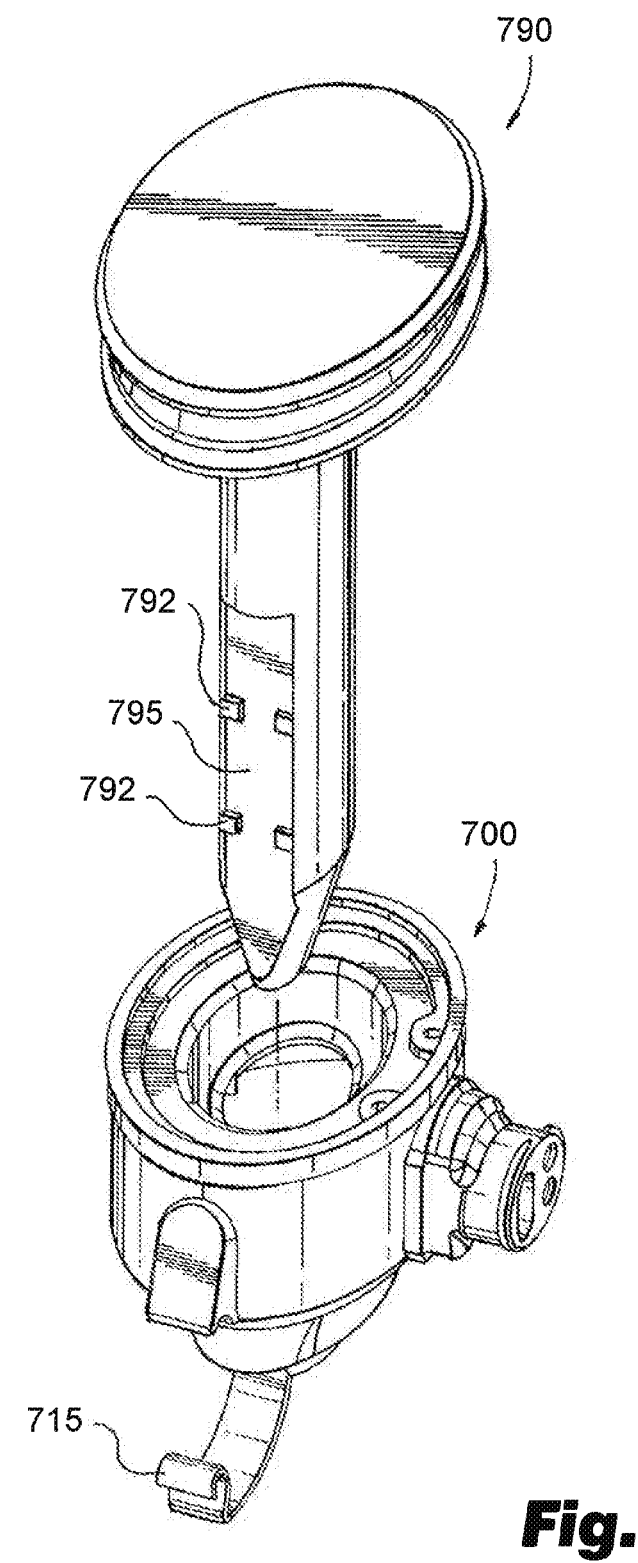
Figure 11:
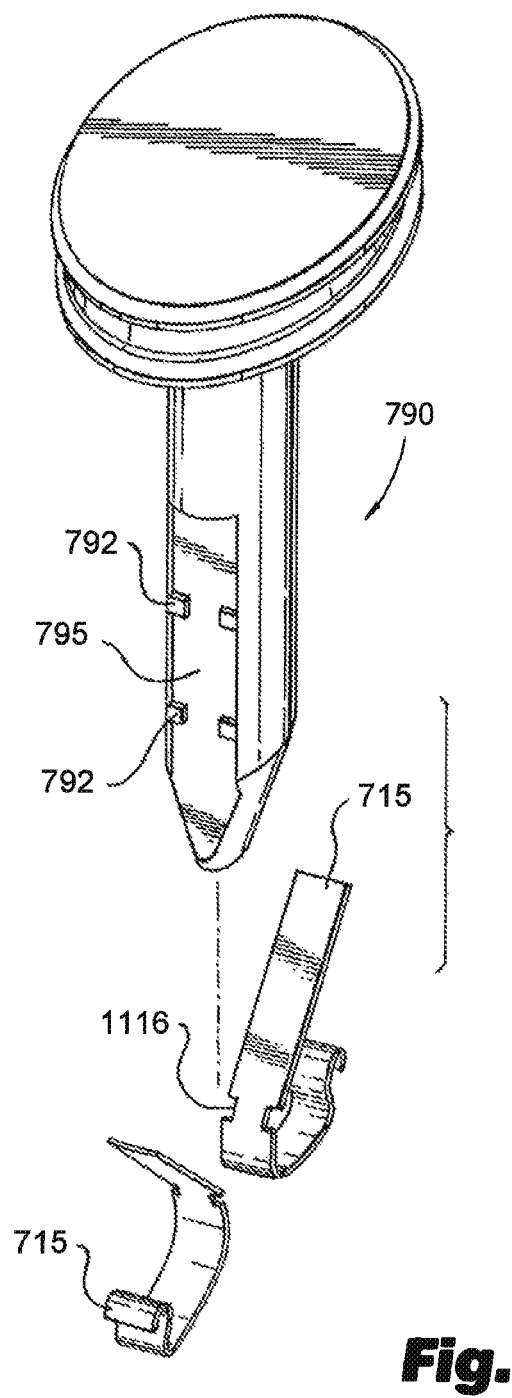

As illustrated, and as best seen in the cross-sectional views of FIGS. 4-6, a flexible wound retractor 300, which includes a sheath body 312, distal ring 313 and proximal ring 311 is seated in a distally positioned groove 429 in an expanded-diameter portion of the housing 220 of the surgical access device 200. The distal and proximal rings 311, 313 are typically made of a compliant material, such as a rubber, foam rubber or the like, and thus have an inherent shape and size. When the wound retractor 300 is inserted through an incision and secured to the patient, as by rolling or other technique, the housing 200 can be applied thereto, with the proximal ring 311 compressing initially during insertion, and then expanding to fit within the groove 429. The internal hoop stresses maintain the ring 311 and thus the retractor 300 within the groove 429, and inhibit unintentional removal therefrom.

Alternate connections between the wound retractor 310 and the housing 200 are conceived, including but not limited to use of clamp devices and the like, with the housing being seated at least partially within a lumen of the wound retractor, for example.

As with the surgical access device 100 of FIG. 1, the surgical access device 200 of FIG. 2-6 includes a housing 220, with a connector 225 extending therefrom. The internal components thereof, which will be explained in more detail below in connection with FIG. 4-6 are held within the housing by a retainer, which is embodied as a snap ring or "circlip" 260, which is used to maintain a relatively low profile, but other configurations are possible.

As best seen in the cross-sectional views of FIGS. 4-6, the surgical access device 200 is provided with a relatively low profile, allowing surgical instruments inserted therethrough to be less restricted in movement than with more conventional surgical access devices, as with the access device 100 of FIG. 1. The access device 200 includes a housing 220, adaptable with a flexible wound retractor 310 extending distally from the distal end of the housing 220.

In accordance with the invention, the access device 200 can include insufflation capability, can be adapted and configured to form a fluidic seal or barometric barrier around an instrument inserted therethrough and/or can be adapted to facilitate recirculation of insufflation gasses.

As illustrated the surgical access device 200 includes a pressurized fluid plenum 423 defined within the housing 220. In the illustrated embodiment, the plenum 423 is defined between the housing 220, a lower insert 430 and an upper insert 440. The plenum 423 is in fluid communication with at least one nozzle 428, and is configured to direct pressurized fluid in a substantially axial direction from the plenum 423 into a central lumen 418 of the wound retractor to provide a constant gaseous seal around a surgical instrument inserted therethrough, and/or across the lumen 418 when an instrument is not inserted therethrough, for example.

Similarly, as illustrated, a recirculation chamber 421 can be defined in the access device 200, between the housing 220 and the lower insert 430. One or more sealing elements, such as resilient O-rings or the like, can be provided in annular seats which are formed respectively in each of the first and second inserts 430, 440. An aperture 422 is provided in the housing 220 between the lumen 118 and the connector 225 to allow gasses to pass into a recirculation portion of a connected system.

One or more additional chambers or other fluid passageways or conduits 424 can further be provided, to facilitate fluid communication between a pressure-sensing device and/or a surgical insufflator, and the operative site. The fluid conduit can be formed within the wall of or on the inner or outer surfaces of a wound retractor connected thereto. Alternatively, a separate tube can be passed though the lumen 418 for such purpose, if so desired. In still alternate embodiments, and as illustrated in the embodiment of FIGS. 2-6 for example, a pressure sensing and/or insufflation aperture 424 can simply be in fluid communication with the upper portion of the lumen 418.

As illustrated, a connection 225 is provided on the housing 220, and has at least one channel formed therein, in fluid communication with one of the aforementioned chambers and/or conduits. It is in fluid communication with such chambers and/or conduits by passages formed therein and in the housing 220. The connection 225 facilitates connection of multiple conduits, which may be embodied in a single set, to the access device 200. The conduits, in-turn are connected to the appropriate equipment, including insufflation devices, recirculation devices and the like.

In cross-section, in a plane perpendicular to the central axis of the lumen 418, for example, the cross-section or the lumen portion of the housing 220 can be circular, oval, elliptical or otherwise oblong in shape.

As illustrated in the cross-sectional view of FIG. 6, a proximal cap 650 can be applied to the housing 220, and can incorporate sound attenuation features, such as sound absorbing materials or sound attenuation surface features to absorb, cancel or reduce sound created by fluid flowing through the lumen 418 of the access device. An internal skirt 660 is optionally provided, and is seated within the housing 220 and the lumen 418. Apertures can be formed in the housing portion of the skirt 660 to allow fluid to enter the recirculation plenum 421. Moreover, a tube or other passageway can be integrated into the skirt 660, in fluid communication with pressure sensing and/or insufflation components of attached systems, connected through the respective passageway of the connector 425.

FIGS. 7-11 illustrate a further surgical access device 700 in accordance with the invention, which includes a housing 720 with connector 725, with internal components that are substantially similar, and may include the same optional features to that of the foregoing embodiments, and which for simplicity will not be discussed in detail with respect to this embodiment. However, the surgical access device 700 includes a different anchoring mechanism than that of the foregoing embodiments. The surgical access device 700 includes spring anchors 715, which are provided in tracks formed in or alternatively on a surface of the housing 720, terminating in stops 716. The spring anchors are formed so as to secure the access device 700 to the abdominal wall of a patient, while preventing trauma thereto, and accordingly include a reverse bend at the distal end thereof. The spring anchors can be maintained within the housing 720, and not deployed, or can be deployed from a stowed position when the access device 700 is inserted. The spring anchors 715 can be formed of any suitable material including but not limited to stainless steel or shape-memory alloys.

In accordance with a preferred aspect, the access device 700 is provided with a compatible obturator 790, having opposed planar slots 795 with stubs 792 extending into the slots, offset from a bottom surface of the slots 795. As best seen in the exploded partial view of FIG. 11, notches 1116 are defines in the spring anchors 715. As the obturator 790 is advanced longitudinally, the stubs 792 pass through the notches 1116 and in combination with the slots 795 engage the spring anchors 715 and straighten them from their inherently curved configuration. The obturator 790 can be used to hold the spring anchors 715 in a straightened configuration during insertion of the access device 700, as well as during removal thereof from the patient.

Figure 12:
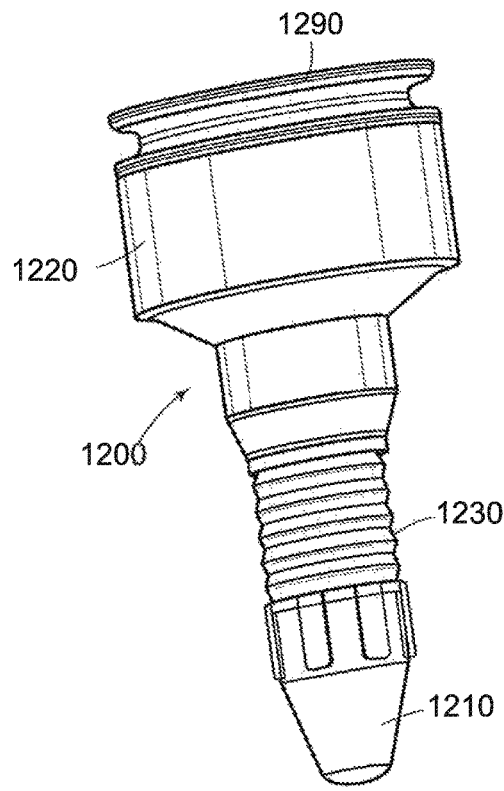
FIGS. 12 and 13 illustrate a fourth exemplary embodiment of a surgical access device in accordance with the invention, having expanding anchor elements at a distal end thereof, and a contractible body tube.
Figure 13:
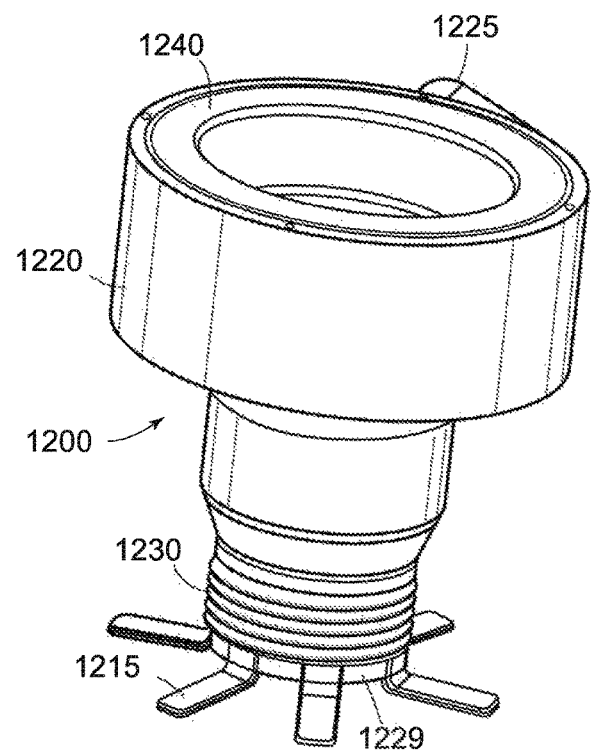
Figure 17:
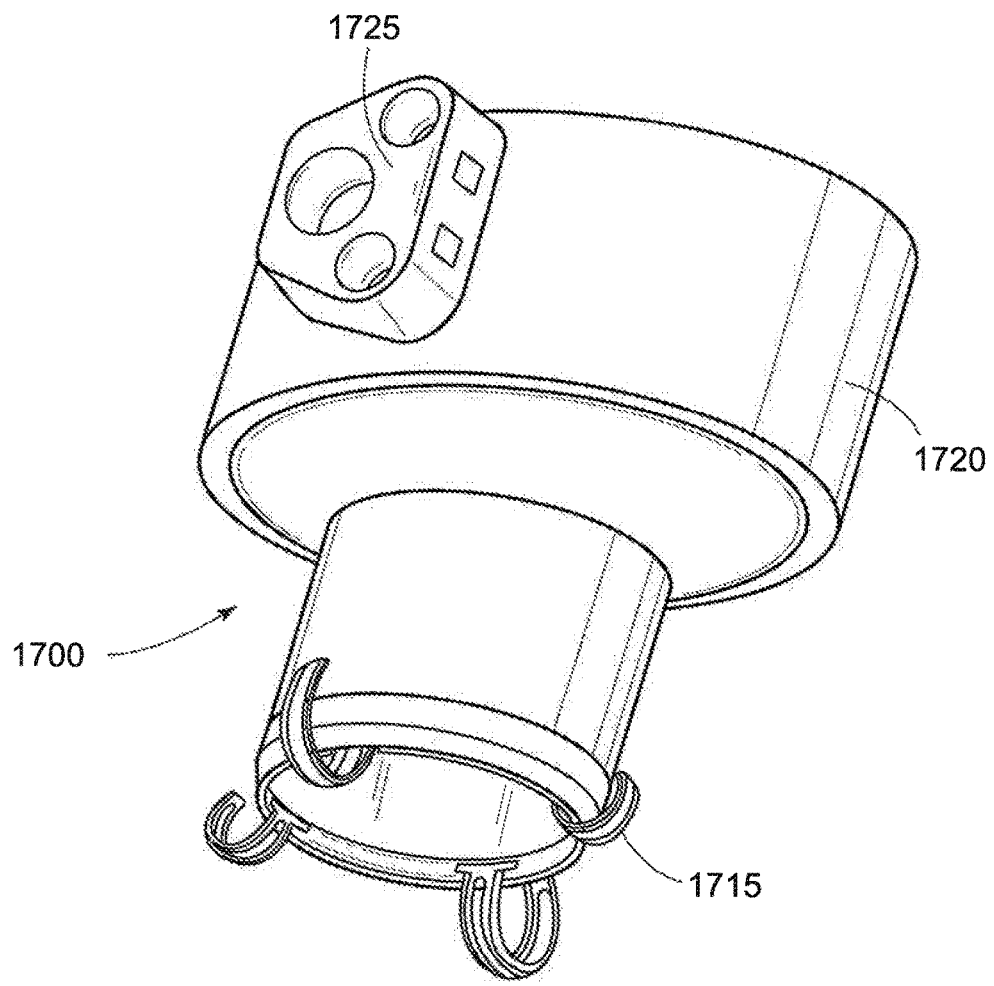

FIGS. 12-13 illustrate a further surgical access device 1200 in accordance with the invention, which includes a housing 1220 with connector 1225, with internal components that are substantially similar, and may include the same optional features to those of the foregoing embodiments, and which for simplicity will not be discussed in detail with respect to this embodiment.

The surgical access device 1200 includes still a different anchoring mechanism than that of the foregoing embodiments. The surgical access device 1200 includes spring anchors 1215, which are maintained during insertion of the access device 1200 by a distal end cap 1210, which can function as or be integrated with a surgical obturator 1290. When the access device 1200 is fully inserted into an incision formed in the abdominal wall of a patient, the cap 1210 is removed by urging the cap distally. The cap 1210 can be reapplied to the access device 1200 to allow for removal of the access device 1200.

The spring anchors 1215 can be formed of any suitable material, including shape memory alloys.

As illustrated, the body of the access device includes an adjustable bellows portion 1230 to aid in securing the access device 1200 to the abdominal wall. Following initial insertion of the access device 1200, the distal end portion 1229 of the body can be pulled proximally to effectively pinch the abdominal wall, securing the access device 1200 thereto. Such a connection can be accomplished by way of a spring-loaded component which is maintained in an extended configuration during insertion of an obturator 1290, or alternatively a cable arrangement attached to the distal end portion 1229 and pulled proximally.

FIGS. 14-16 illustrate a further surgical access device 1400 in accordance with the invention, which includes a housing 1420 with connector 1425, with internal components that are substantially similar, and may include the same optional features to those of the foregoing embodiments, and which for simplicity will not be discussed in detail with respect to this embodiment.

The surgical access device 1400 includes distal anchor elements 1415, which can be formed of any suitable material, including but not limited to stainless steel or a shape memory alloy, for example. The anchor elements 1415 are maintained in a straight orientation (FIG. 14), when engaged with a distal end portion 1410 of a surgical obturator 1490. As best seen in FIG. 15, the track 1417 is integrated with the anchor elements 1415 and is adapted to engage one or more protrusions on the obturator 1490 to maintain the anchor elements 1415 in the desired position. A frame 1416 of the anchor elements 1415 defines the overall shape, and terminates as pivots 1419. The frame 1416 can be provided with a coating 1418, which can be made of a cushioning material to minimize trauma to the patient and/or to enhance anchoring of the access device 1400. The cushioning material can be silicone rubber for example, but can be another suitable material, and can extend into a web 1481 define within the frame 1416, effectively increasing the surface area of the anchor element 1415.

FIG. 16 shows the access device 1400 with the obturator 1490 removed therefrom.

FIGS. 17-26 illustrate a further embodiment of a surgical access device 1700 in accordance with the invention, and detailed views of anchoring elements 1715 thereof. The surgical access device is similar to the embodiment of FIGS. 14-16, and includes a housing 1720 with internal components as set forth above, a connection element 1725 and anchor elements 1715.

Figure 18:
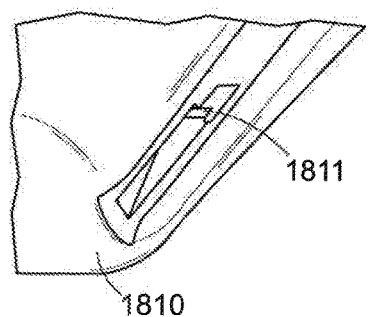
Figure 19:
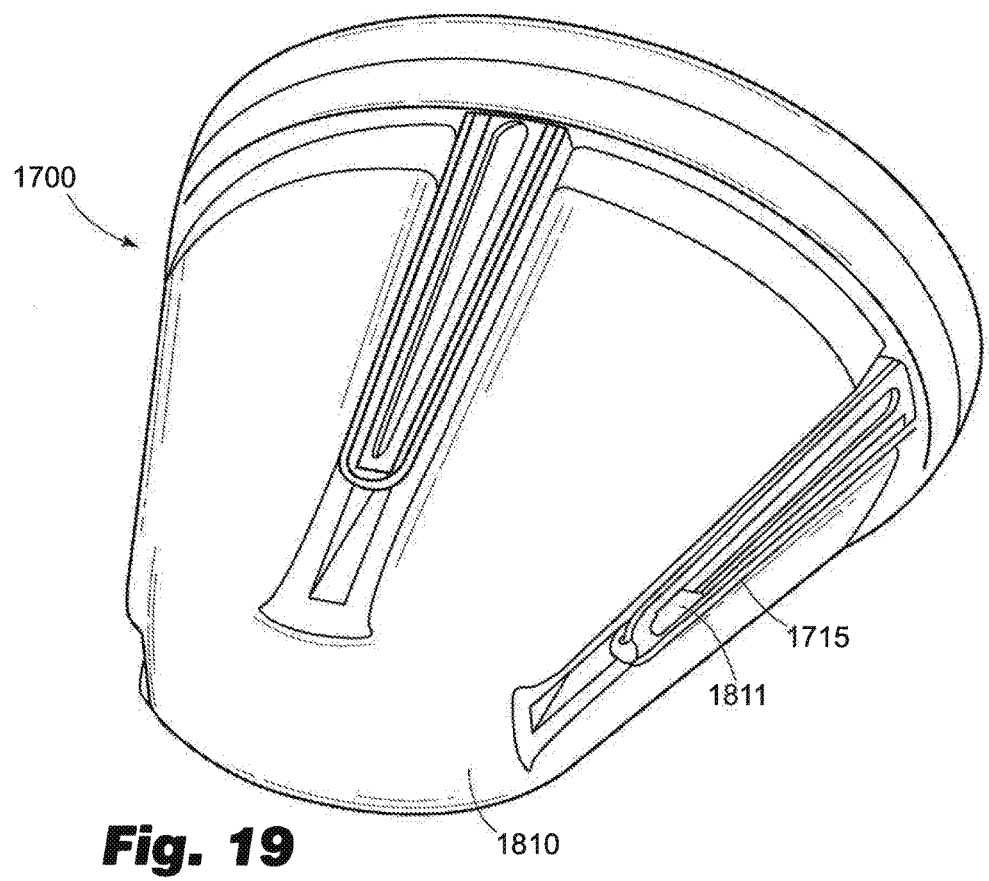
Figure 20:
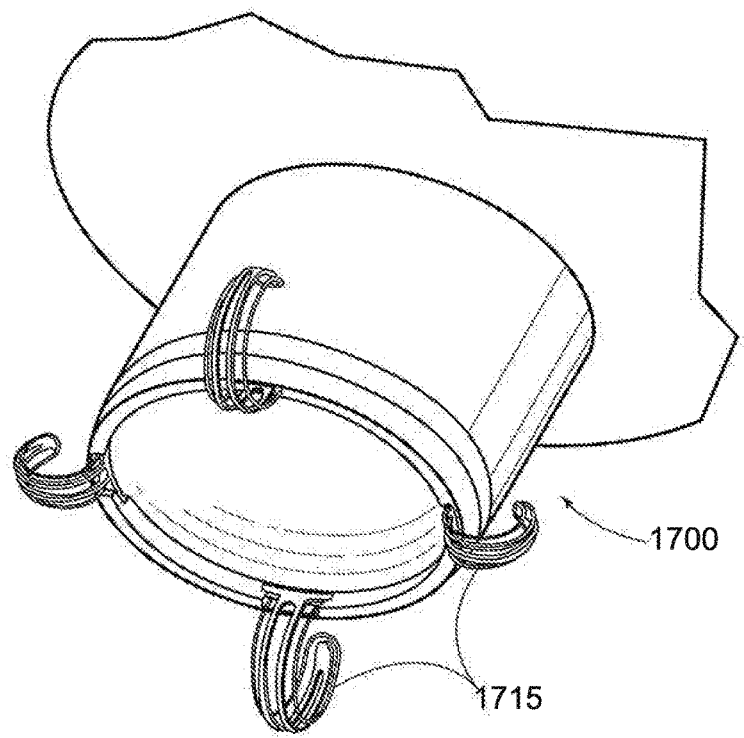

As shown in FIGS. 18 and 19, an obturator for use with the access device 1700 includes a distal end portion 1810, which engages the anchor elements 1715 by way of articulating hooks 1811. Upon insertion, the articulating hooks 1811. The anchor elements 1715 are maintained in a straight position during insertion and are released when the access device 1700 is fully inserted through the abdominal wall of the patient.

As with the access device 1400 of FIGS. 14-16, the access device 1700 includes a plurality of circumferentially arranged anchors 1715, which are formed of a material such but not limited to stainless steel or shape-memory alloys. Alternatively, with this or other embodiments described herein, resilient polymeric materials can be used. Optional features including coverings, a web element or the like can be applied to advantageous effect.

Figure 21:
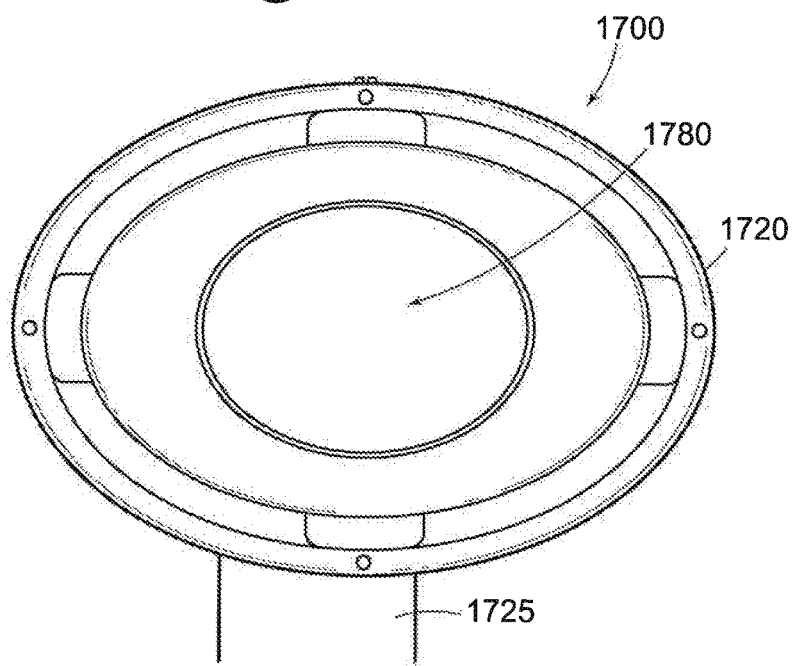
Figure 22:
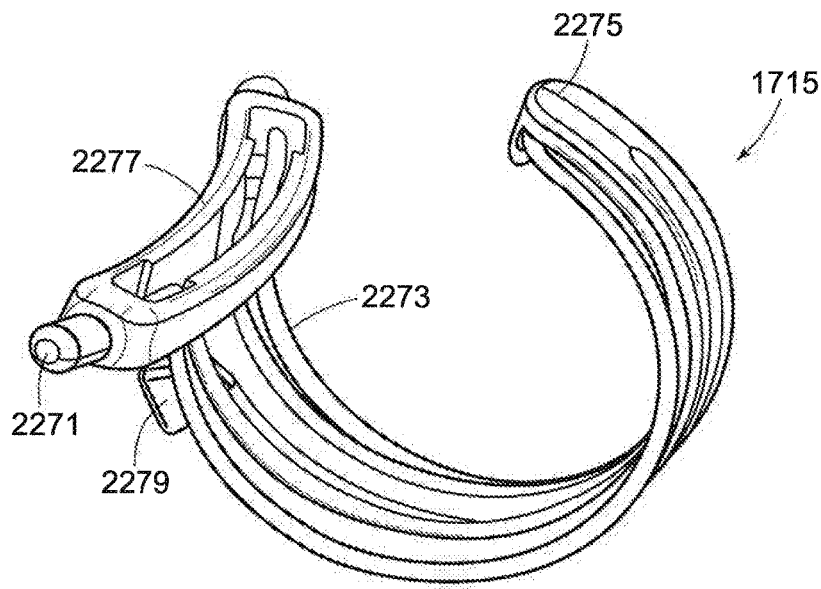
Figure 23:
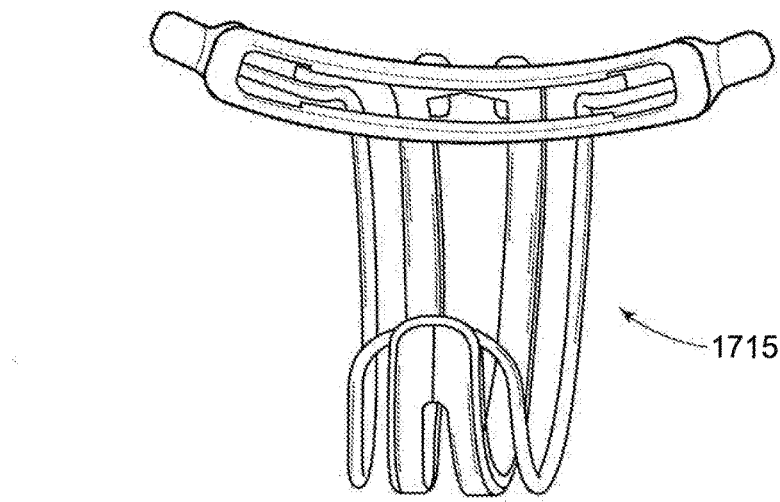

FIG. 21 is a top view of the surgical access device 1700, which illustrates an overall cross-sectional shape and lumen shaped substantially as an ellipse. As set forth above, alternate shapes are possible, including but not limited to circular, cat-eye shape or oblong of another configuration.

As best seen in FIGS. 22-26, the anchors 1715 include a main body 2275, spring elements 2273, pins 2271 extending from the body 2275, one or more struts 2277. The body 2275 can be formed of any suitable material, including but not limited to polymeric materials. The tendency of the anchors 1715 to curve is imparted in the illustrated embodiment by way of the spring elements 2273, which as with foregoing embodiments can be formed of any suitable material including but not limited to polymeric materials and metals, including shape memory alloys.

The pins 2271 are provided to secure the anchors 1715 to the body 1720 of the surgical access device 1700. Further protrusions 2279 can be provided on the anchors 1715 to additionally secure the anchors 1715 to the body 1720.

Figure 27:
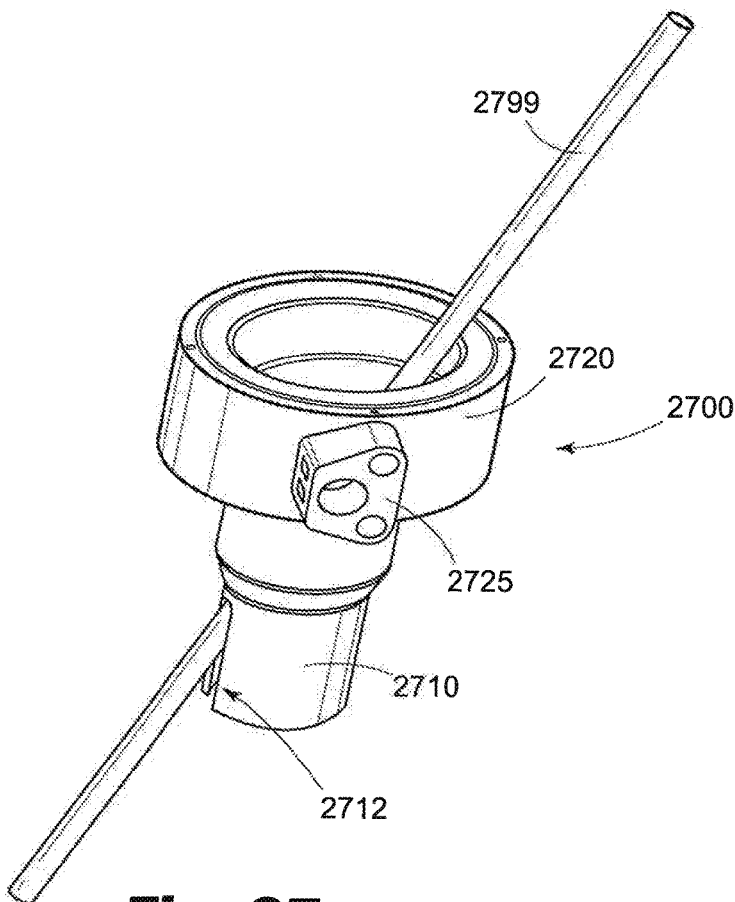
FIGS. 27-29 illustrate a seventh exemplary embodiment of a surgical access device in accordance with the invention having at least one slot formed in a distal body portion thereof to enhance a range of motion of a surgical instrument inserted therethrough.
Figure 28:
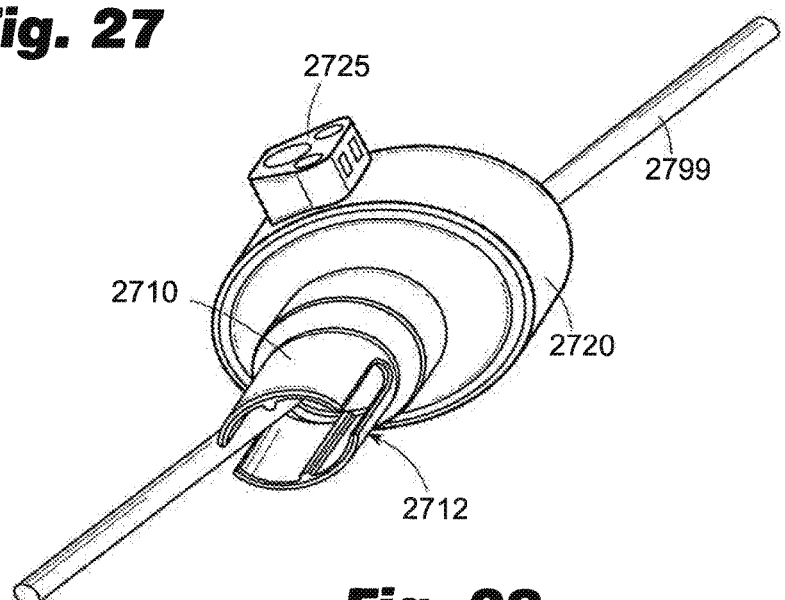
Figure 29:
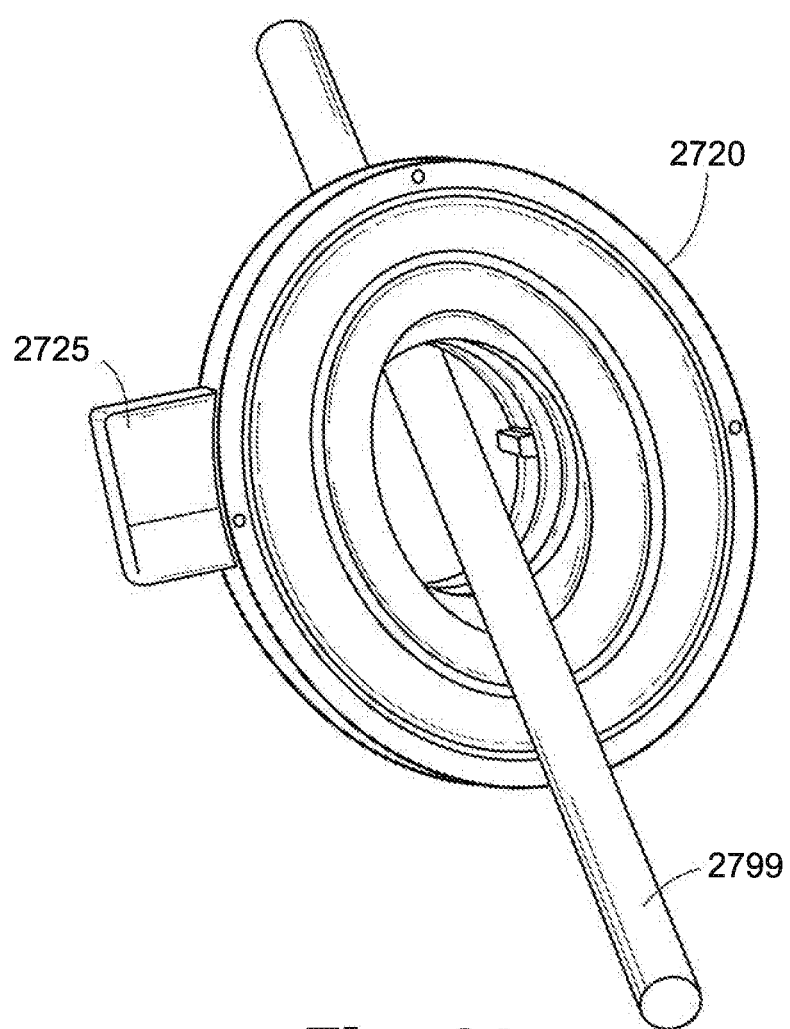
Figure 30:
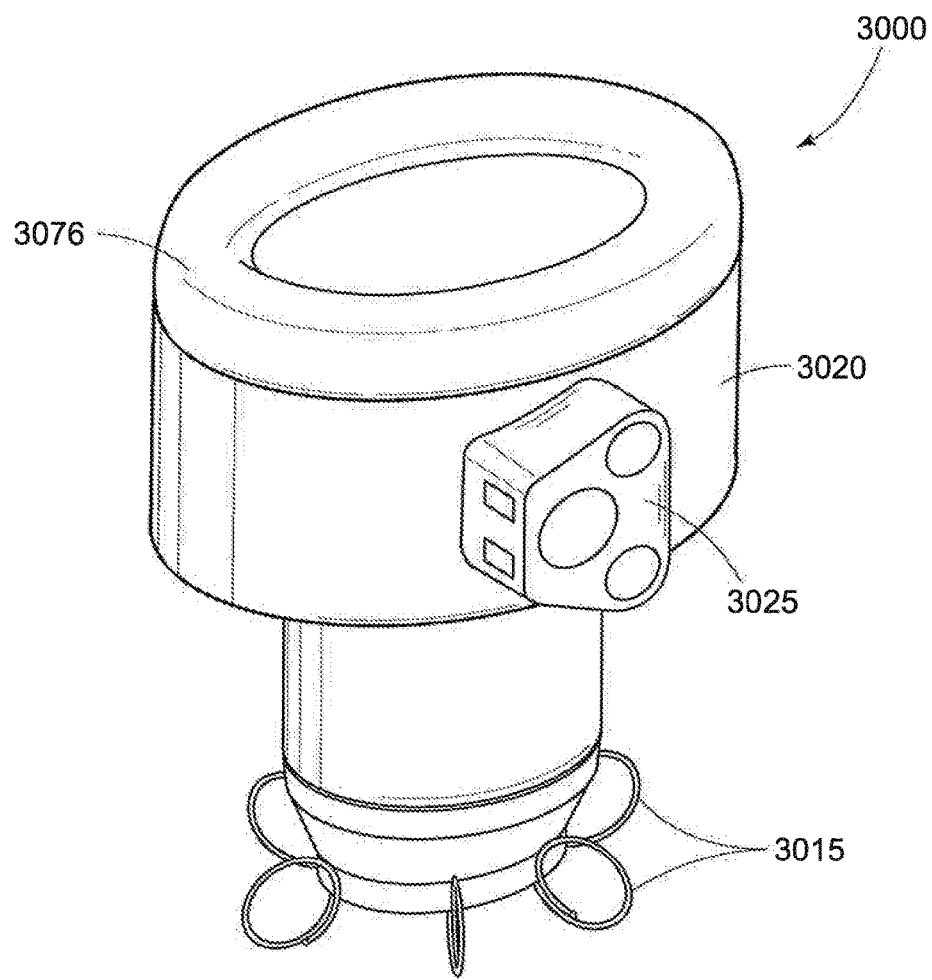
FIGS. 30-33 illustrate an eighth exemplary embodiment of a surgical access device according to the invention, having distal coiled anchor elements.
Figure 32:
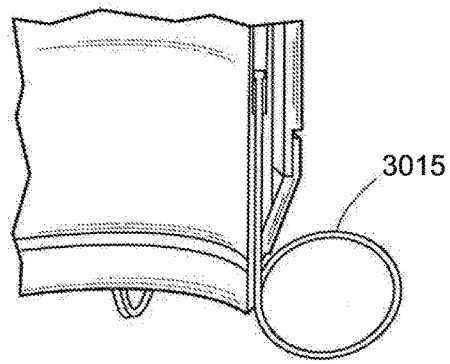
Figure 31:
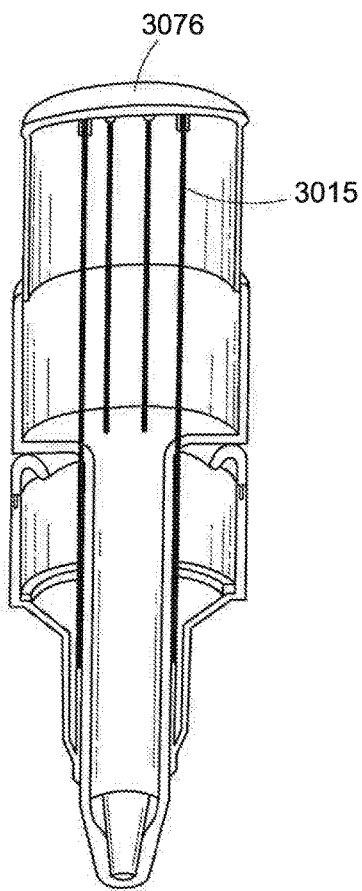
Figure 33:
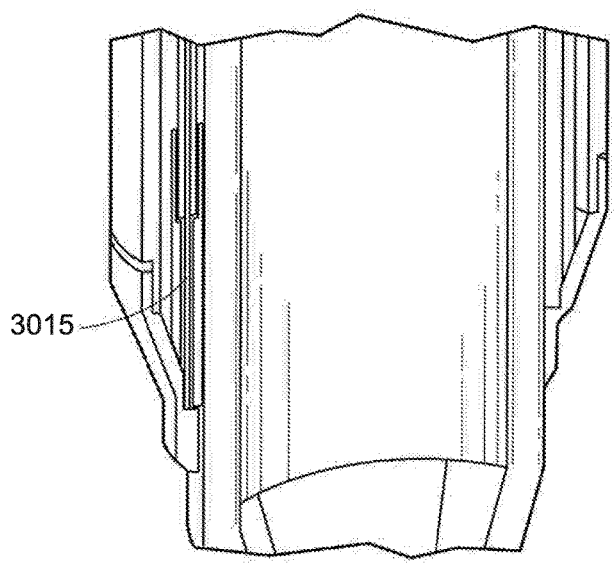

FIGS. 27-29 illustrate an access device 2700 which includes a slot 2712 formed in a distal end portion 2710 of the body 2720 thereof. This feature can be applied to any other embodiment set forth herein, which includes an elongated body. The slot allows for extended range of motion of a surgical instrument 2799 inserted through the access device 2700. As with the above-described embodiments, the housing 2720 includes a connection 2725. As best seen in FIGS. 28-29, the cross-sectional shape is substantially elliptical, but alternatively can have another shape, as mentioned above.

FIGS. 30-33 illustrate a further embodiment of a surgical access device 3000 in accordance with the invention, having a housing 3020 with connection 3025. The surgical access device 3000 includes circularly coiled anchor elements 3015 circumferentially arranged in a distal end portion thereof. An axially movable actuator 3076 is provided, in connection with the anchor elements 3015, which when contracted are housed within the body 3020 of the access device 3000. When the actuator 3076 is urged distally, the anchor elements 3015 extend from the distal end of the housing 3020, and coil in radial planes, perpendicular to a longitudinal axis of the access device 3000. When deployed, the anchor elements 3015 abut the abdominal wall, thereby helping anchor the access device 3000. As with foregoing embodiments, the anchor elements 3015 can be formed of a spring material, which can be, for example, a resilient polymeric material, or a metal such as stainless steel or a shape memory alloy.

Figure 34:
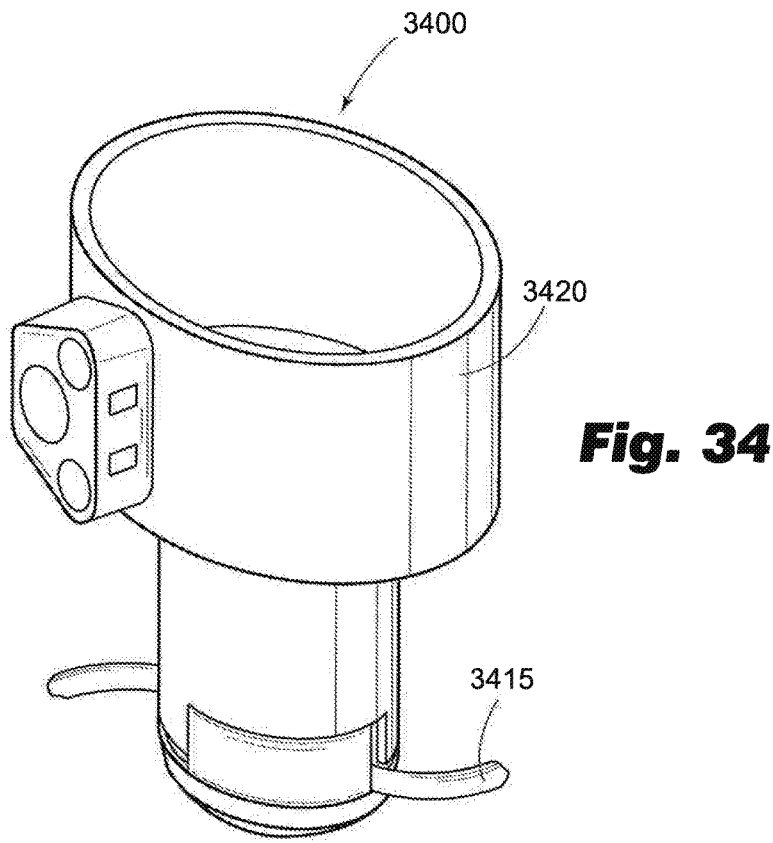
FIGS. 34-35 illustrate a surgical access device with radially deployable anchor elements actuated by one or more shafts.
Figure 35:
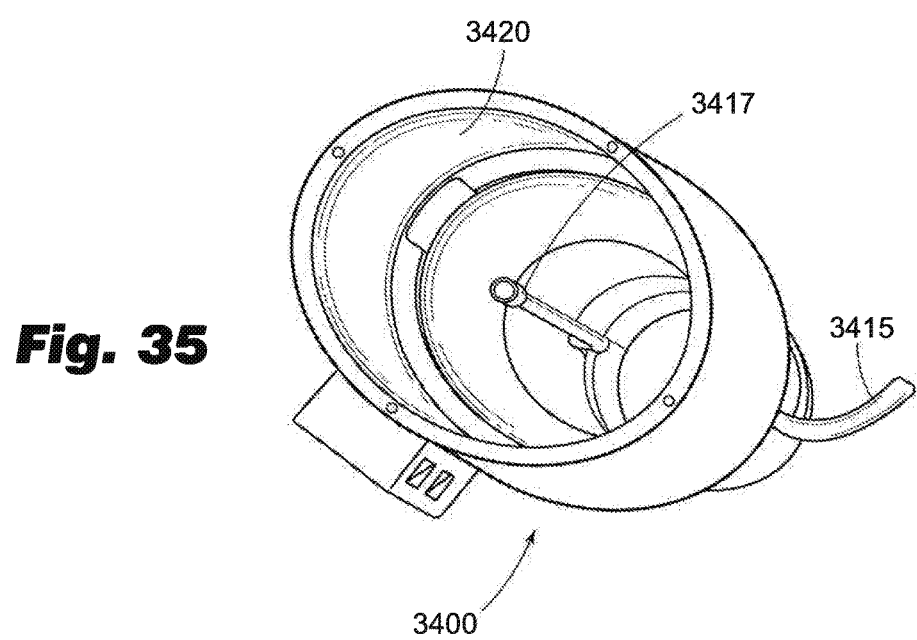
Figure 36:
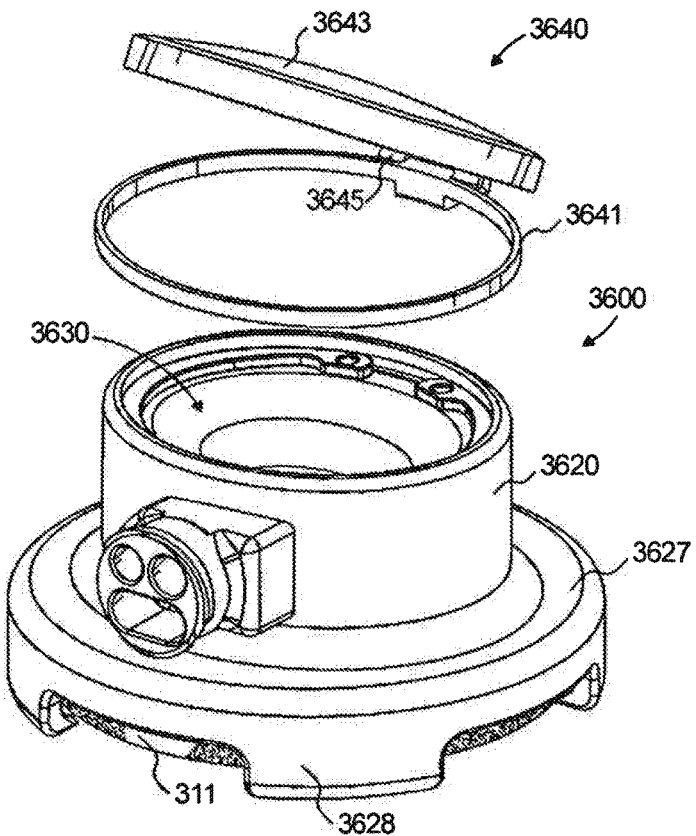
FIGS. 36-41 illustrate a surgical access device in accordance with a further embodiment of the invention, which can be provided with a proximal end cap.
Figure 37:
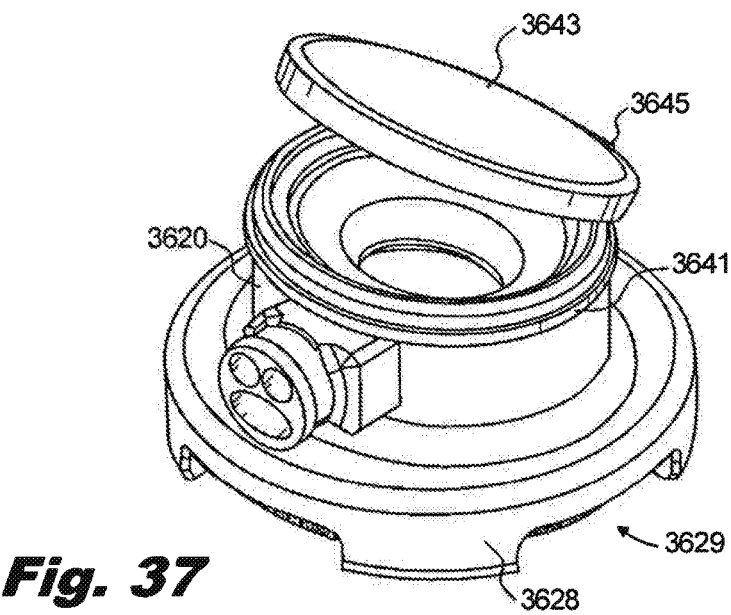
Figure 38:
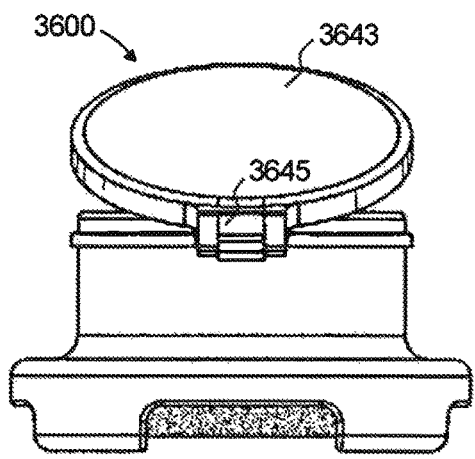
Figure 39:
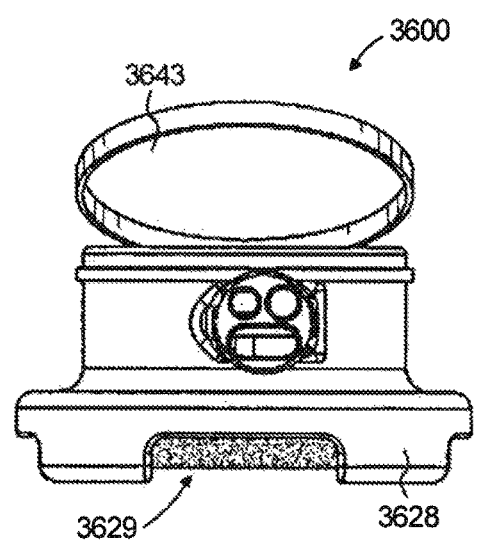
Figure 40:
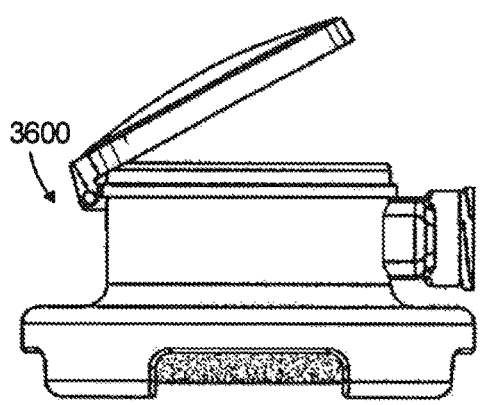
Figure 41:
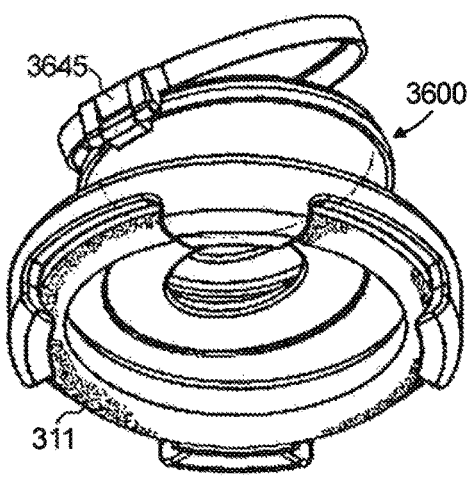
Figure 42:
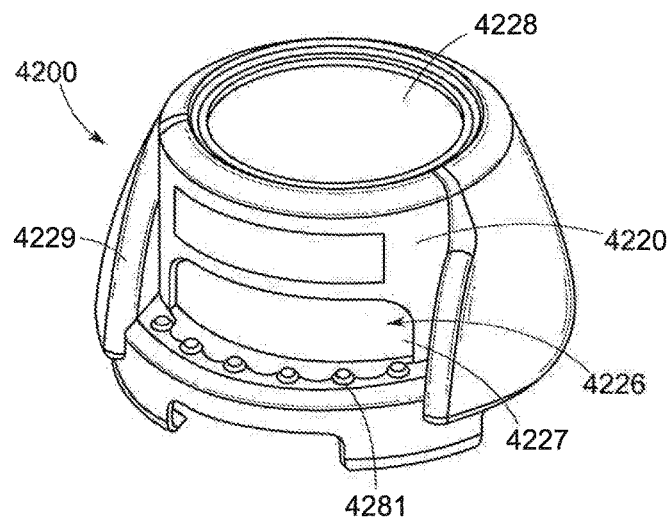
Figure 43:
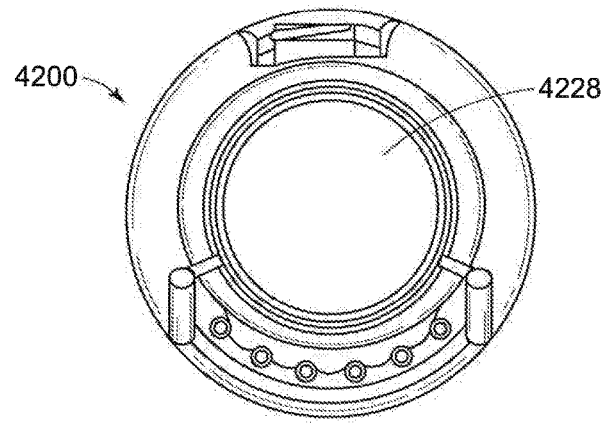
Figure 44:
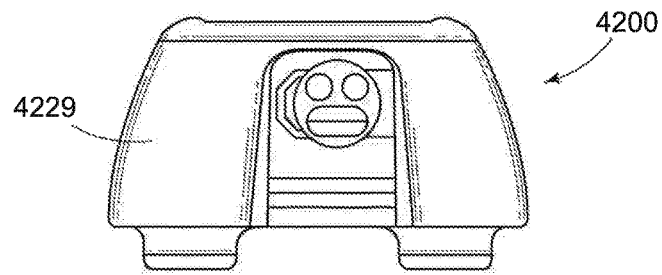
Figure 45:
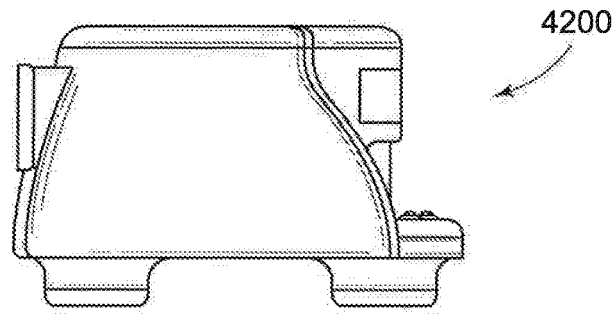
Figure 46:
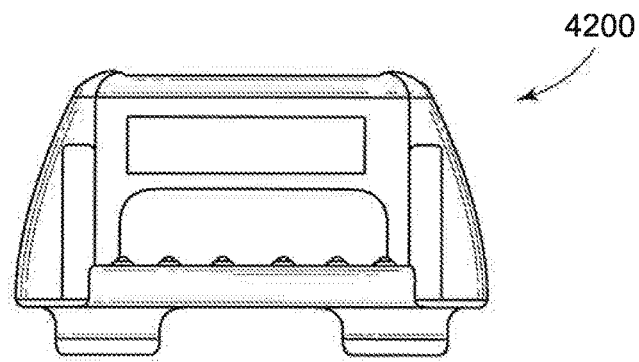
Figure 47:
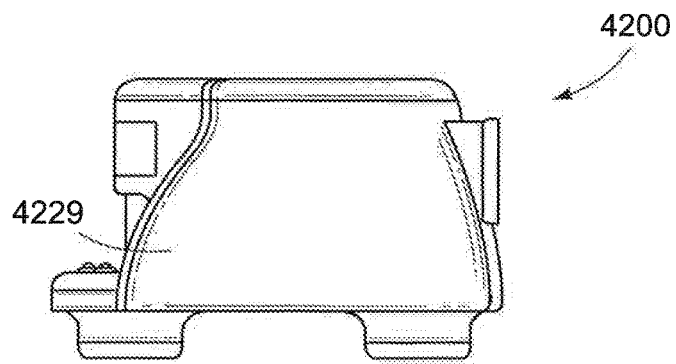

FIGS. 34 and 35 illustrate a surgical access device 3400 having yet a further alternative anchoring mechanism, with radially deployable anchor elements 3415, actuated by one or more shafts 3417 provided in a housing 3420 thereof. When the access device is inserted through an incision, the anchor elements 3415 are deployed to anchor the access device 3400 to the abdominal wall of the patient.

FIGS. 36-41 illustrate a surgical access device 3600 similar to the embodiment illustrated in FIGS. 2-5B. The surgical access device 3600 includes an upper housing portion 3620 and a distal, or lower, housing portion 3627. The lower housing portion 3627 includes a discontinuous bottom end, with extensions 3628, being interrupted by openings 3629. Such an arrangement facilitates connection with and removal from a detachable body tube, such as the flexible proximal ring 311 of a flexible wound retractor. A nozzle assembly 3630 is provided in the housing 3620.

A lid assembly 3640 is optionally provided, and as embodied includes an engagement portion 3641, a lid portion 3643 and a hinge 3645 arranged therebetween. The engagement portion 3641, as embodied, is a ring that surrounds the housing 3620. However, it is to be understood that this element need not be limited to such a configuration. The engagement portion 3641 can be connected to the housing 3620 by friction fit, adhesive, bonding such as solvent, friction welding or ultrasonic welding, for example.

FIGS. 42-50 illustrate a further embodiment of a surgical access device 4200 in accordance with the invention. The surgical access device 4200 includes a housing 4220, and a cover 4229 with an optional removable lid 4228. The cover 4229 is preferably fit over the body 4220 and serves to reduce sound from fluid flowing through the access device 4200 to an observer, for example, in the operating room during use of device 4200. As such, the cover 4229 is, in accordance with one aspect, formed of a sound-absorbing material, at least in part. Further, the cover 4229 can be removed quickly during a surgical procedure if increased access to a surgical site is required.

The housing 4220 includes, defined therein, a side access port 4226, which can be provided with a pivotable or flexible door 4227 to reduce noise coming through the side access port 4226 when not in use. When desired, surgical instruments or accessories, such as sutures can be inserted through the port 4226, or specimens can be removed therethrough. The configuration of a nozzles, provided in the surgical access device 4200 permits openings to the side of the housing 4220, as with the side access port 4226. In such arrangements, a pressure barrier is formed below the port 4226, and as such, the port 4226 experiences lower pressure than those experienced in the abdomen under insufflation. Accordingly, insufflation gasses remain in the abdominal cavity, or are recirculated through the surgical access device 4200.

Additionally, a plurality of protrusions 4281 can be provided adjacent to the side access port 4226. The protrusions serve to hold and inhibit sliding of surgical instruments inserted through the port 4226, and also serve as fulcrums for applying leverage to surgical instruments inserted through the port 4226.

As can be seen in the view of FIG. 48, a plurality of standoffs 4281 can be provided to maintain a positioning of a nozzle insert in the housing 4220. In the exploded view of FIG. 50, an exemplary connection arrangement between the cover 4229 and lid 4228 is illustrated, whereby studs 4298 extend from the lid 4228, and engage corresponding apertures 4299 in the cover 4229. A circlip 260 can be provided for securing a nozzle insert within the housing 4220.

Figure 51:
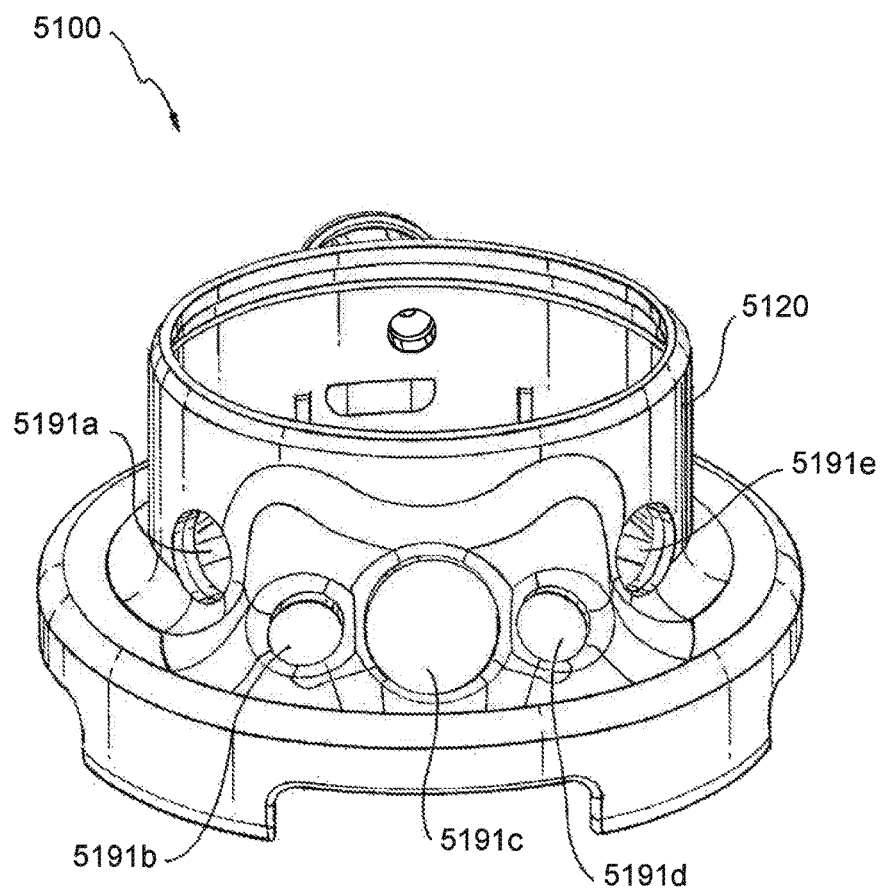
FIG. 51 illustrates still a further surgical access device in accordance with the invention having a plurality of side-access ports.
Figure 52:
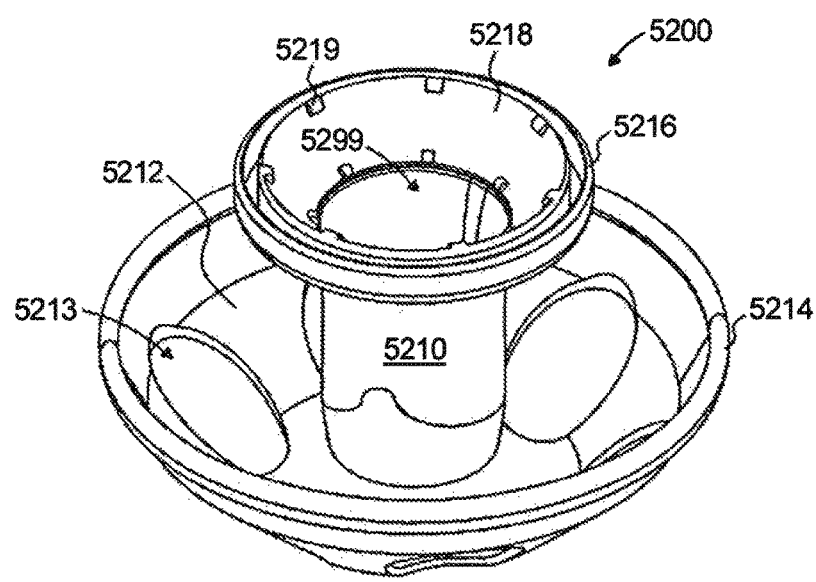
FIGS. 52-57 illustrate a wound protector compatible with the surgical access devices, of the invention having an anchor portion, central tubular structure and curved sealing members.
Figure 53:
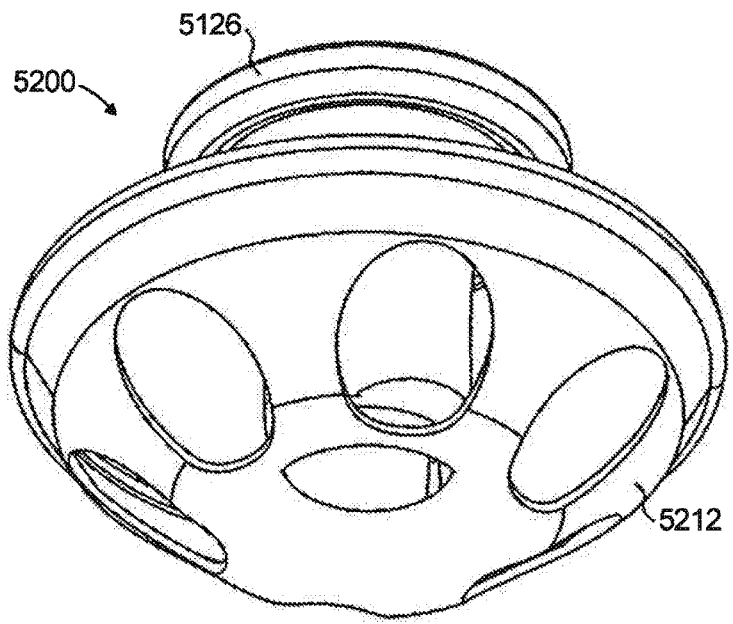

FIG. 51 illustrates a further surgical access device 5100, which, similar to the embodiment of FIGS. 42-50, is provided with side access ports 5191*a-e* in the housing 5120 thereof. The surgical access device 5100 is not illustrated with a nozzle insert for simplicity of illustration, but one would be provided, as with other embodiments set forth herein. The side access ports 5191*a-e* permit insertion of multiple instruments through a surgical incision, while maintaining positioning thereof in respective ports. As set forth above, a pressure barrier is formed below the ports 5191*a-e*, and therefore no mechanical seals are required. In accordance with the invention, one or more ports 5191*a-c* can be used with an endoscope, and such an arrangement can also facilitate use with robotic surgical systems, by defining secure positions in which instruments can be placed, relative to a patient's anatomy.

FIG. 52-57 illustrate a wound protector 5200, compatible with the foregoing surgical access devices. The wound protector 5200 includes a proximal end portion 5216, a central tubular structure 5210, and a distal anchor portion 5214. The anchor portion 5214 is supported by the central tubular structure 5210 by a web 5212. Apertures 5213 can be defined in the web 5212 to facilitate manipulation of the wound protector 5200 and material reduction. The wound protector 5200 is preferably molded of an elastomeric material, but can optionally be provided with an internal structure of a shape-memory alloy, if desired.

The proximal end portion 5216 includes an upper surface 5218 with standoffs 5219, which, as illustrated are configured to directly interface with nozzle components for forming pressure barriers, such as those described herein. As such, the surface 5218 can partially define a chamber or plenum, such as a return plenum for recirculation capability.

Figure 54:
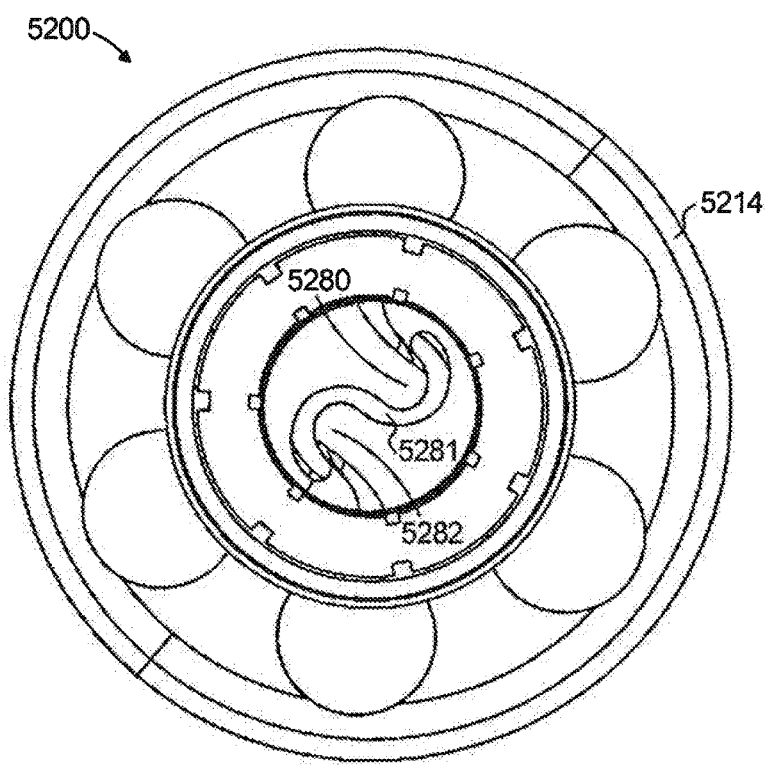
Figure 55:
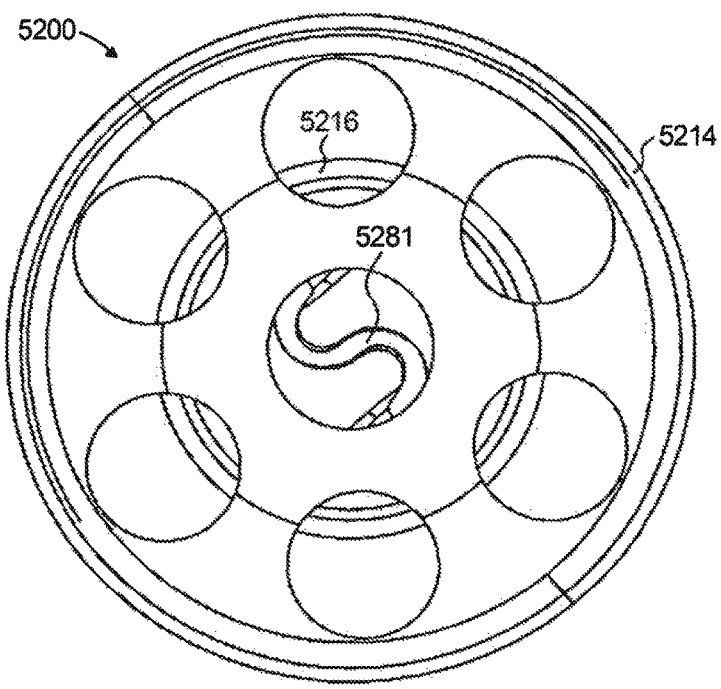
Figure 56:
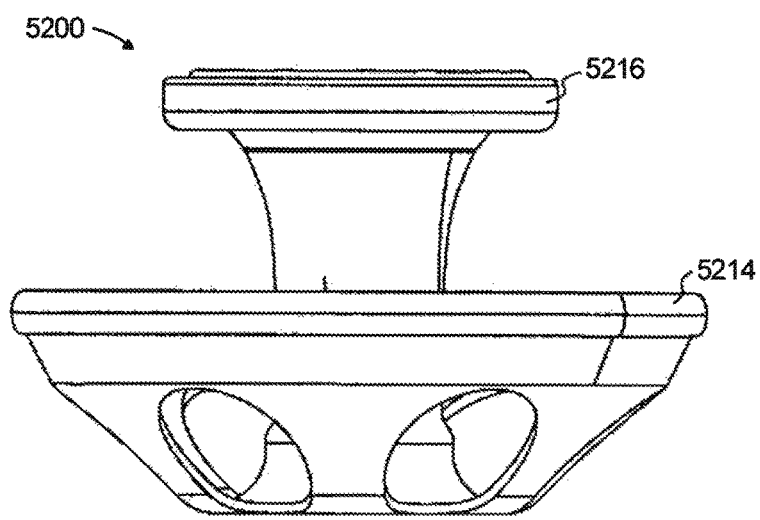
Figure 57:
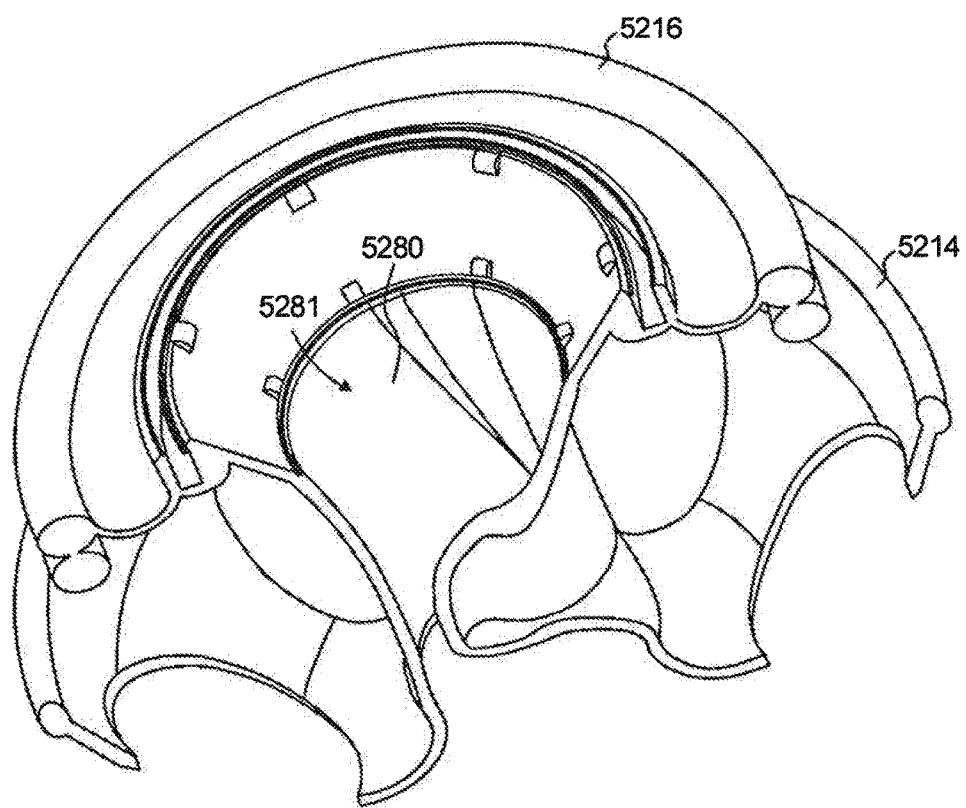
Figure 58:
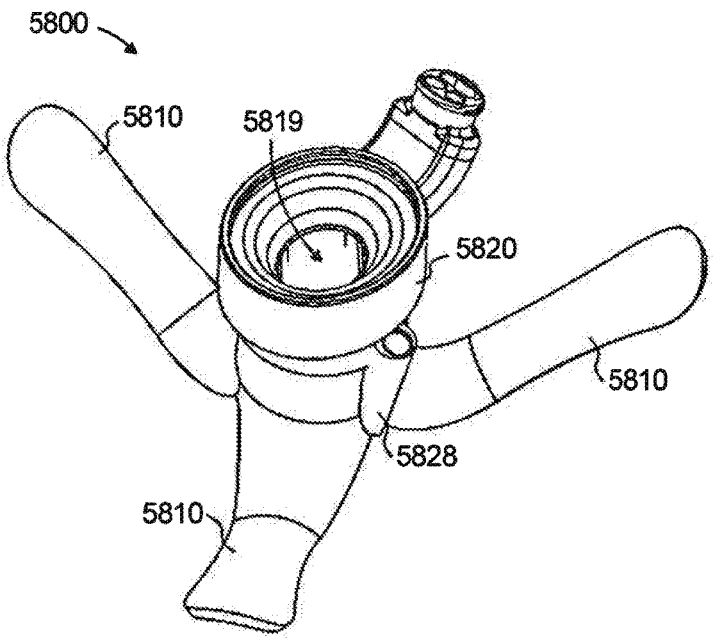
FIGS. 58-62 illustrate a further embodiment of a surgical access device in accordance with the invention, including a plurality of flexible atraumatic anchor portions, which extend outwardly from the body.
Figure 59:
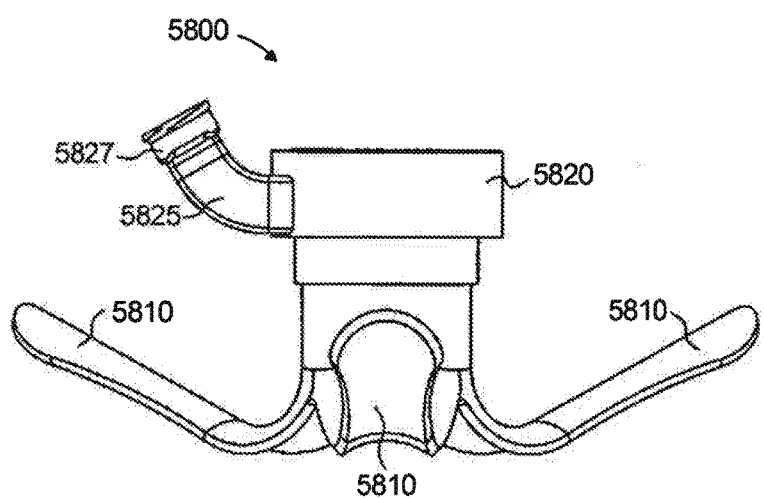

The central tubular portion 5210 includes an undulating configuration, best seen in the top view of FIG. 54, wherein a substantially sinusoidal aperture 5281 is defined between opposite walls 5280, 5282. The aperture 5281 can be completely sealed by the walls 5280, 5282, or alternatively can be configured so as to remain partially open. In any case, the illustrated configuration permits passage of one or more instruments through the lumen 5299 and aperture 5281, while the walls 5280, 5282 move away or "unfold" from the lumen, but without stretching. In this manner, excessive forces are not applied to instruments inserted therethrough. The forces experienced passing through the aperture 5281 are substantially less than for an instrument passing through a typical "duckbill" type seal member.

Further, the configuration of the sinusoidal aperture 5281 and opposed walls 5280, 5282 reduces, the overall cross-sectional area of available area of the lumen 5299, as compared with a fully open (e.g. circular) lumen.

The wound protector 5200 can be inserted through in incision by inverting the web 5212 and distal anchor portion 5214, and inserting the distal end of the wound protector 5200 through the incision. Once inserted sufficiently far, the distal anchor portion 5214 then deploys and maintains the position of the wound protector 5200 in the incision.

FIG. 58-62 illustrate a further embodiment of a surgical access device 5800 in accordance with the invention. The surgical access device 5800 preferably includes a plurality of flexible atraumatic anchor portions 5810, which extend outwardly from the body 5820. Any nozzle configuration can be provided in connection with this embodiment, but as illustrated, the nozzle configuration is that 7000 of FIGS. 70-76(A) (described hereinbelow). It should be understood that the surgical access device 5800 as well as other surgical access devices described herein need not only be provided in connection with a pressure-barrier nozzle (e.g. nozzle 7000), but can be advantageously provided instead, or in addition, with more traditional physical sealing members, such as septum seals, duckbill-type seals, and so on.

Additionally a side access port 5828 is provided, which can be advantageously used to permit passage of and hold an endoscope, for example. In such a manner, the endoscope can be inserted and can remain in position, while other surgical instruments are inserted through the lumen 5819. The housing 5820, as illustrated, is substantially elliptical. Alternatively, the housing 5820 can be round or another shape, for example, as with any embodiment set for the herein.

The connection 5827 for a tube set is provided on the housing 5820 and offset therefrom with an extension 5825, which removes any connection from the area of a patient's skin, and thus minimizes any trauma to the patient's skin in the area of the incision, during a surgical procedure.

The anchor portions 5810 are preferably atraumatic in configuration, and therefore have a relatively wide and rounded configuration. The anchor portions 5810 can be formed of a polymeric material uniquely, or can be formed of a plurality of materials, such as a polymer molded over a metal structure, such as one formed of a spring steel or a shape-memory alloy, for example.

Figure 60:
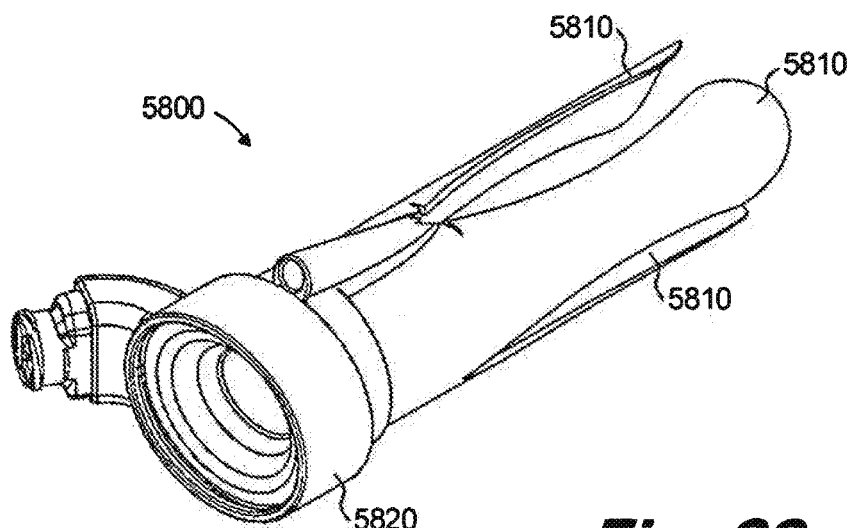
Figure 61:
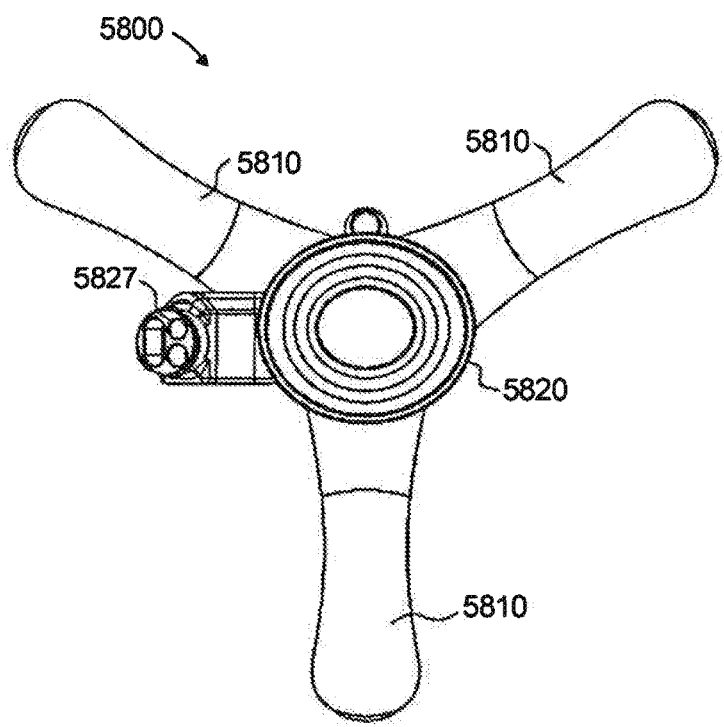
Figure 62:
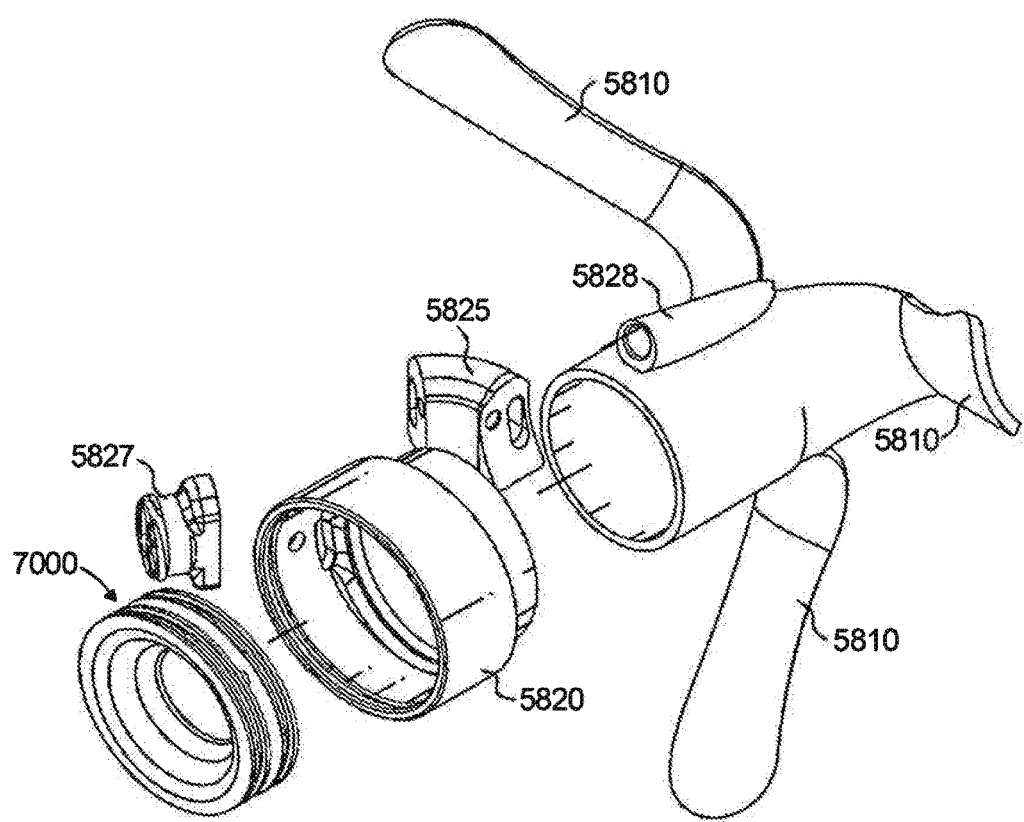
Figure 63:
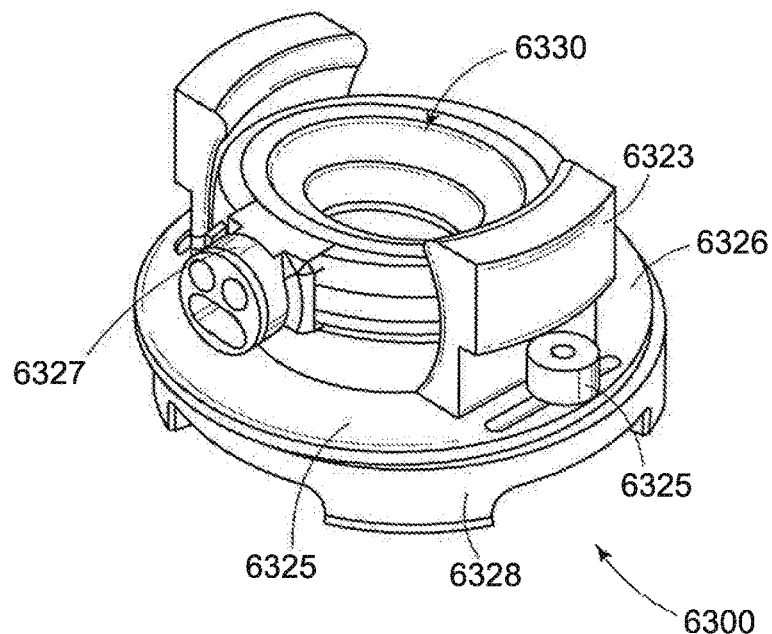
FIGS. 63-69 illustrate still a further embodiment of a surgical access device in accordance with the invention, including a nozzle assembly mounted for spatial adjustability with respect to a base portion thereof.
Figure 64:
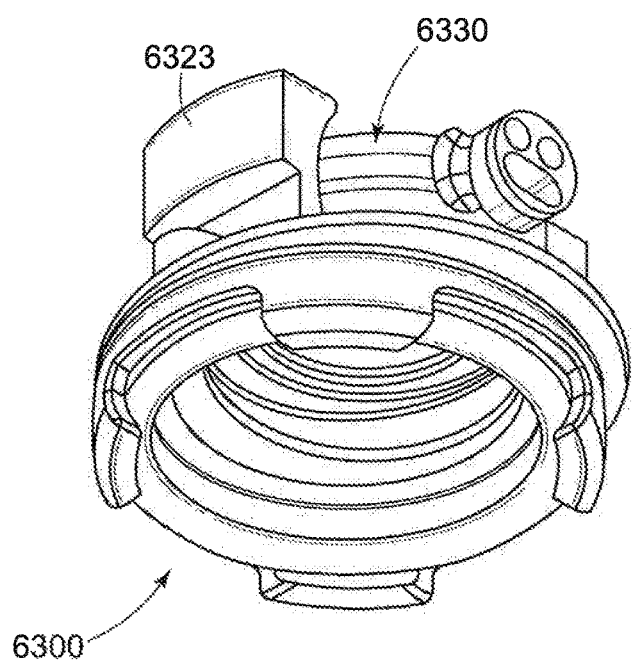
Figure 65:
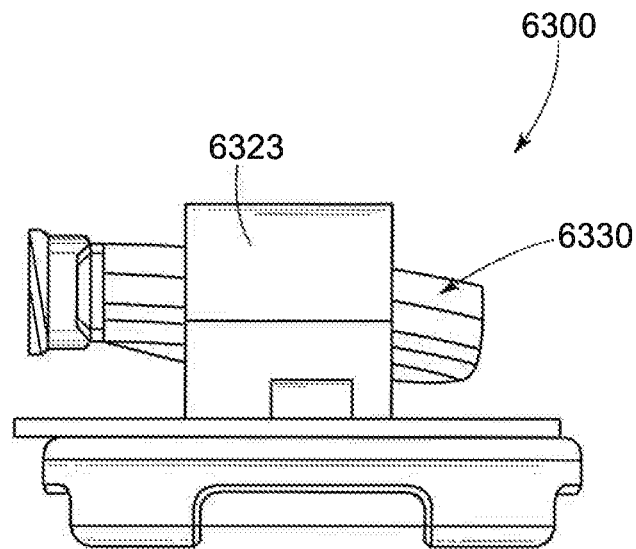
Figure 66:
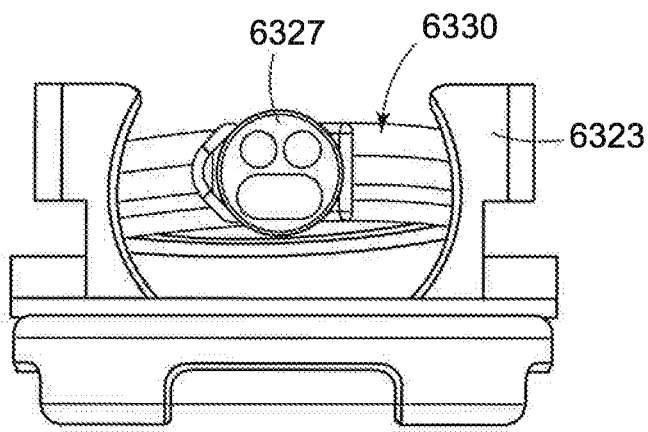
Figure 67:
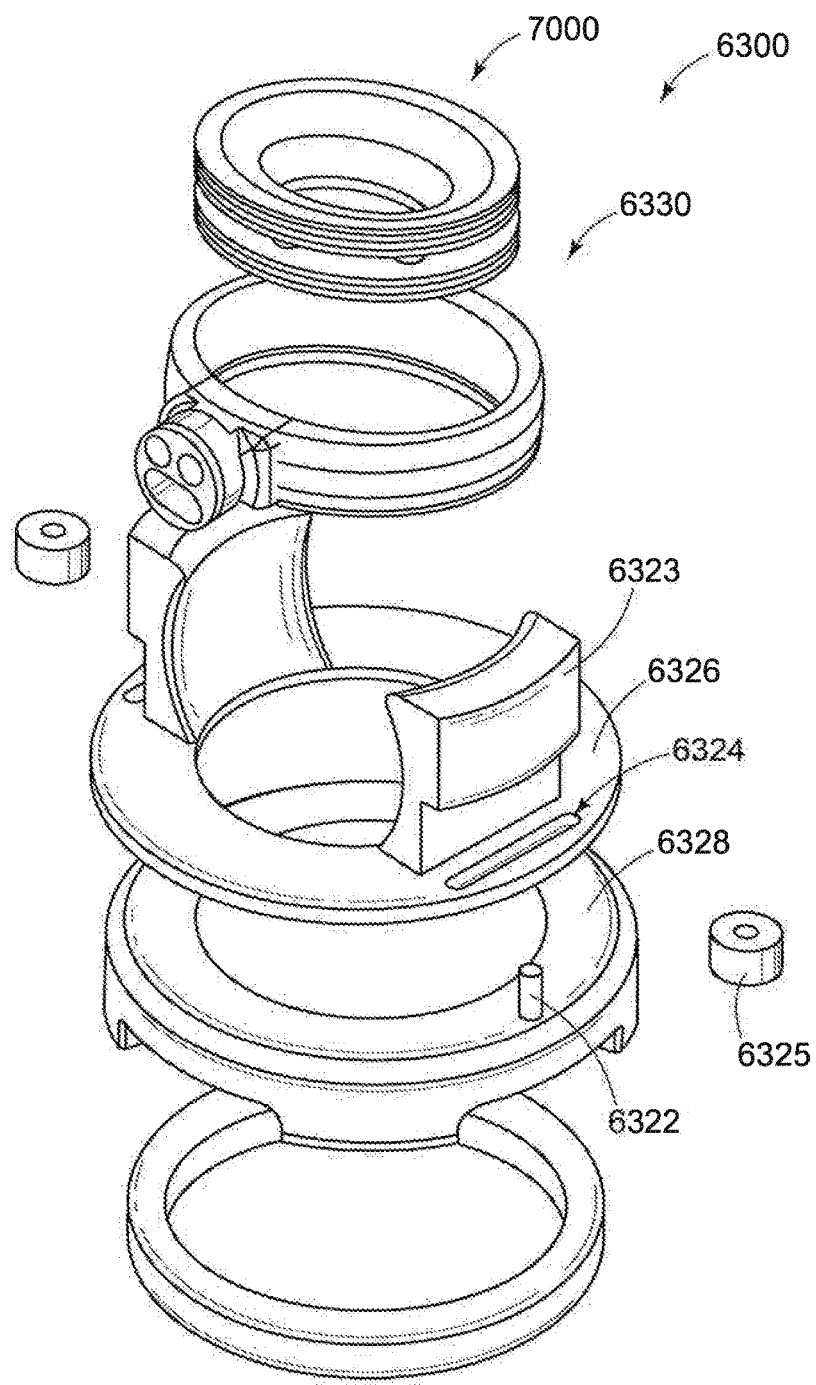
Figure 68:
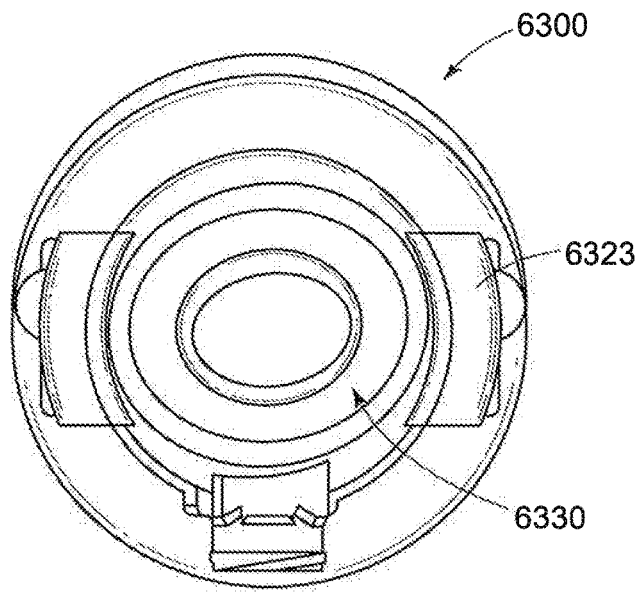
Figure 69:
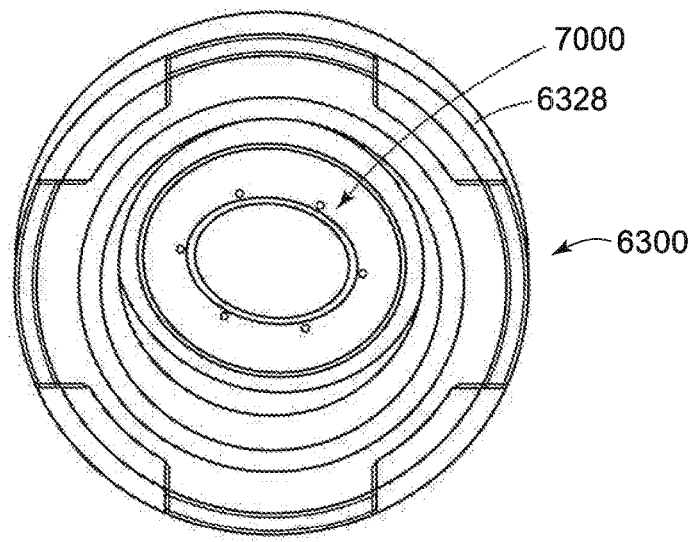
Figure 70:
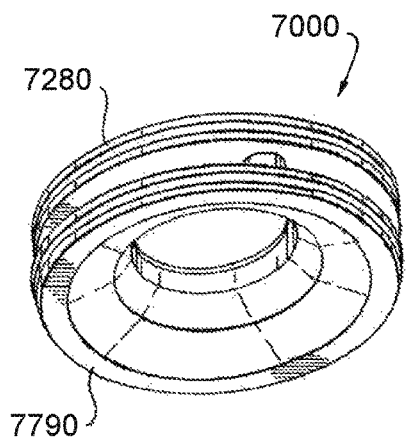
FIGS. 70-76(A) illustrate a nozzle assembly in accordance with the invention, including an upper portion and a lower portion.
Figure 71:
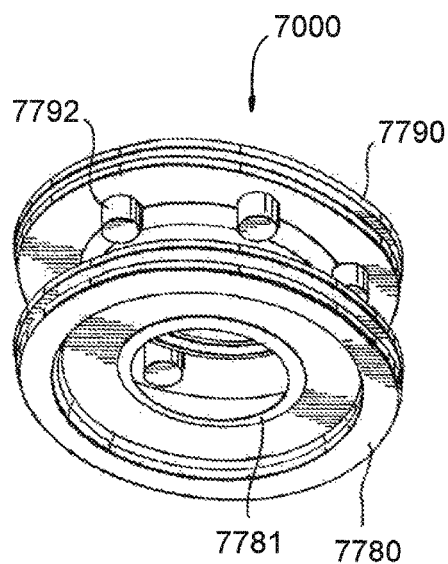
Figure 72:
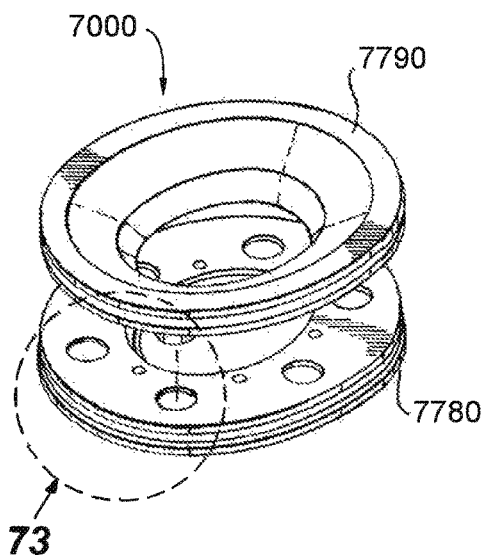
Figure 73:
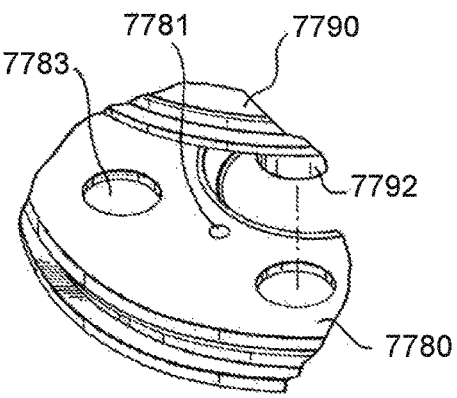
Figure 74:
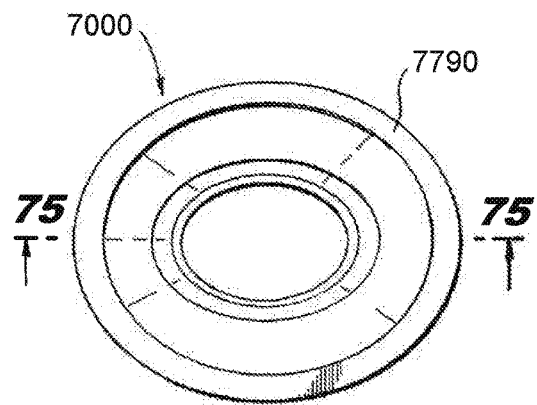
Figure 75:
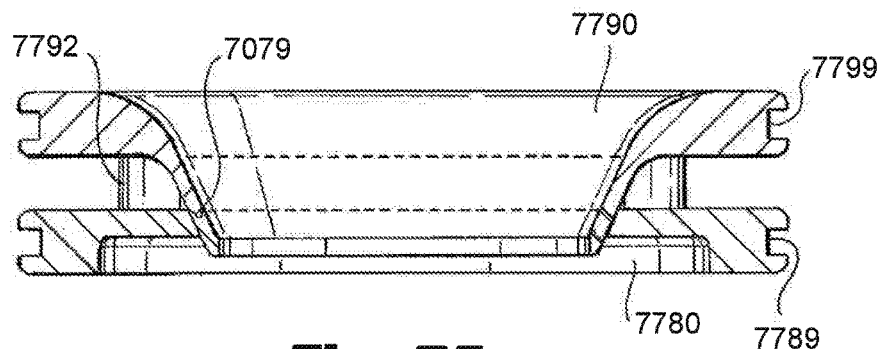
Figure 76A:
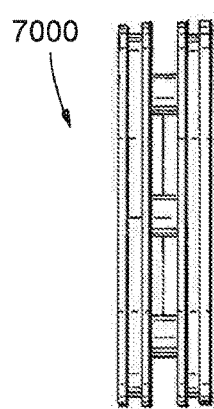
Figure 76:
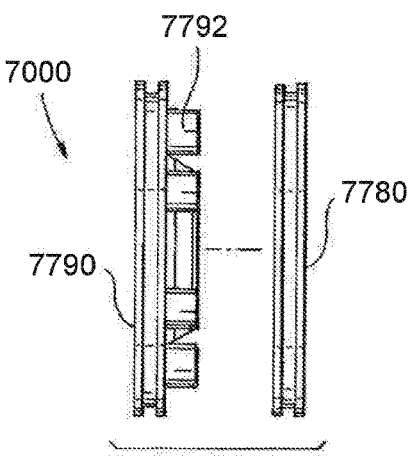

FIG. 60 illustrates the surgical access device 5800 in configuration for insertion through an incision. The anchor portions 5810 are preferably extended from a resting (relaxed) position into a substantially longitudinally-aligned position. In such a configuration, the anchor portions 5810 can be inserted through an incision, maintained in position by hand, or by an insertion device, and then released within the abdominal cavity, when the anchor portions 5810 return to their resting state, and hold the surgical access device 5800 in position in the incision.

FIGS. 63-69 illustrate still a further embodiment of a surgical access device 6300 in accordance with the invention. The surgical access device 6300 includes a nozzle assembly 6330 mounted for spatial adjustability with respect to a base portion 6328 of the surgical access device 6300, and thus an incision to which the surgical access device 6300 is mounted. A tube connection 6327 is provided on the nozzle assembly 6330, which is held by opposed stanchions 6323, having spherical inner surfaces for mating with a spherical outer surface of the nozzle assembly 6330. Accordingly, the nozzle assembly 6330 is permitted to rotate in a substantially spherical path, with respect to the stanchions 6323, the plate portion 6326 to which the stanchions 6323 are secured, a lower portion 6328 of the surgical access device 6300 and therefore, to the incision.

The plate portion 6326, and therefore, the stanchions 6323 and nozzle assembly 6323 are also linearly adjustable, as illustrated, by way of pins 6322, engaging nuts 6325, and corresponding slots 6324 formed in the plate portion 6326.

FIGS. 70-76(A) illustrate various views of a nozzle assembly 7000 in accordance with the invention. The nozzle assembly 7000 includes an upper portion 7790 and a lower portion 7780. Standoffs 7792 and corresponding recesses 7783 are provided to maintain relative spacing, and a pressure plenum therebetween. The upper portion 7790 and lower portion 7780 are sealed to the housing, into which they are inserted, by seal elements, such as o-rings, held in circumferential grooves 7789, 7799 on the outside of the lower portion 7780 and upper portion 7790, respectively. As best seen in the cross-sectional view of FIG. 75, the upper portion 7790 and lower portion 7780 can be sealed at their inner-most edge, causing pressurized fluid to be diverted through discrete jets 7781 distributed about the lower portion 7780. A stepped interface 7079 can be provided between the upper portion 7790 and the lower portion 7780. Moreover, the upper portion 7790 and the lower portion 7780 can be mutually adhered at the protrusions 7792 and or at the stepped interface 7079, for example, to create a sub-assembly and enhance structural stability of the nozzle assembly 7000.

Figure 81A:
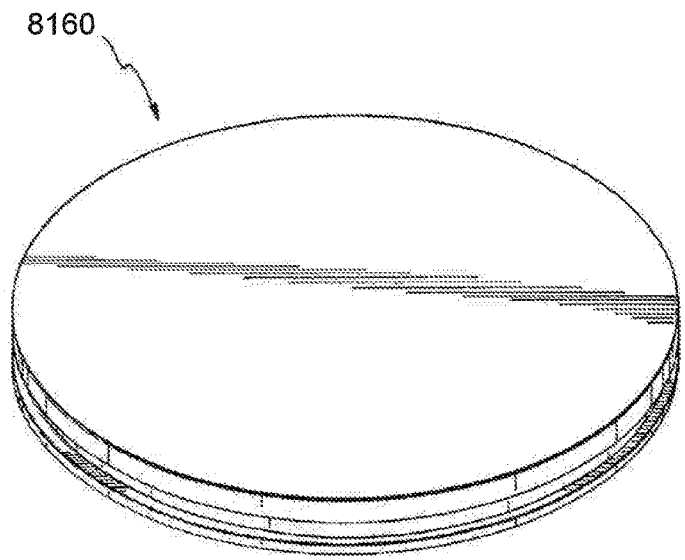
Figure 81B:
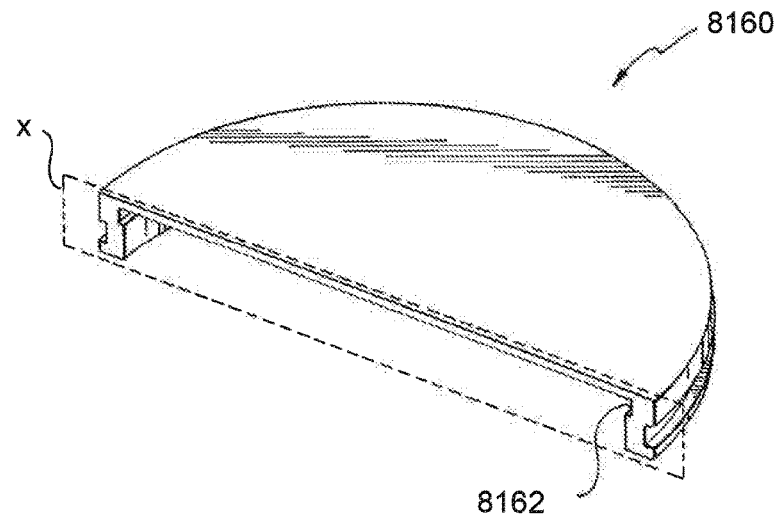
Figure 82A:
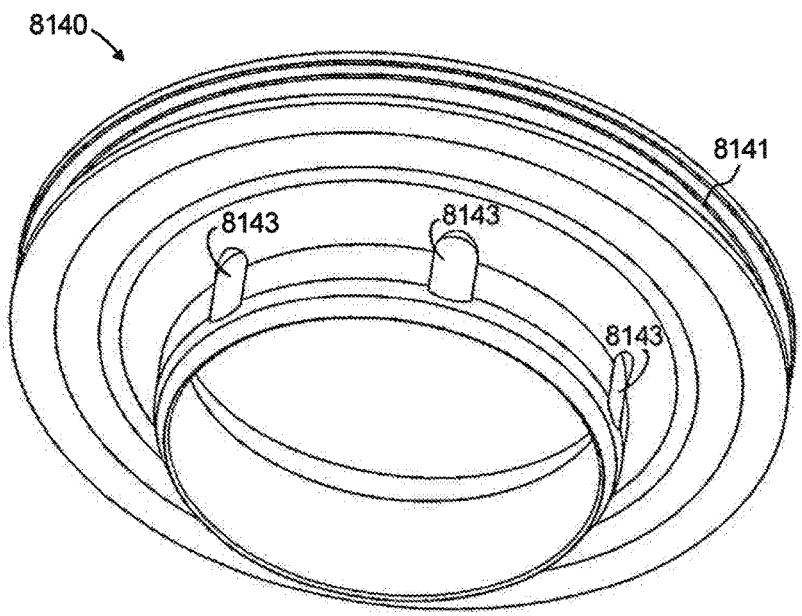
Figure 82B:
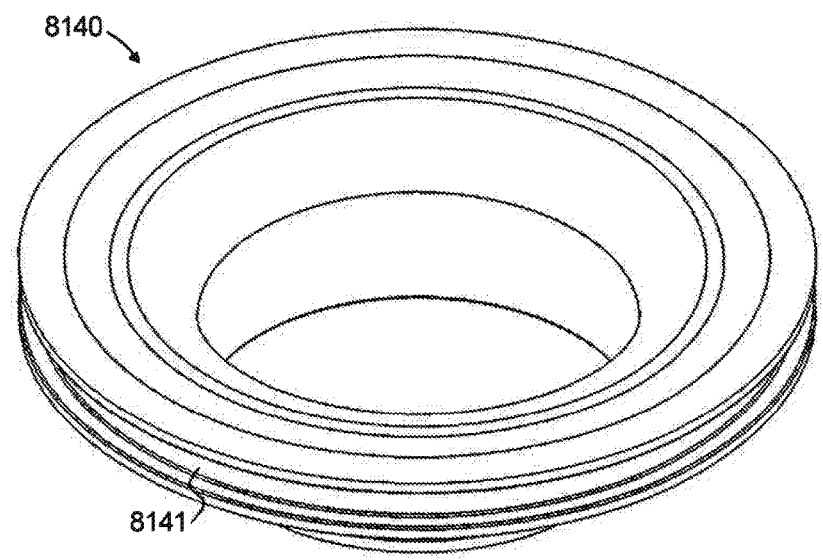
Figure 82C:
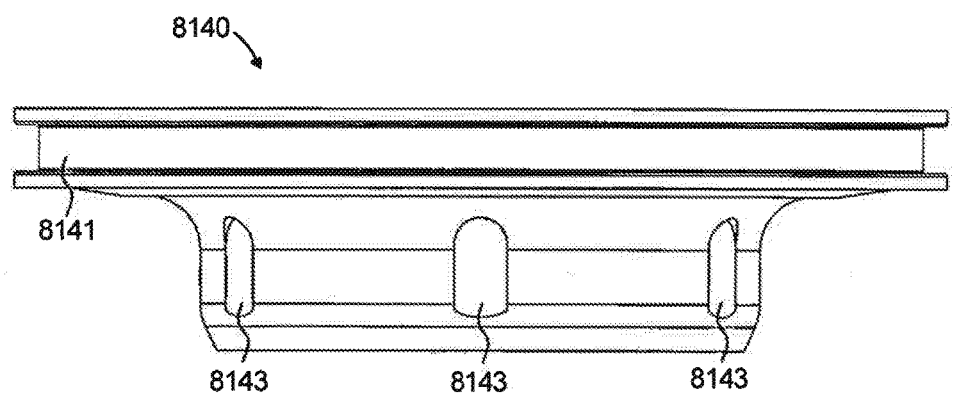
Figure 82D:
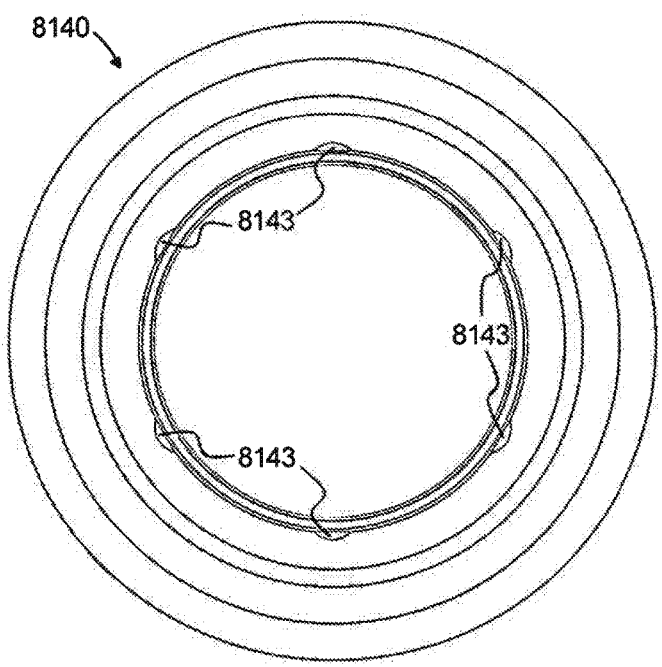
Figure 83D:
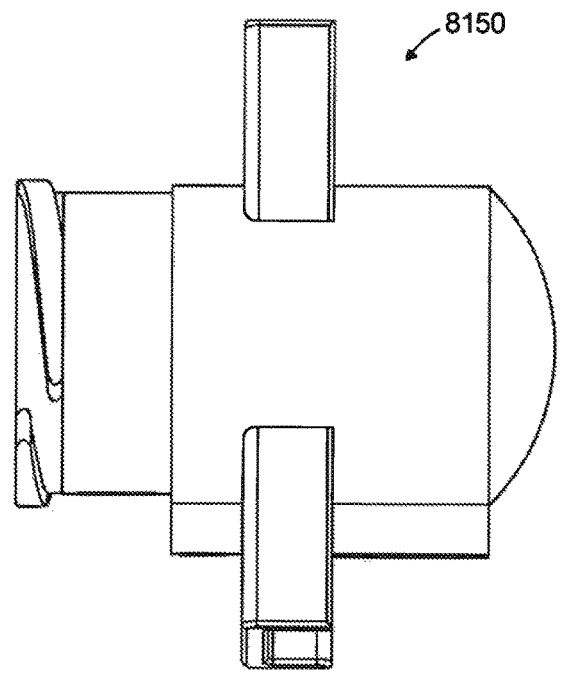
Figure 83E:
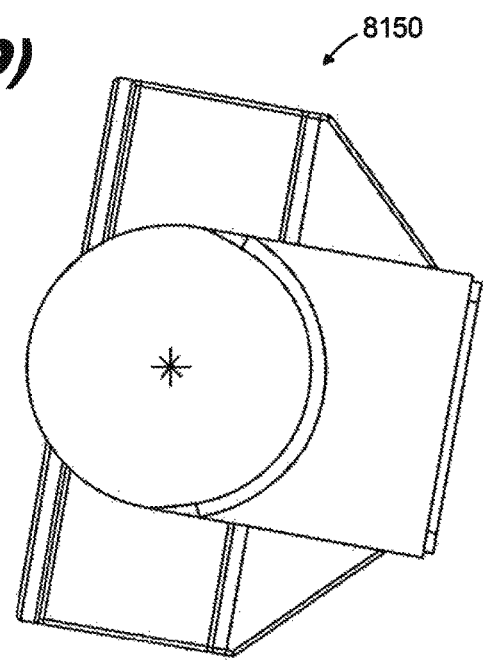
Figure 83F:
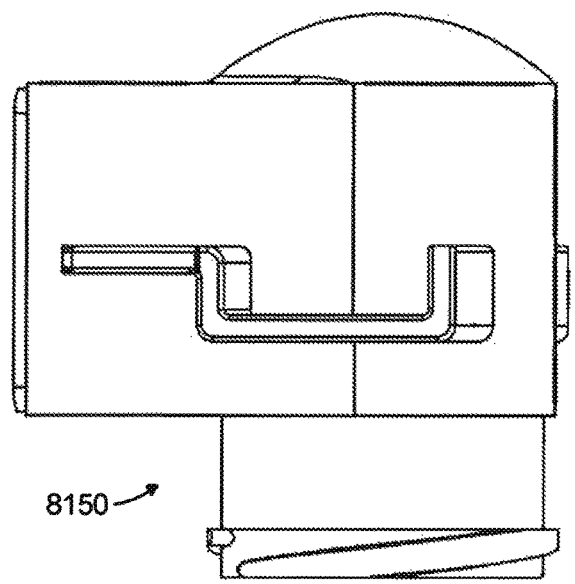
Figure 83G:
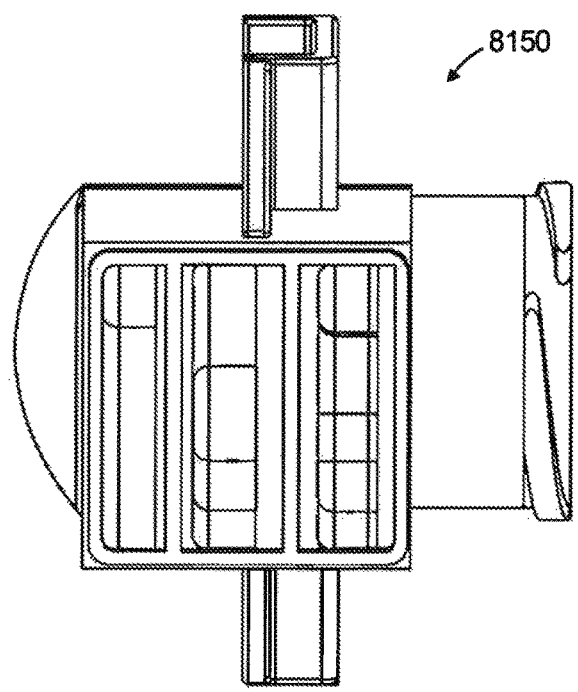
Figure 83H:
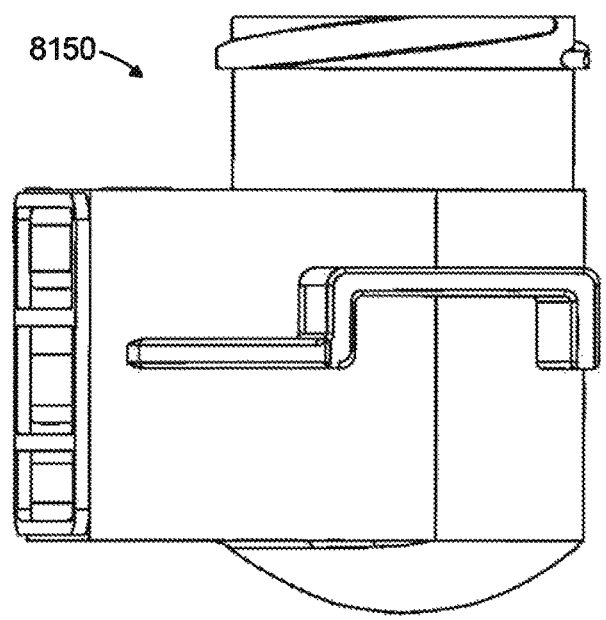
Figure 84A:
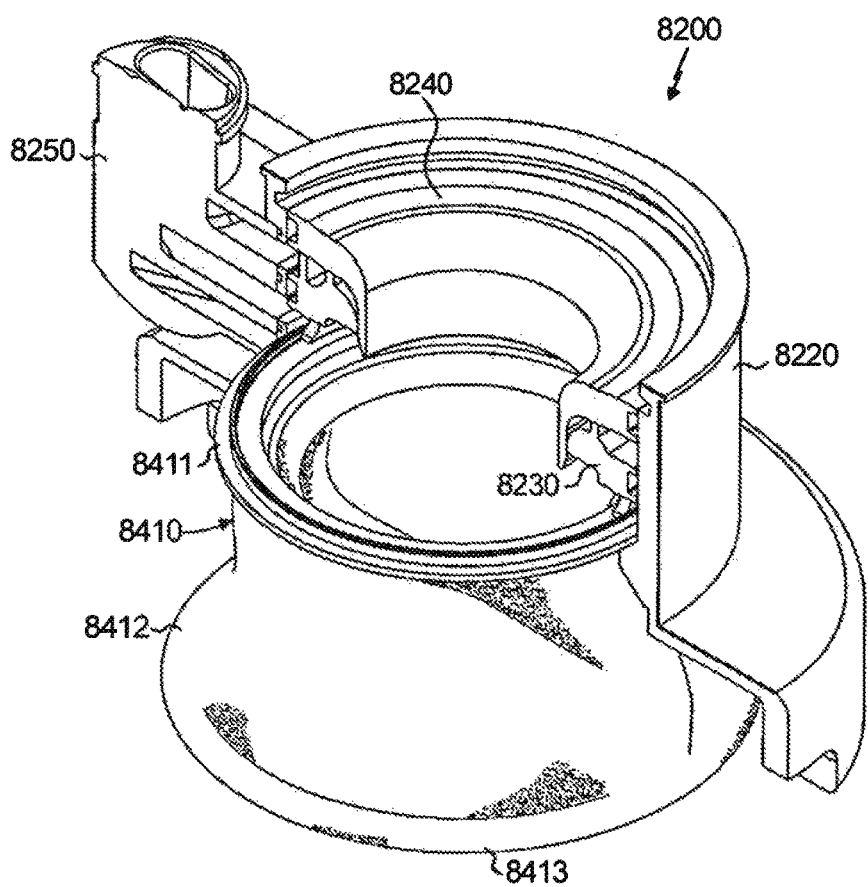
Figure 84B:
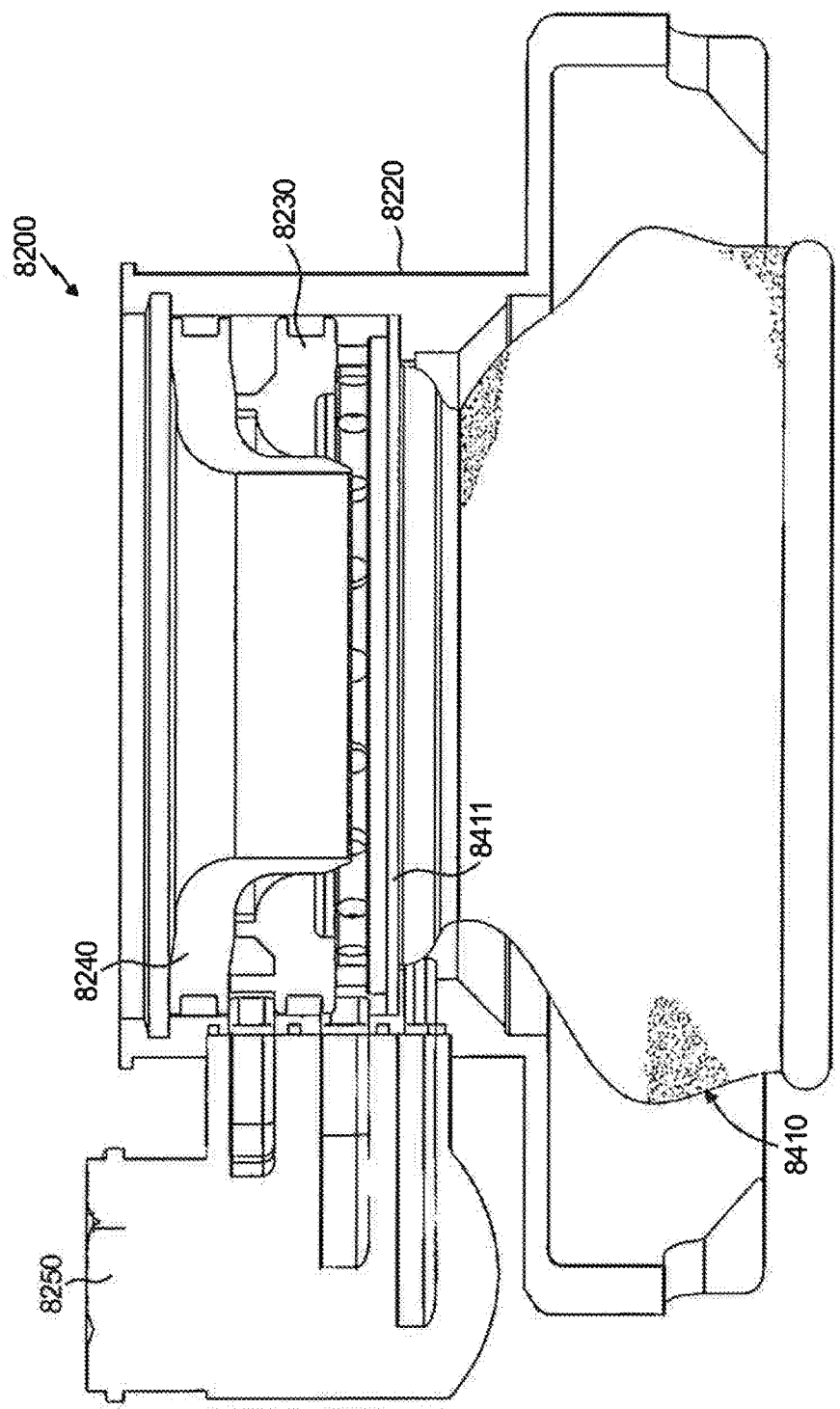
Figure 84C:
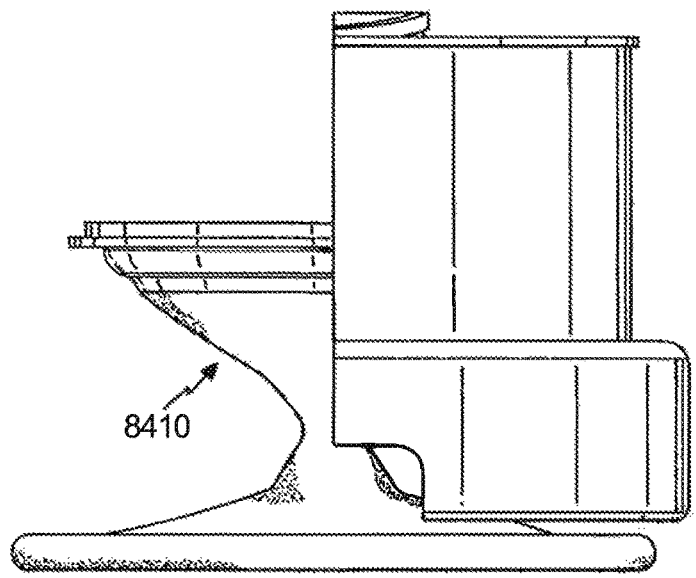
Figure 84D:
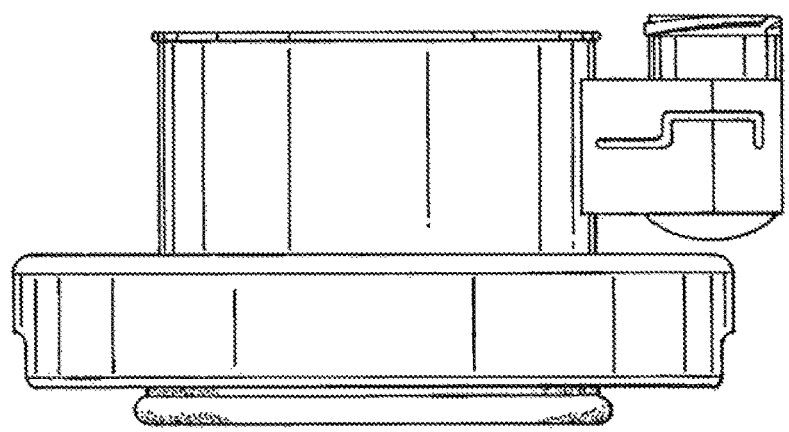
Figure 84E:
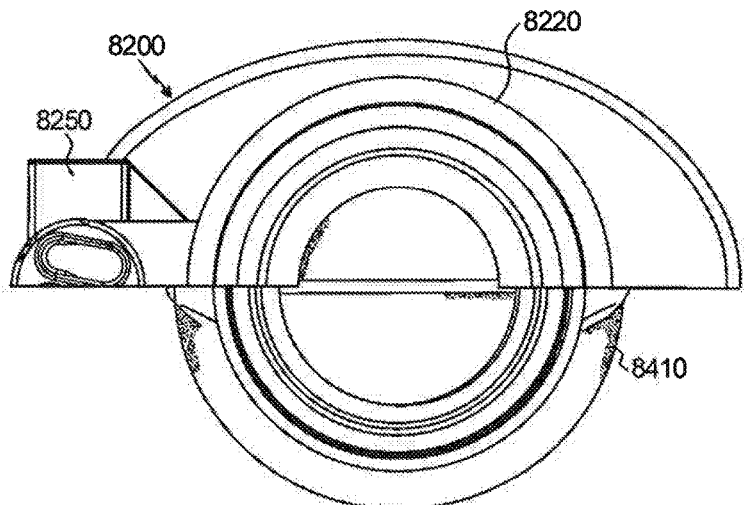
Figure 84F:
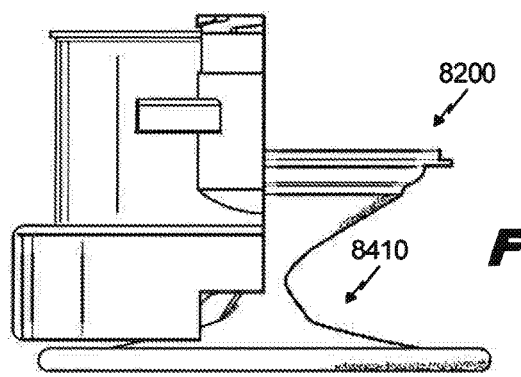
Figure 84G:
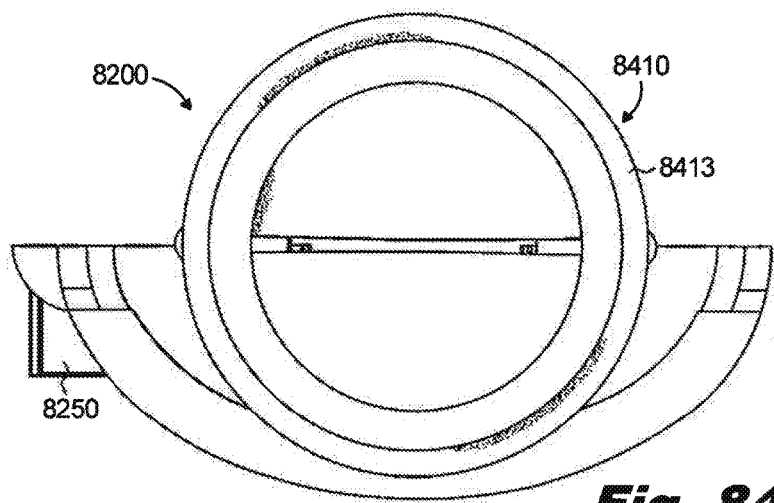
Figure 85A:
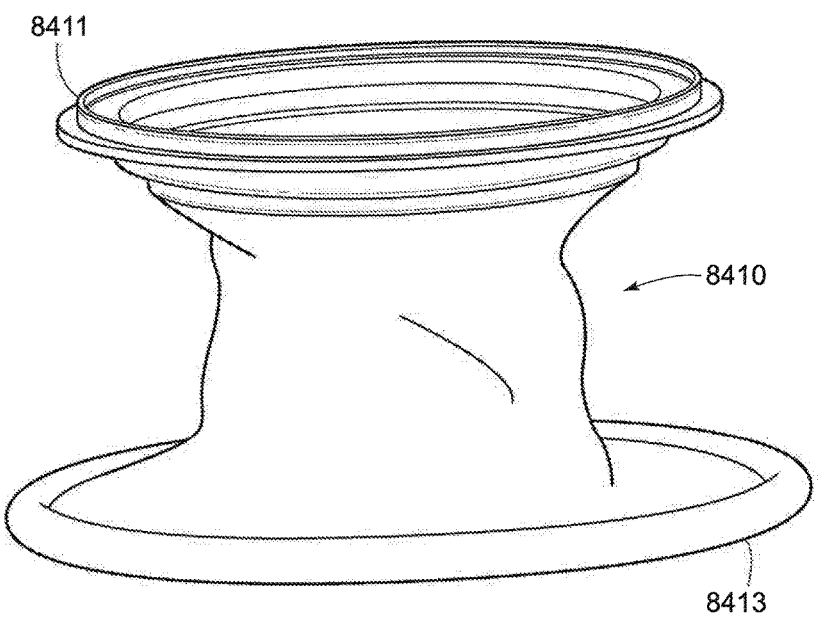
Figure 85B:
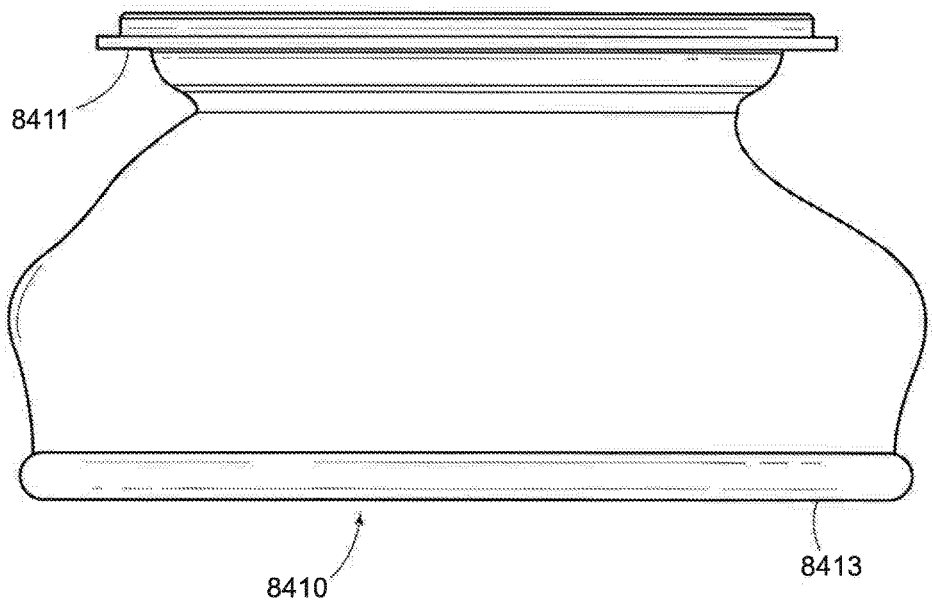
Figure 85C:
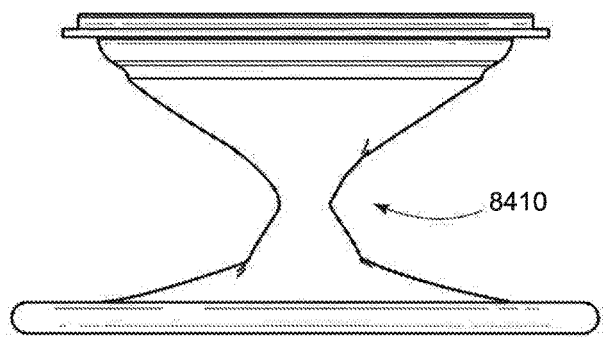
Figure 85D:
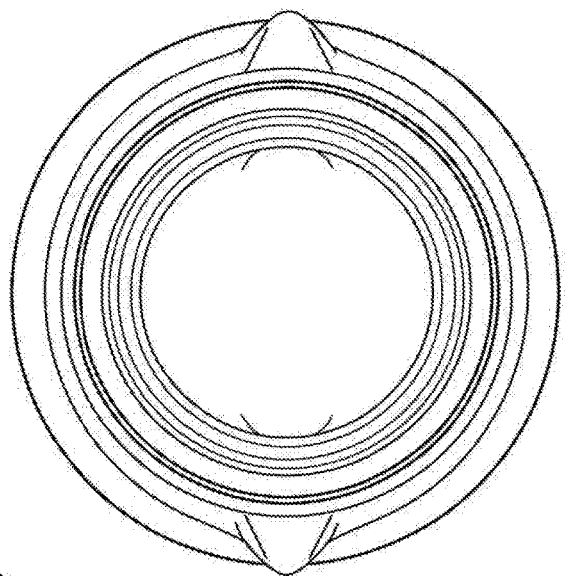
Figure 85E:
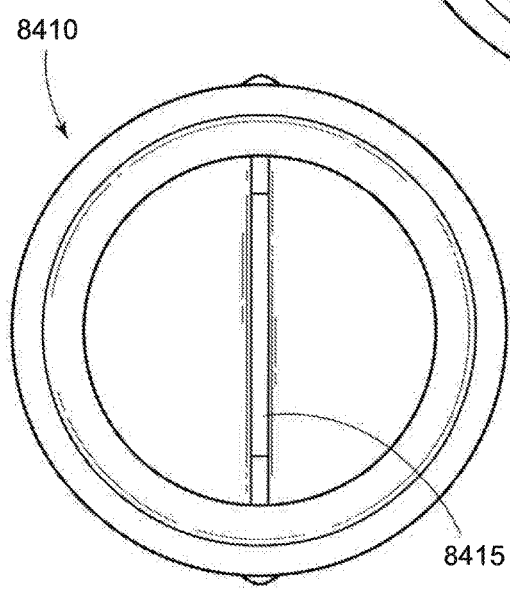

As illustrated in FIGS. 77(A)-77(G), a cut away view of a surgical access device 8100 is presented. Device 8100 is made by assembling a number of nested components discussed in further detail below. As depicted in FIG. 81(A), device 8100 includes, in a nested configuration, an outer cannula or body 8120, an inner cannula/wound retractor 8310, a ring jet assembly 8130, a tube center component 8140 and a fluid manifold 8150 attached to an exterior portion of the outer cannula 8120. A cap 8160 may also be provided as illustrated in FIGS. 81(A)-81(B) and as discussed in detail below. Each of the aforementioned components will now be illustrated in further detail.

Various views of outer cannula 8120 are depicted in FIGS. 80(A)-80(G). As illustrated, outer cannula 8120 has a proximal end 8122 helping to define a proximal region 8122A, a distal end 8124 helping to define a distal region 8124A, and defines a longitudinal bore 8126 therethrough. The external surface of outer cannula 8120 defines thereon a mounting fixture 8125 to receive a fluid manifold 8150, described below. As illustrated, fluid manifold 8150 defines therethrough three fluid passages that initiate at ports 8152 on the top of manifold 8150 and that terminate at slots 8123 defined through the side of outer cannula 8120. Each of the aforementioned fluid passages cooperate with the other portions of device 8100 to define fluid passages, or plena. Each plenum, annotated by reference numerals 8520, 8530 and 8540, serves a different purpose in operation of device 8100 as described below. Manifold 8150 is preferably permanently joined to outer cannula 8120 to ensure that the fluid plena remain fluidly separated from each other by way of a gas tight seal.

As illustrated in FIGS. 77 and 84 surgical access device 8100, 8200 can be adapted and configured for use with any desired tubular surgical access device, such as a flexible inner cannula/wound retractor 8310, 8410 (FIGS. 78(A)-78(E), 85(A)-85(E)), for example. Examples of wound retractors are set forth in U.S. Pat. Nos. 5,524,644, 3,347,226, 3,347,227, 5,159,921, 5,524,644, 6,450,983, 6,254,534, 6,846,287, 5,672,168, 5,906,577, 6,142,936, 5,514,133, 7,238,154, 6,945,932, 6,908,430, 6,972,026, 5,741,298, or 6,945,932, which disclosures are incorporated herein by reference in their entirety.

In such embodiments, the wound retractor 8310 can be inserted through an incision formed in the patient, and secured by any suitable means. In the disclosed embodiment, the outer cannula 8120 is assembled with retractor 8310 in advance of any medical procedure. As illustrated, and as best seen in the cross-sectional views of FIGS. 77(A)-77(G), a flexible wound retractor 8310, which includes a sheath body 8312, distal ring 8313 and proximal ring 8311. Proximal ring 8311 is held in place by the assembly of nested components 8120, 8130, 8140. The distal and proximal rings 8311, 8313 are typically made of a compliant material, such as a rubber, foam rubber or the like, and thus have an inherent shape and size.

For purposes of further illustration, and not limitation, tube center component 8140 and ring jet assembly 8130 nest to form one or more fluid jets. Specifically, as illustrated in FIGS. 82(A)-82(D), tube center component 8140 defines one or more detents 8143 on its outer surface. When the outer surface of center component 8140 nests within the inner surface of ring jet assembly 8130, the detents 8143 cooperates with the inner surface of ring assembly 8130 to form a conduit that is in fluid communication with high pressure plenum 8520 (FIG. 77(B)). High pressure plenum 8520 is pressurized with a working gas so as to drive a high speed gas flow through each of the jets disposed about the periphery of the distal circumferential interface 8524 of the center component 8140 and the ring jet 8130. A fluid tight seal about plenum 8520 is ensured by seals 8554, 8556 disposed in circumferential grooves 8141, 8131 formed in each of center tube portion 8140 and ring jet 8130, respectively.

Proximal ring 8311 of inner cannula/wound retractor 8310 is captured between and seals against inner ridge 8129 of outer cannula 8120 and distal circumferential face 8136 of ring jet 8130. When assembled, these components cooperate to define sensing plenum 8540 in cooperation with dedicated passageway 8542 in manifold 8150 and exhaust or recirculation plenum 8530 for evacuating gas and other fluids from device 8100 and/or the abdomen of the patient into a filtration and recirculation assembly (not shown). Openings 8135 in ring jet 8130 facilitate passage of recirculating fluids.

Figure 77A:
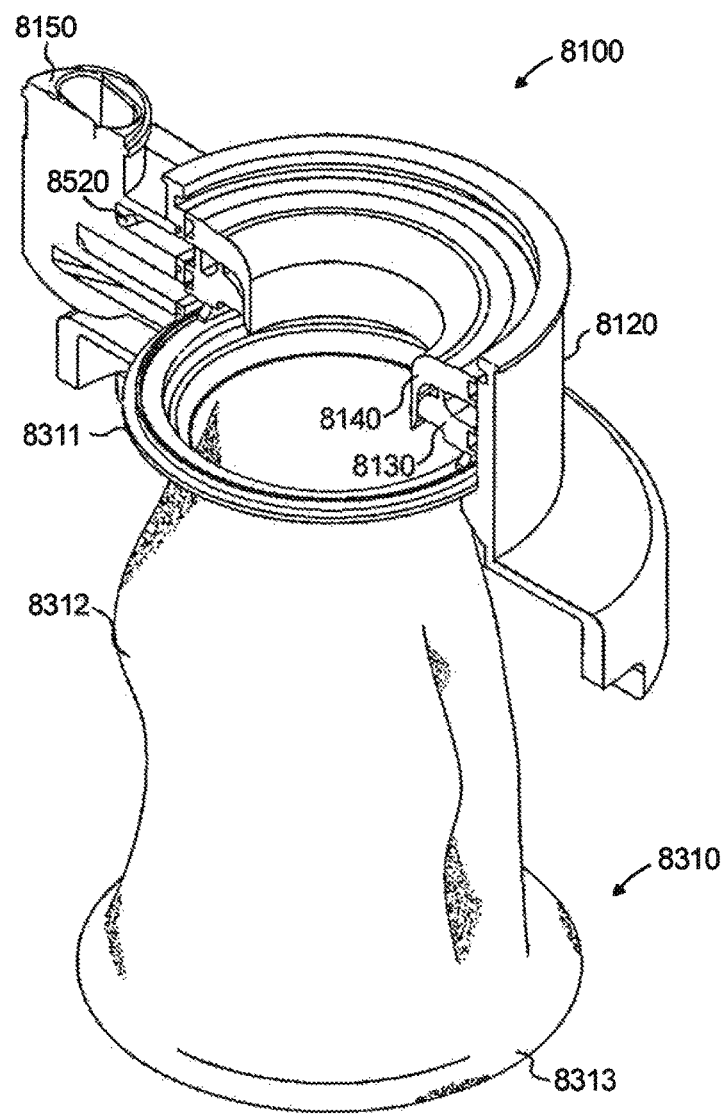
Figure 77B:
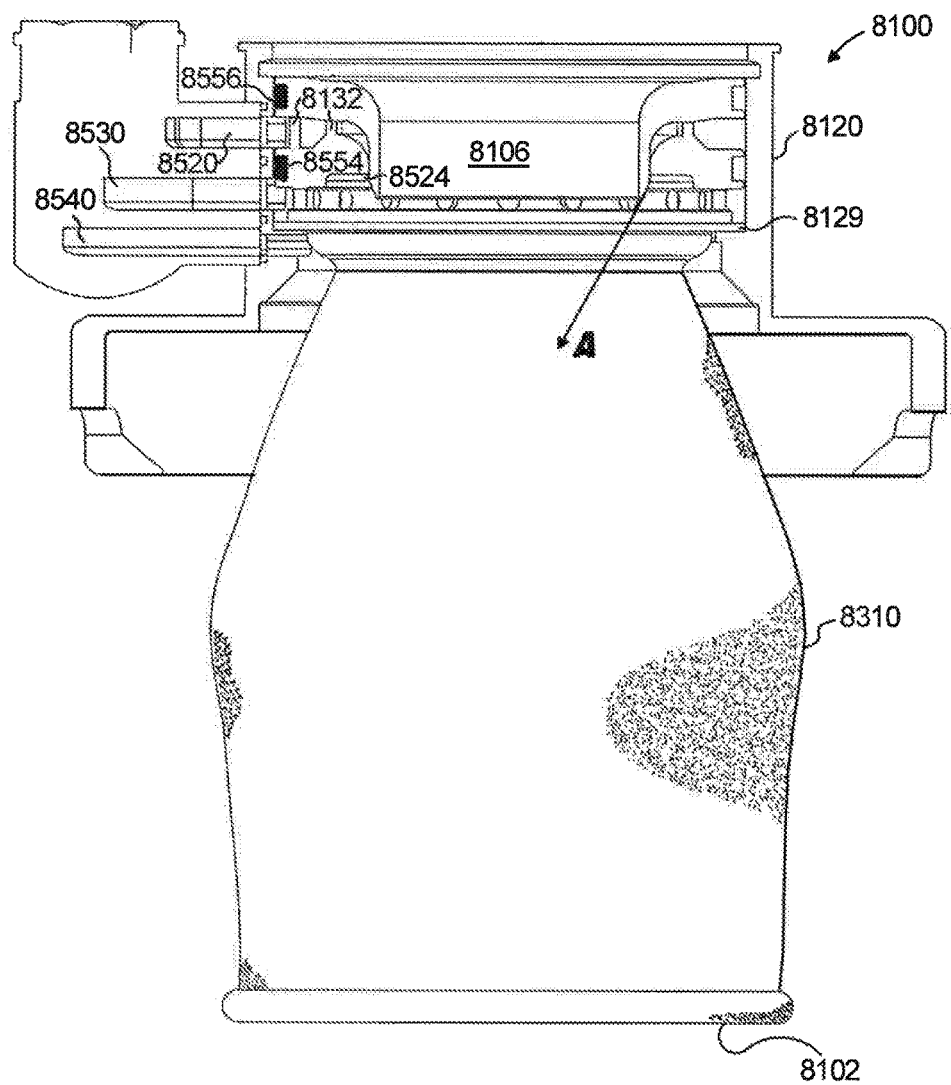
Figure 77C:
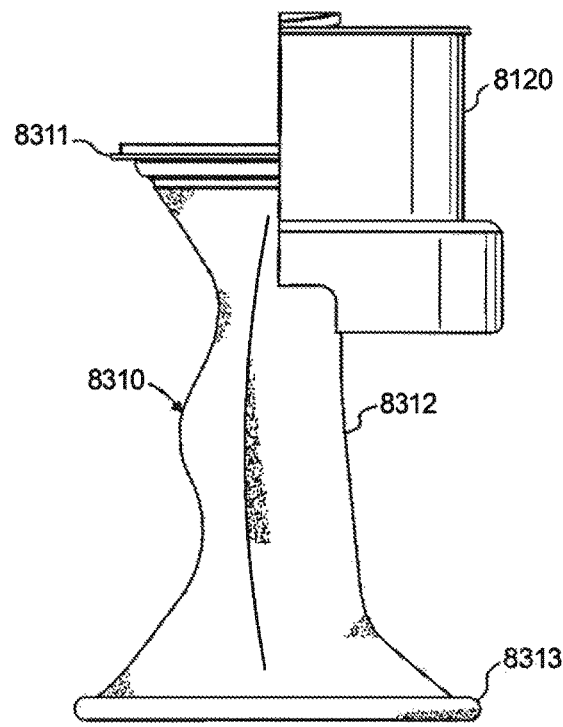
Figure 77D:
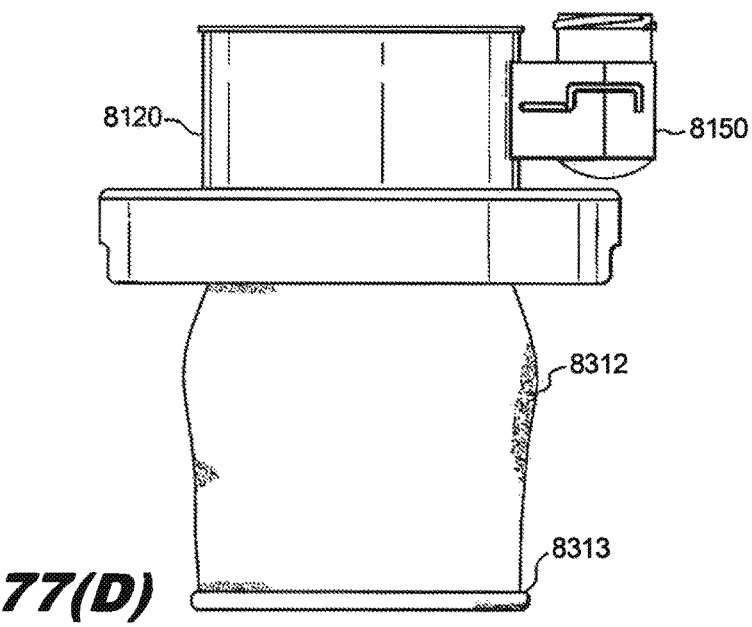
Figure 77E:
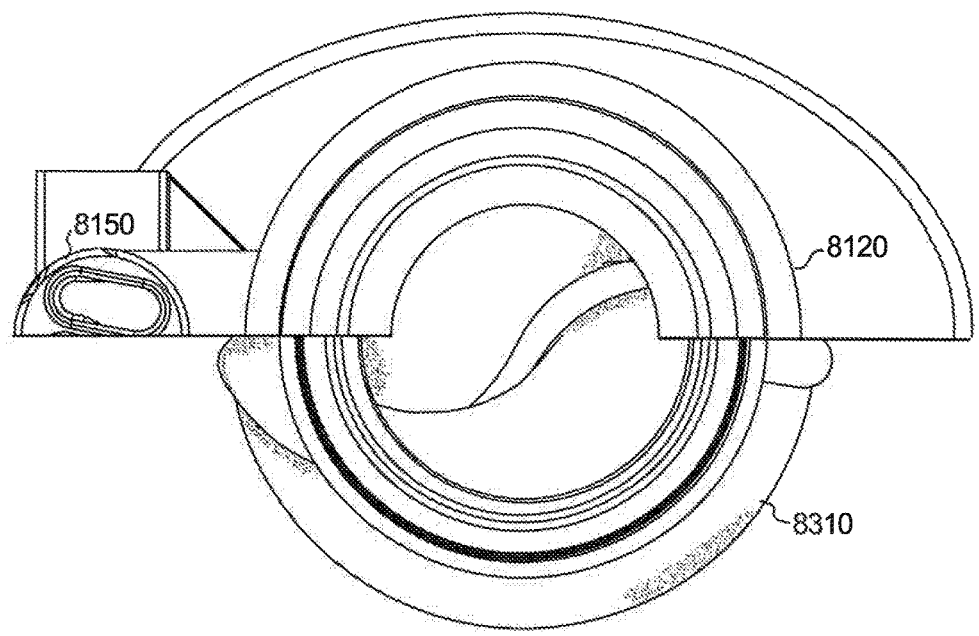
Figure 77F:
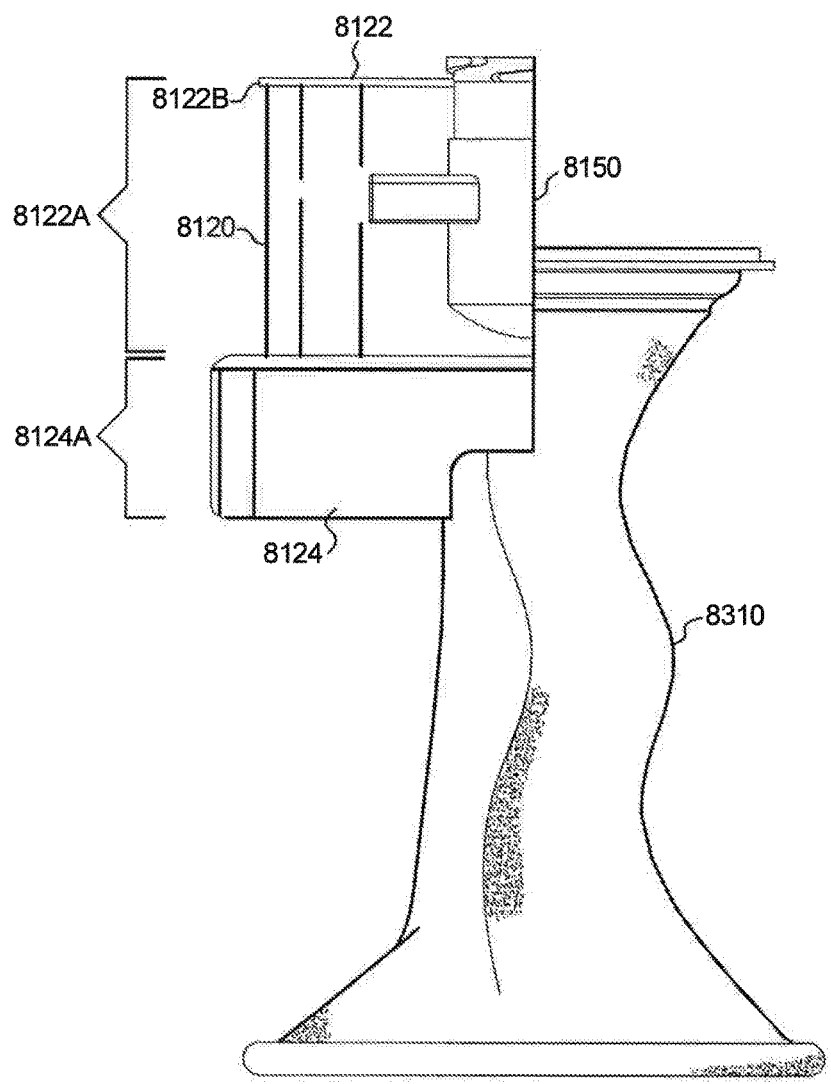
Figure 77G:
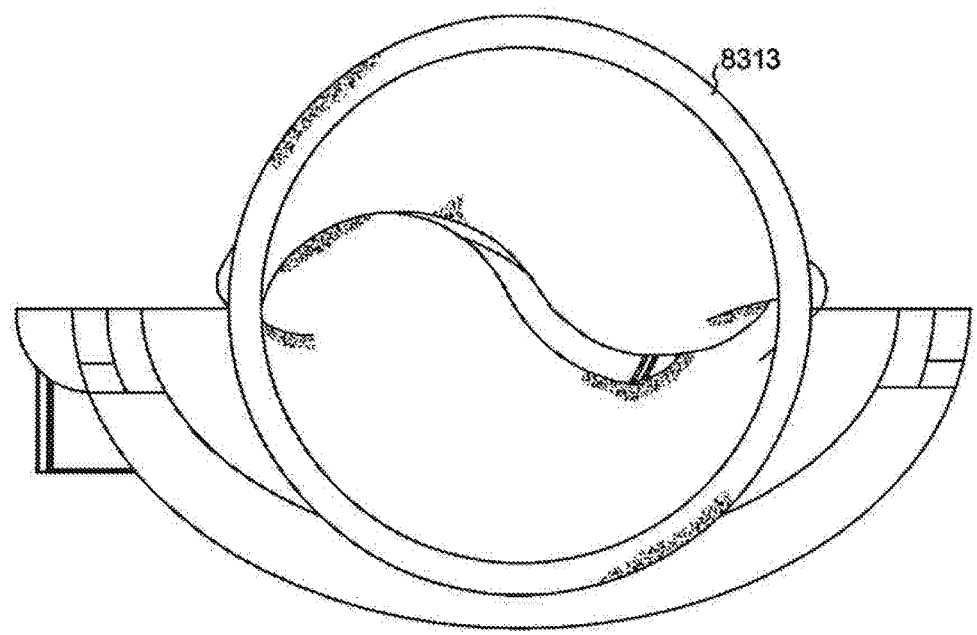
Figure 78A:
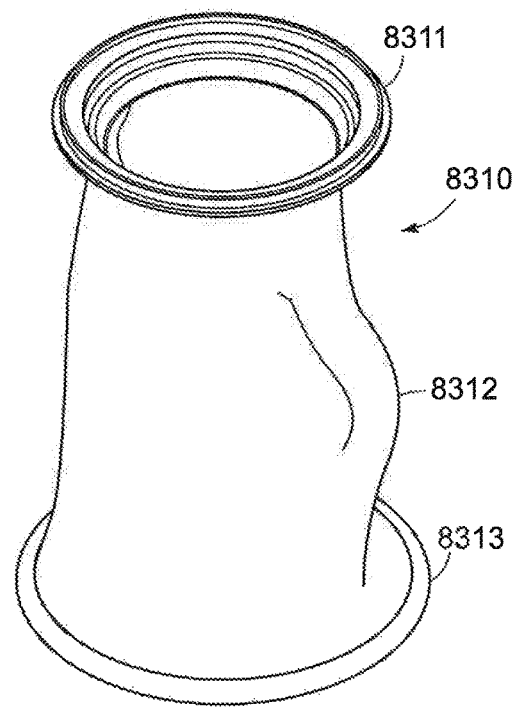
Figure 78B:
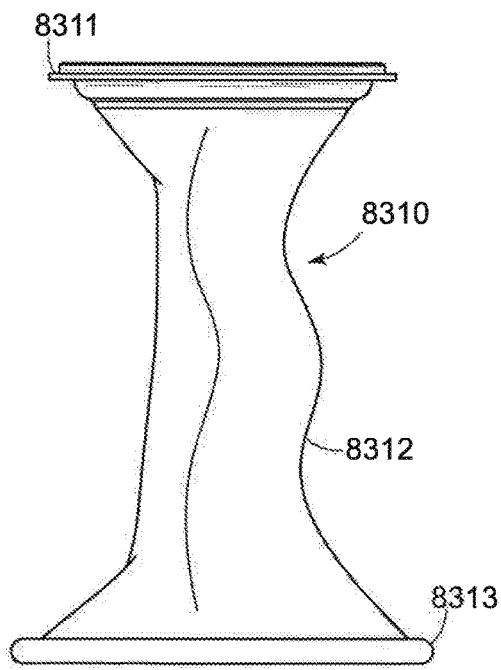
Figure 79A:
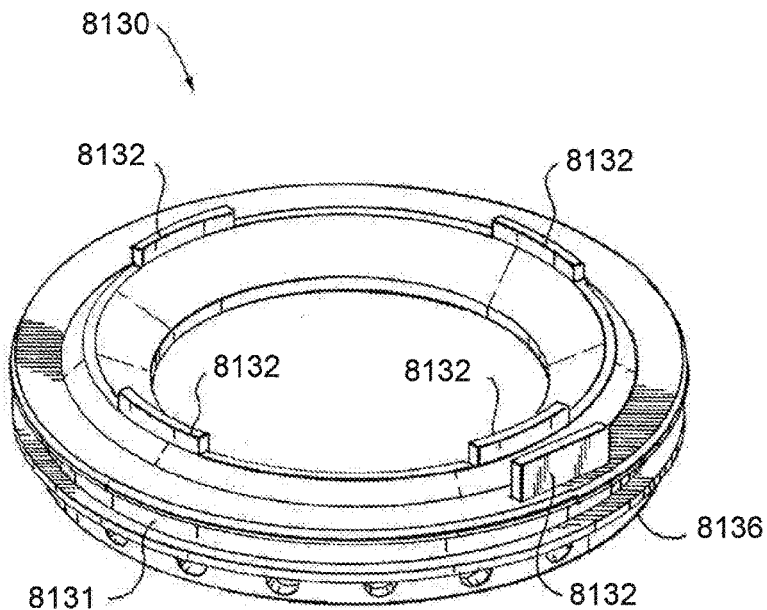
Figure 79B:
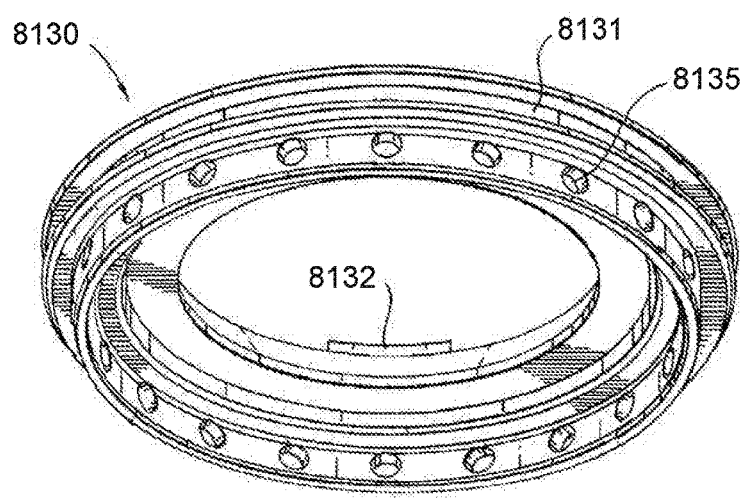
Figure 79C:
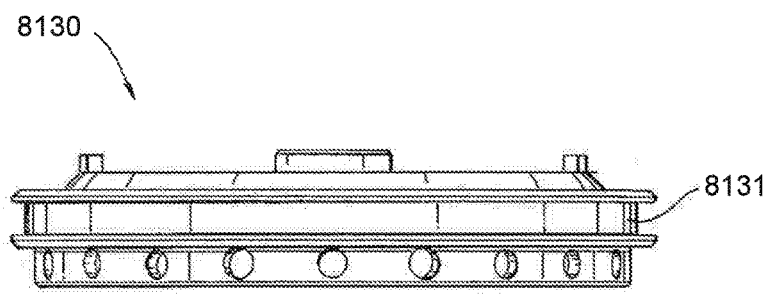
Figure 79D:
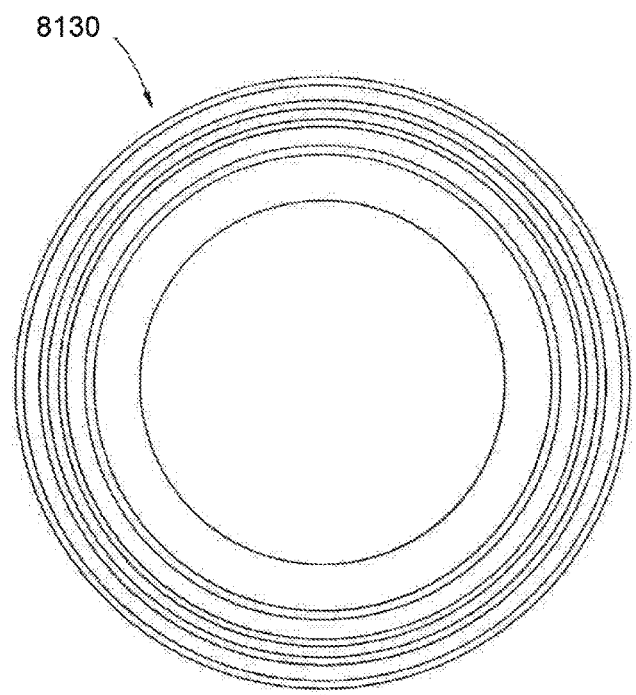
Figure 80A:
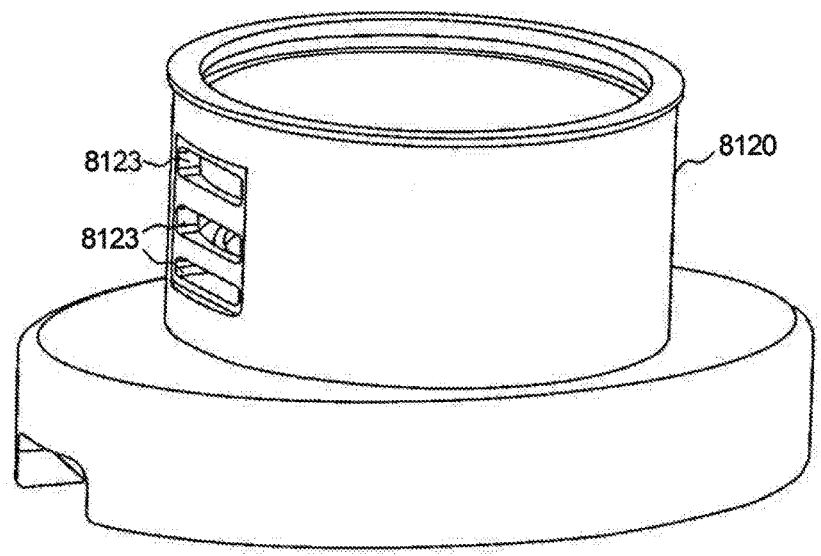
Figure 80B:
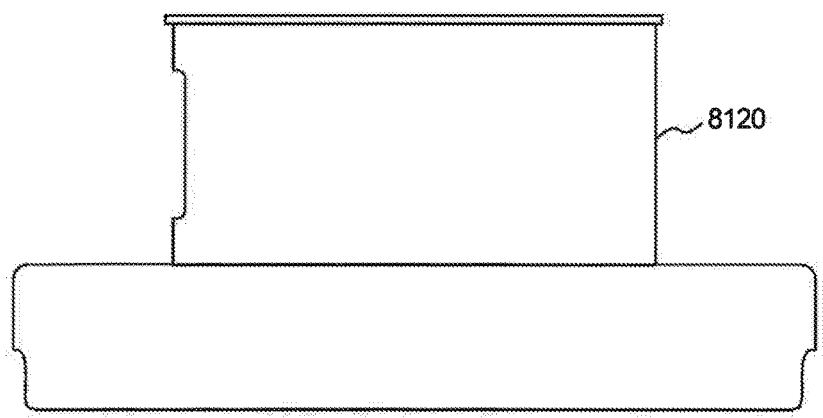
Figure 80C:
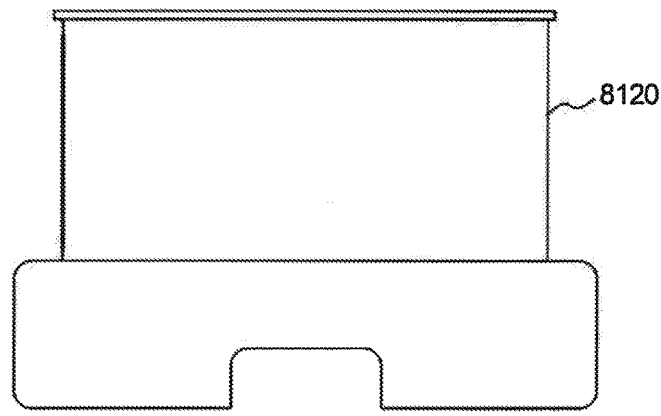
Figure 80D:
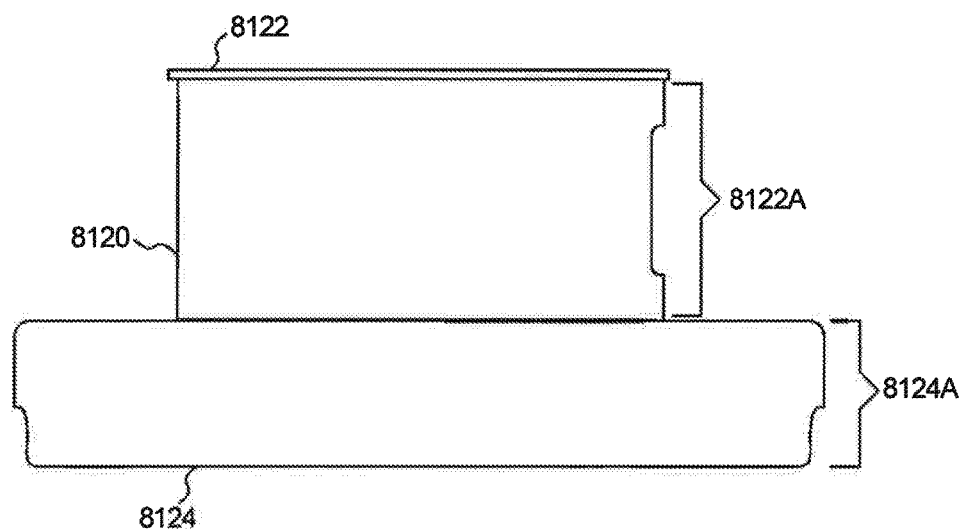
Figure 80E:
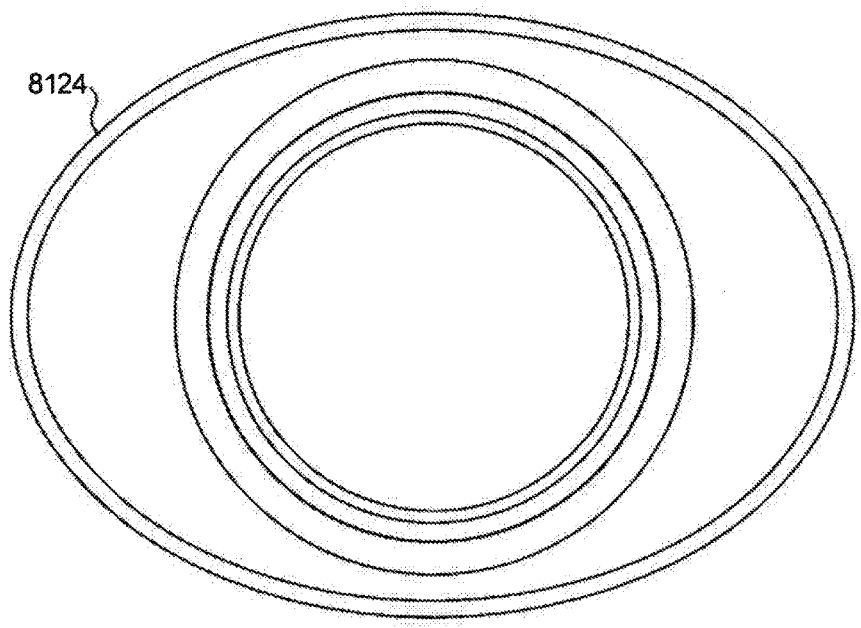
Figure 80F:
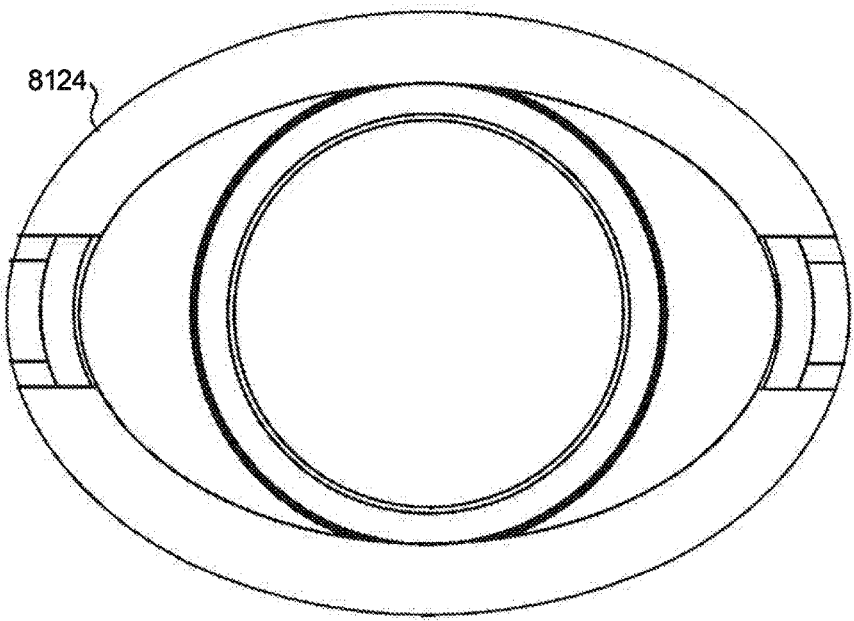
Figure 80G:
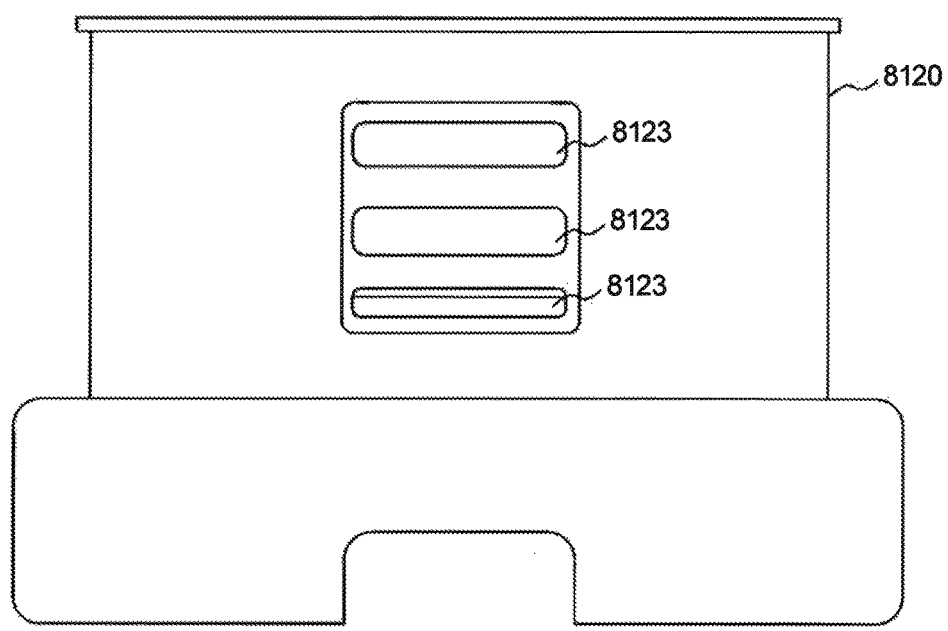

Preferably, the gas jets exit and wrap around the outer distal surface of the center tube component before breaking free of the surface, thus obtaining some angularity with respect to a longitudinal axis of the trocar, such that the main direction of the jet flow is generally off-axis, indicated for example by arrow "A" in FIG. 77(B). The momentum of the gas exiting the circumferentially disposed peripheral jets forms a pressure gradient inside the bore 8106 of the device 8100, such that the pressure at the distal end 8102 of the device can be about 15 mm of Hg higher than the atmospheric pressure outside the trocar in the operating room. Proper axial spacing between center tube assembly 8140 and ring jet 8130 is ensured by the height of proximal spacers 8132 disposed on the proximal face of the ring jet 8130.

In operation, sensing plenum 8540 includes one or more pressure sensors (not shown) in a fluid flow control unit (not shown) to maintain the pressure of a patient's abdomen at a preselected pressure (e.g., 15 mm Hg). Suitable gas flow control units are described, for example, in Provisional Patent Application Ser. No. 61/246,921, and provisional Patent Application Ser. No. 61/384,412, filed Sep. 20, 2010, each of which is incorporated by reference herein in its entirety. For example, if the pressure detected in the abdomen is too high, the flow control unit decreases the delivery of gas to plenum 8520, resulting in less gas being delivered through the high speed jets and into the bore 8106 of the device 8100. By way of further example, if the gas pressure is too low in the abdomen, the flow control unit increases the delivery of gas to plenum 8520, resulting in more gas being delivered through the high speed jets and into the bore 106 of the device 8100.

If desired, the outer cannula 8120 and the inner cannula/wound retractor 8310 can be detachable from one another. The inner cannula/wound retractor 8310 can be provided in assorted lengths (see, e.g., the embodiment of FIGS. 84-85) and shapes, and with assorted features, as desired or required. For example, the inner cannula/wound retractor 8310 of FIG. 2 defines an "S"-shaped narrowed region 8315 (FIG. 2(E)) while that of FIG. 85 defines a straight elongate narrowed region 8415 (FIG. 85(E)). Accordingly, a surgeon can decide before or during a procedure what length or diameter inner cannula/wound retractor 8310 to use, and can attach it to the outer cannula 8120 of the access device 8100. Alternatively, a range of access devices of varying diameters, lengths and having varying features can be provided fully assembled to be available to the surgeon.

In accordance with the invention, the access device 8100 can include insufflation capability, can be adapted and configured to form a fluidic seal or barometric barrier around an instrument inserted therethrough and/or can be adapted to facilitate recirculation of insufflation gasses.

As illustrated in FIGS. 81(A)-81(B), a proximal cap 8160 can be applied to the device 8100, and if desired can incorporate sound attenuation features, such as sound absorbing materials or sound attenuation surface features to absorb, cancel or reduce sound created by fluid flowing through the bore 8106 of the access device 8100. As illustrated most clearly in FIG. 81(B) with respect to cross-sectional plane "X", cap 8160 can be provided with an internal circumferential groove 8162 that is adapted and configured to engage flange 8122B (illustrated in FIG. 77(F)) at proximal end 8122 of outer cannula 8120.

FIGS. 84-85 illustrate a further surgical access device 8200 in accordance with the disclosure, which includes an outer cannula 8220, a ring jet 8230, a center tube adapter 8240 and manifold 8250. Embodiment 8200 is substantially the same as embodiment 8100, but has a truncated inner cannula/wound retractor 8410.

As mentioned above, compatible features described in connection with one embodiment of the invention can advantageously be incorporated with other embodiments of the invention. The devices and related methods of the present invention, as described above and shown in the drawings, provide surgical access devices with advantageous properties including anchoring capabilities without causing excessive trauma to the patient. It will be apparent to those skilled in the art that various modifications and variations can be made in the devices, systems and related methods of the present invention without departing from the spirit or scope of the invention.

What is claimed is:

1. A surgical access device comprising:
    a housing having proximal and distal end portions, and defining a central passage;
    an access tube extending distally from the distal end portion of the housing and configured to extend at least partially though an incision formed in an abdominal wall of a patient, wherein the access tube is flexible with an expanded-diameter distal portion to inhibit removal of the access tube from the incision, and the access tube defines a central lumen in direct communication with the central passage of the housing; and
    a cover disposed over the proximal end portion of the housing, wherein the proximal end portion of the housing includes a pressurized fluid plenum defined between an upper nozzle insert and a lower nozzle insert, wherein the plenum is in fluid communication with at least one nozzle formed by the upper and lower nozzle inserts and configured to direct pressurized fluid from the plenum into the central lumen of the access tube to provide a gaseous seal around a surgical instrument inserted therethrough, and wherein the proximal end portion of the housing is provided with an aperture communicating with the central passage of the housing for gas recirculation and a passageway communicating with the central passage of the housing for pressure sensing and insufflation.

2. The device of claim 1, wherein the cover includes a removable lid.

3. The device of claim 1, wherein the cover includes a sound-absorbing material.

4. The device of claim 1, wherein the cover includes an engagement portion adapted to engage with the proximal end portion of the housing.

5. A surgical access device comprising:
    a housing having a proximal end portion and a distal end portion, wherein the housing defines a central passage and a plurality of access ports to permit the insertion of multiple instruments into the central passage; and
    an access tube extending distally from the distal end portion of the housing, defining a central lumen in direct communication with the central passage of the housing and configured to extend at least partially though an incision formed in an abdominal wall of a patient, wherein the access tube is flexible and has an expanded-diameter distal portion to inhibit removal of the access tube from the incision, wherein the housing includes a pressurized fluid plenum defined between an upper nozzle insert and a lower nozzle insert, and wherein the plenum is in fluid communication with at least one nozzle formed by the upper and lower nozzle inserts and configured to direct pressurized fluid from the plenum into the central lumen of the access tube to provide a gaseous seal around surgical instruments inserted therethrough from the central passage of the housing by way of the access ports.

6. The device of claim 5, wherein the plenum chamber has an inlet port for communicating with a source of pressurized fluid.

7. The device of claim 5, wherein the nozzle is defined by a gap defined between an outer periphery portion of the upper nozzle insert and an inner periphery portion of the lower nozzle insert.

8. The device of claim 5, wherein a pressure sensing chamber is defined within the housing, and is adapted and configured to be in fluid communication with the abdominal cavity of the patient through the central lumen of the access tube to facilitate sensing of abdominal pressure.

9. The device of claim 8, wherein the pressure sensing chamber has an outlet port for communicating with a pressure sensor of a connected system.

10. The device of claim 9, wherein the pressure sensing chamber is in fluid communication with a sensing channel defined in the access tube of the surgical access device.

\* \* \* \* \*